US012102692B2

(12) United States Patent
Stankovic et al.

(10) Patent No.: US 12,102,692 B2
(45) Date of Patent: *Oct. 1, 2024

(54) MATERIALS AND METHODS FOR DELIVERING NUCLEIC ACIDS TO COCHLEAR AND VESTIBULAR CELLS

(71) Applicants: Massachusetts Eye and Ear Infirmary, Boston, MA (US); The Schepens Eye Research Institute, Inc., Boston, MA (US); Children's Medical Center Corporation, Boston, MA (US)

(72) Inventors: Konstantina Stankovic, Boston, MA (US); Luk H. Vandenberghe, Weston, MA (US); Jeffrey Holt, Newton, MA (US); Gwenaelle Geleoc, Newtonr, MA (US)

(73) Assignees: Massachusetts Eye and Ear Infirmary, Boston, MA (US); Schepens Eye Research Institute, Boston, MA (US); Children's Medical Center Corporation, Boston, MA (US)

( * ) Notice: Subject to any disclaimer, the term of this patent is extended or adjusted under 35 U.S.C. 154(b) by 332 days.

This patent is subject to a terminal disclaimer.

(21) Appl. No.: 17/450,008

(22) Filed: Oct. 5, 2021

(65) Prior Publication Data

US 2022/0016262 A1 Jan. 20, 2022

Related U.S. Application Data

(63) Continuation of application No. 16/060,841, filed as application No. PCT/US2016/066225 on Dec. 12, 2016, now Pat. No. 11,167,042.

(60) Provisional application No. 62/266,462, filed on Dec. 11, 2015, provisional application No. 62/266,477, filed on Dec. 11, 2015.

(51) Int. Cl.

| | |
|---|---|
| ***A61K 39/00*** | (2006.01) |
| ***A61K 9/00*** | (2006.01) |
| ***A61K 48/00*** | (2006.01) |
| ***A61N 1/32*** | (2006.01) |
| ***C07K 14/005*** | (2006.01) |
| ***C12N 15/86*** | (2006.01) |

(52) U.S. Cl.

CPC .......... *A61K 48/005* (2013.01); *A61K 9/0019* (2013.01); *A61K 9/0046* (2013.01); *A61K 39/00* (2013.01); *A61N 1/32* (2013.01); *C07K 14/005* (2013.01); *C12N 15/86* (2013.01); *C12N 2750/14122* (2013.01); *C12N 2750/14143* (2013.01); *C12N 2750/14145* (2013.01)

(58) Field of Classification Search

CPC .. A61K 48/005; A61K 9/0019; A61K 9/0046; C12N 15/86; C12N 2750/14143; A61P 27/16

USPC .......... 435/6.1, 6.11, 91.1, 91.31, 455, 458; 514/44 A, 44 R; 536/23.1, 24.5

See application file for complete search history.

(56) References Cited

U.S. PATENT DOCUMENTS

| | | | |
|---|---|---|---|
| 5,037,384 | A | 8/1991 | Chang |
| 7,906,111 | B2 | 3/2011 | Wilson et al. |
| 10,119,125 | B2 | 11/2018 | Vandenberghe |
| 11,167,042 | B2 | 11/2021 | Stankovic et al. |
| 2004/0216750 | A1 | 11/2004 | Snyder et al. |
| 2005/0281786 | A1 | 12/2005 | Poulsen et al. |
| 2007/0028928 | A1 | 2/2007 | Peyman |
| 2013/0095071 | A1 | 4/2013 | Bance et al. |

FOREIGN PATENT DOCUMENTS

| | | | |
|---|---|---|---|
| JP | 2007-500518 | 1/2007 | |
| WO | WO 2006/110689 | 10/2006 | |
| WO | WO 2011/075838 | 6/2011 | |
| WO | WO 2013/134022 | 9/2013 | |
| WO | WO 2015/054653 | 4/2015 | |
| WO | WO 2015/089462 | 6/2015 | |
| WO | WO-2016131981 A1 * | 8/2016 | ........... A61K 35/761 |
| WO | WO 2018/039375 | 3/2018 | |

OTHER PUBLICATIONS

Office Action in Japanese Appln. No. 2021-196596, dated Dec. 6, 2022, 6 pages (with English translation).

Office Action in Chinese Appln. No. 201680079432.3, dated May 19, 2022, 7 pages (with English translation).

Adachi et al., "Molphy: Programs for Molecular Phylogenetics based on Maximum Likelihood," Tokyo Institute of Statistical Mathematics, 1996, ed.

Akil et al., "Restoration of Hearing in the VGLUT3 Knockout Mouse Using Virally-Mediated Gene Therapy," Neuron, Jul. 2012, 75: 283-293.

Akil et al., "Surgical method for virally mediated gene delivery to the mouse inner ear through the round window membrane," J Vis Exp, 2015, 97: e52187.

Altschul et al., "Gapped Blast and PSI-Blast: A new generation of protein database search programs," Nucleic Acids Res., 1997, 25:3389 3402.

Anisimova and Gascuel, "Approximate likelihood-ratio test for branches: A fast, accurate, and powerful alternative," Systematic Biology, 2006, 55:539-52.

Arnold et al., Novel Slow- and Fast-Type Drug Release Round-Window Microimplants for Local Drug Application to the Cochlea: An Experimental Study in Guinea Pigs, Audiol. Neurootol., 2005, 10:53-63.

Askew et al., "Supplementary Materials for Tmc gene therapy restores auditory function in deaf mice," Sci. Transl. Med, 2015, 7: 295ra108.

Askew et al., "Tmc gene therapy restores auditory function in deaf mice," Sci. Transl. Med, 2015, 7: 295ra108.

(Continued)

*Primary Examiner* — Jane J Zara

(74) *Attorney, Agent, or Firm* — Fish & Richardson P.C.

(57) ABSTRACT

Provided herein are materials and methods for efficiently delivering nucleic acids to cochlear and vestibular cells.

28 Claims, 32 Drawing Sheets

Specification includes a Sequence Listing.

(56) References Cited

OTHER PUBLICATIONS

AU Office Action in Australian Appln. No. 2016366846, dated May 31, 2021, 5 pages.
Ausar et al., "Conformational stability and disassembly of Norwalk virus-like particles. Effect of pH and temperature," J. Biol. Chem., 2006, 281:19478-88.
Balazs et al., "Antibody-based protection against HIV infection by vectored immunoprophylaxis," Nature, 2012, 481:81-4.
Balazs et al., "Broad protection against influenza infection by vectored immunoprphylaxis in mice," Nat. Biotechnol., 2013, 31:647-52.
Boutin et al., 2010, "Prevalence of serum IgG and neutralizing factors against AAV types 1, 2, 5, 6, 8 and 9 in the healthy population: implications for gene therapy using AAV vectors," Hum. Gene Ther., 21:704-12.
Budenz, et al., "Differential effects of AAV.BDNF and AAV.Ntf3 in the deafened adult guinea pig ear," Sci Rep, 2015, 5: 8619.
Calcedo et al. "Worldwide Epidemiology of Neutralizing Antibodies to Adeno-Associated Viruses," J. Infect. Dis., 2009, 199:381-90.
Cao et al., "Phylogenetic relationships among eutherian orders estimated from inferred sequences of mitochondrial proteins: instability of a tree based on a single gene," J. Mol. Evol., 1994, 39:519-27.
Chenna et al., "Multiple sequence alignment with the Clustal series of programs," Nucleic Acids Res., 2003, 31(13):3497-500.
Chien et al., "Cochlear gene transfer mediated by adeno-associated virus: Comparison of two surgical approaches," Laryngoscope, 2015.
Chien et al., "Gene therapy restores hair cell stereocilia morphology in inner ears of deaf whirler mice," Mol Ther, 2016, 24: 17-25.
CN Office Action in Chinese Appln. No. 201680079432.3, dated May 21, 2021, 8 pages (English translation).
Darriba et al., "ProTest3: Fast selection of best-fit models of protein evolution," Bioinformatics, 2011, 27(8): 1164-5.
Dayhoff et al., "A model of Evolutionary Change in Proteins," in Atlas of Protein Sequence and Structure , 1978, pp. 345-352.
Deal et al., "Vectored antibody gene delivery protects against plasmodium falciparum sporozoite challenge in mice," PNAS USA, 2014, 111:12528-32.
Dilwali et al., "Secreted Factors from Human Vestibular Schwannomas Can Cause Cochlear Damage," Scientific Reports, 2015, 5:18599.
Edgar, "Muscle: A multipole swquence alignment method with reduced time and space complexity," BMC Bioinform., 2004, 5:113.
EP Office Action in European Appln. No. 16874069.4, dated Mar. 24, 2020, 5 pages.
Extended European Search Report in Application No. 16874069.4, dated Apr. 15, 2019, 6 pages.
Extended European Search Report in Application No. 21202250.3, dated Mar. 17, 2022, 11 pages.
Felsenstein, "Maximum Likelihood and Minimum-Steps Methods for Estimating Evolutionary Trees from Data on Discrete Characters," Systematic Biology, 1973, 22:240-9.
Fisher et al., "Recombinant adeno-associated virus for muscle directed gene therapy," 1997, Nature Med., 3:306-12.
Fukui & Raphael, "Gene therapy for the inner ear," Hearing Res., 2013, 297:99-105.
Gale et al., FM1-43 dye behaves as a permeant blocker of the hair-cell mechanotransducer channel, J. Neurosci., 2001, 21:7013-25.
Gao et al., "Adeno-associated viruses undergo substantial evolution in primates during natural infections," PNAS, 2003, 100:6081-6.
Gao et al., "Clades of Adeno-associated viruses are widely disseminated in human tissues," J. Virol., 2004, 78:6381-88.
Gao et al., "New recombinant serotypes of AAV vectors," Current Gene Ther., 2005, 5:285-97.
Gascuel, "BioNJ: An improved version of the NJ algorithm based on a simple model of sequence data," Mol. Biol. Evol., 1997, 14:685-95.
Geleoc & Holt, "Sound Strategies for Hearing Restoration," Science, 2014, 344:1241062.
GenBank Accession No. AAC03780.1, "major coat protein VP1 [Adeno-associated virus—2]," Feb. 24, 1998, 1 page.
GenBank Accession No. AAS99264.1, "capsid protein VP1 [Adeno-associated virus 9]," May 25, 2004, 1 page.
Genbank Accession No. AKU89595.1, "capsid protein [Adeno-associated virus]," Aug. 7, 2015, 1 page.
GenBank Accession No. EU368910.1, "Adeno-associated virus isolate AAV6.2 capsid protein VP1 gene, partial cds," Jul. 31, 2008, 1 page.
GenBank Accession No. EU368926, "Adeno-associated virus isolate rh32.33 capsid protein VP1 gene, partial cds," Jul. 31, 2008, 1 page.
Grimm et al., "Helper virus-free, optically controllable, and two-plasmid-based production of adeno-associated virus vectors of serotypes 1 to 6," Mol. Ther., 2003, 7:839:50.
Guinan et al., "Progress in Cochlear Physiology after Békésy," Hearing Res., 2012, 293:12-20.
Guindon and Gascuel, "A simple, fast, and accurate algorithm to estimate large phylogenies by maximum likelihood," Systematic Biology, 2003, 52:696-704.
Guindon et al., "New algorithms and methods to estimate maximum-likelihood phylogenies: assessing the performance of PhyML 3.0," System. Biol., 2010, 59:307-21.
Henikoff and Henikoff, "Amino acid substitution matrices from protein blocks," PNAS, 1992, 89:10915-9.
International Preliminary Report on Patentability in International Application No. PCT/US2016/031218, mailed on Nov. 16, 2017, 7 pages.
International Preliminary Report on Patentability in International Application No. PCT/US2016/044819, mailed on Feb. 8, 2018, 5 pages.
International Preliminary Report on Patentability in International Application No. PCT/US2016/066225, dated Jun. 12, 2018, 11 pages.
International Search Report and Written Opinion in Application No. PCT/US2016/066255, mailed on Apr. 13, 2017, 16 pages.
International Search Report and Written Opinion in International Application No. PCT/US2014/060163, mailed on Jul. 13, 2015, 19 pages.
International Search Report and Written Opinion in International Application No. PCT/US2016/031218, mailed on Aug. 8, 2016, 12 pages.
International Search Report and Written Opinion in International Application No. PCT/US2016/044819, mailed on Oct. 31, 2016, 5 pages.
Jones et al., "The rapid generation of mutation data matrices from protein sequences," 1992, Comp. Appl. Biosci., 8:275-82.
JP Office Action in JP Appln. No. 2018-529927, dated Oct. 6, 2020, 8 pages (with English translation).
Katoh et al., "MAFFT version 5: Improvement in accuracy of multiple sequence alignment," Nuc. Acids Res., 2005, 33:511-8.
Kawashima et al., "Mechanotransduction in mouse inner ear hair cells requires transmembrane channel-like genes," J. Clin. Invest., 2011, 121:4796-809.
Kesser et al., "An in vitro model system to study gene therapy in the human inner ear," Gene Ther., 2007, 14:1121-1131.
Kilpatrick et al., "Adeno-associated virus-mediated gene delivery into the scala media of the normal and deafened adult mouse ear," Gene Ther, 2011, 18: 569-578.
Konishi et al., "Gene transfer into guinea pig cochlea using adeno-associated virus vectors," J Gene Med, 2008, 10: 610-618.
Lassmann et al., "Kalign, Kalignvu and Mumsa: Web servers for multiple sequence alignment," Nuc. Acids Res., 2006, 34:W596-99.
Lentz et al., "Deafness and retinal degeneration in a novel USHIC knock-in mouse model," Dev., Neurobiol., 2010, 70:253-67.
Limberis et al., "Intranasal antibody gene transfer in mice and ferrets elicits broad protection against pandemic influenza," Sci. Transl. Med., 2013, 5:187ra72.
Liu et al., "Specific and efficient transduction of Cochlear inner hair cells with recombinant adeno-associated virus type 3 vector," Mol Ther, 2005, 12: 725-733.

(56) References Cited

OTHER PUBLICATIONS

Lock et al., "Rapid, simple, and versatile manufacturing of recombinant adeno-associated viral vectors at scale," Hum. Gene Ther., 2010, 21:1259-71.
Loytynoja et al., "An Algorithm for progressive multiple alignment of sequences with insertions," PNAS USA, 2005, 102:10557-62.
Loytynoja et al., "Phylogeny-Aware Gap Placement Prevents Errors in Sequence Alignment and Evolutionary Analysis," Science, 2008, 320:1632-5.
Luebke et al., "Adenoviral and AAV-mediated gene transfer to the inner ear: role of serotype, promoter, and viral load on in vivo and in vitro infection efficiencies," Adv Otorhinolaryngol, 2009, 66: 87-98.
Lui & Duff, "A Technique for Serial Collection of Cerebrospinal Fluid from the Cisterna Magna in Mouse," J. Visualized Exp., 2008, 21:e960.
Maison et al., "Muscarinic signaling in the cochlea: presynaptic and postsynaptic effects on efferent feedback and afferent excitability," J. Neurosci., 2010, 30:6751-62.
Manning et al., "Transient immunosuppression allows transgene expression following readministration of adeno-associated viral vectors," 1998, Human Gene Ther., 9:477-85.
Mao et al., "Persistent Suppression of Ocular Neovascularization with intravitreal administration of AAVrh.10 coding for Bevacizumab," Hum. Gene Ther., 2011, 22:1525-35.
Mathur & Yang, "Usher syndrome: hearing loss, retinal degeneration and associated abnormalities," Biochim. Biophys. Acta, 2015, 1852:406-20.
Meyers et al., "Lighting up the senses: FM1-43 loading of sensory cells through nonselective ion channels," J. Neurosci., 2003, 23:4054-65.
Nakai et al., "A limited number of transducible hepatocytes restricts a wide-range linear vector dose response in recombinant adeno-associated virus-mediated liver transduction," J. Virol., 2002, 76:11343-9.
Nakai et al., "Unrestricted hepatocyte transduction with adeno-associated virus serotype 8 vectors in mice," J. Virol., 2005, 79:214-24.
Notredame et al., "T-Coffee: A novel method for fast and accurate multiple sequence alignment," J. Mol. Biol., 2000, 302:205-17.
Office Action in Australian Appln. No. 2016366846, dated Mar. 8, 2022, 4 pages.
Office Action in Chinese Appln. No. 201680079432.3, dated Dec. 16, 2021, 13 pages (with English translation).
Parker & Bitner-Glindzicz, "Genetic investigations in childhood deafness," Arch. Dis. Childhood, 2015, 100:271-8.
Paul et al., "Determination of hepatitis E virus seroprevalence by using recombinant fusion proteins and synthetic peptides," 1994, J. Infect. Dis., 169:801-6.
Pettersen et al., "UCSF Chimera—a visualization system for exploratory research and analysis," 2004, J. Comp. Chem., 25:1605-12.
Reeves, "Heterogeneity in the substitution process of amino acid sites of proteins coded for by mitochondrial DNA," 1992, J. Mol. Evol., 35:17-31.
Sakhria et al., "Co-Circulation of Toscana Virus and Punique Virus in Northern Tunisia: A microneutralisation-based seroprevalence study," PLOS Negl. Trop. Dis., 2013, 7:e2429.
Sauerbrei et al. "Seroprevalence of herpes simplex virus type 1 and type 2 in Thuringia, Germany, 1999 to 2006," Euro Survell., 2011 , 16(44):3).
Schneider et al., "Empirical codon substitution matrix," BMC Bioinform., 2005, 6:134.
Schwarz, "Estimating the Dimension of a Model," Ann. Statist. 1978, 6:461-4.
Sergeyenko et al., "Age-related cochlear synaptopathy: an early-onset contributor to auditory functional decline," J. Neurosci., 2013, 33:13686-94.
SG Search Report and Written Opinion in Singapore Appln. No. 11201804814Y, dated Sep. 20, 2019, 10 pages.
SG Search Report and Written Opinion in Singapore Appln. No. 11201804814Y, dated Jan. 27, 2021, 6 pages.
Stone et al., "Adeno-associated virus-mediated gene transfer to hair cells and support cells of the murine cochlea," Mol Ther, 2005, 11: 843-848.
Stupay et al., "Optimization of Clarin-1 AAV Gene Delivery Vectors to the Mouse Retina," ARVO Annual Meeting Abstract, Apr. 2014, URL:https://iovs.arvojournal s.org/article.
Thompson et al., "Clustal W: improving the sensitivity of progressive multiple sequence alignment through sequence weighting, position-specific gap penalties and weight matrix choice," Nuc. Acids Res., 1994, 22:4673-90.
Wang et al., "Systematic Evaluation of AAV Vectors for Liver directed Gene Transfer in Murine Models," Mol. Ther., 2010, 18:118-25.
Wang et al., "Early postnatal virus inoculation into the scala media achieved extensive expression of exogenous green fluorescent protein in the inner ear and preserved auditory brainstem response thresholds," J Gene Med, 2013, 15: 123-133.
Wang et al., "Efficient cochlear gene transfection in guinea-pigs with adeno-associated viral vectors by partial digestion of round window membrane," Gene Ther, 2012, 19: 255-263.
Watanabe et al., "AAVrh 10-mediated genetic delivery of bevacizumab to the pleura to provide local anti-VEGF to suppress growth of metastatic lung tumors," Gene Ther., 2010, 17:1042-51.
Whelan et al., "A general empirical model of protein evolution derived from multiple protein families using a maximum-likelihood approach," Mol. Biol. Evol., 2001, 18:691-9.
Xia et al., "Inner ear gene transfection in neonatal mice using adeno-associated viral vector: a comparison of two approaches," PLoS One, 2012, 7: e43218.
Xie et al., "AAV-mediated persistent bevacizumab therapy suppresses tumor growth of ovarian cancer," Gynecol. Oncol, 2014, 135: 325-32.
Xu et al., "Seroprevalence of herpes simplex virus types 1 and 2 in pregnant women in the United States," Am. J. Obstet. Gynecol., 2007, 196:43.e1-6.
Yang, "PAML 4: phylogenetic analysis by maximum likelihood," Mol. Biol. Evol., 2007, 24:1586-91.
Yang, "Maximum-likelihood estimation of phylogeny from DNA sequences when substitution rates differ over sites," Mol. Biol. Evol., 1993, 10:1396-1401.
Yang, "PAML: A program package for phylogenetic analysis by maximum likelihood," Comp. Applic. BioSci., 1997, 13:555-6.
Yu et al., "Virally-expressed connexin26 restores gap junction function in the cochlea of conditional Gjb2 knockout mice," Gene Ther, 2014, 21: 71-80.
Zheng et al., "Targeting of the Hair Cell Proteins Cadherin 23, Harmonin, Myosin XVa, Espin and Prestin in an Epithelial Cell Model," J. Neurosci., 2010, 30:7187-201.
Zinn et al., "In Silico Reconstruction of the Viral Evolutionary Lineage Yields a Potent Gene Therapy Vector," Cell Reports, Aug. 2015, 12:1056-68.
Office Action in Canadian Appln. No. 3,007,476, dated Jan. 31, 2023, 5 pages.
Kurima et al., "TMC1 and TMC2 Localize at the Site of Mechanotransduction in Mammalian Inner Ear Hair Cell Stereocilia," Cell Rep., Sep. 2015, 12(10):1606-1617.
Le Quesne Stabej et al., "Comprehensive sequence analysis of nine Usher syndrome genes in the UK National Collaborative Usher Study," J. Med. Genet., Jan. 2012, 49(1):27-36.
Office Action in Canadian Appln. No. 3,007,476, dated Mar. 13, 2024, 5 pages.
Office Action in Japanese Appln. No. 2023-110371, dated Jul. 23, 2024, 6 pages (with English translation).
Office Action in Korean Appln. No. 10-2018-7019786, dated Jun. 18, 2024, 9 pages (with English translation).

* cited by examiner

| Anc80 NAB | Serum | CSF |
|---|---|---|
| Un-injected | <1/4 | 1/16 - 1/128 |
| Injected | <1/52.5 | <1/52.5 |

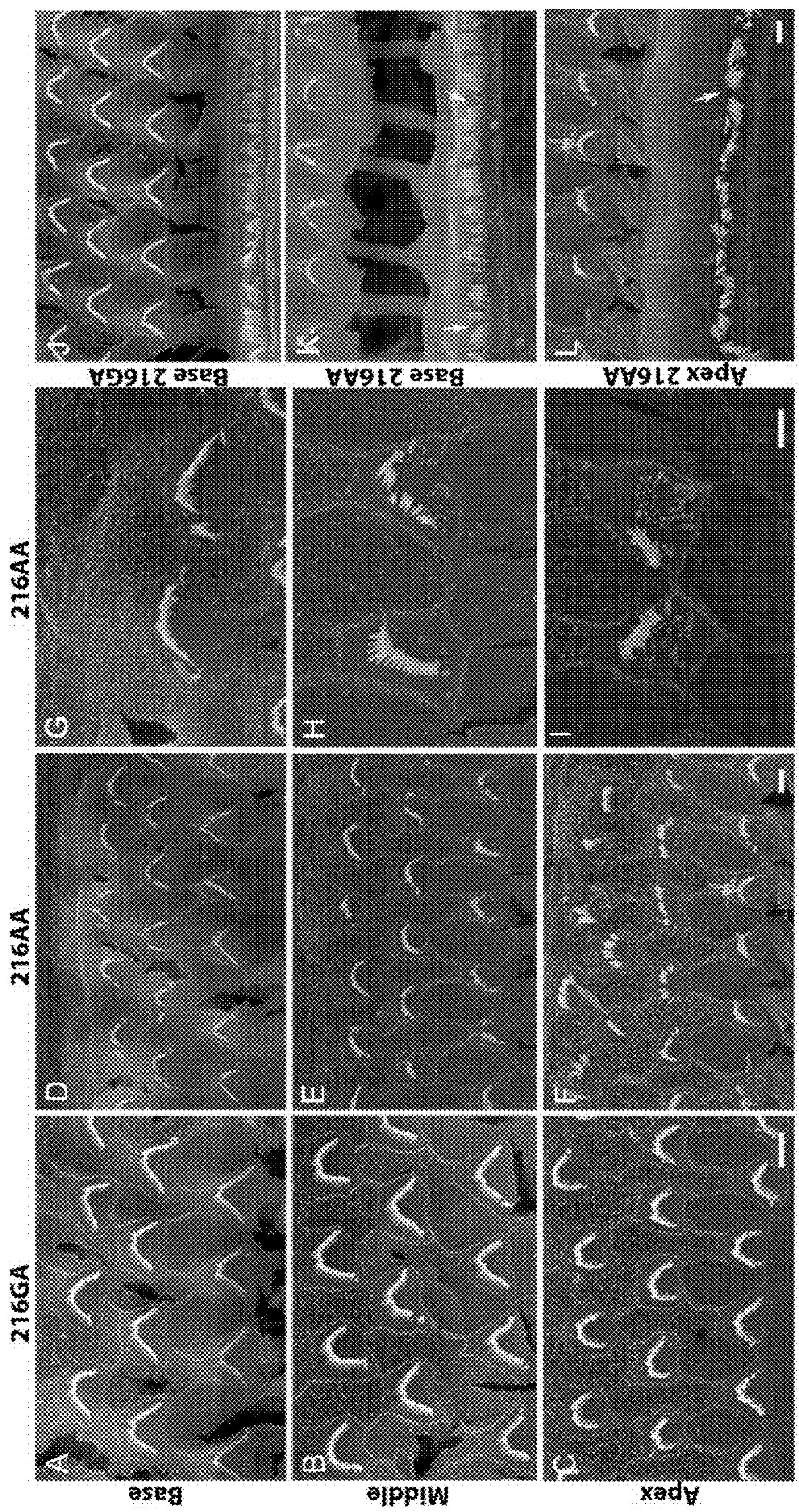
FIGs. 19A-L

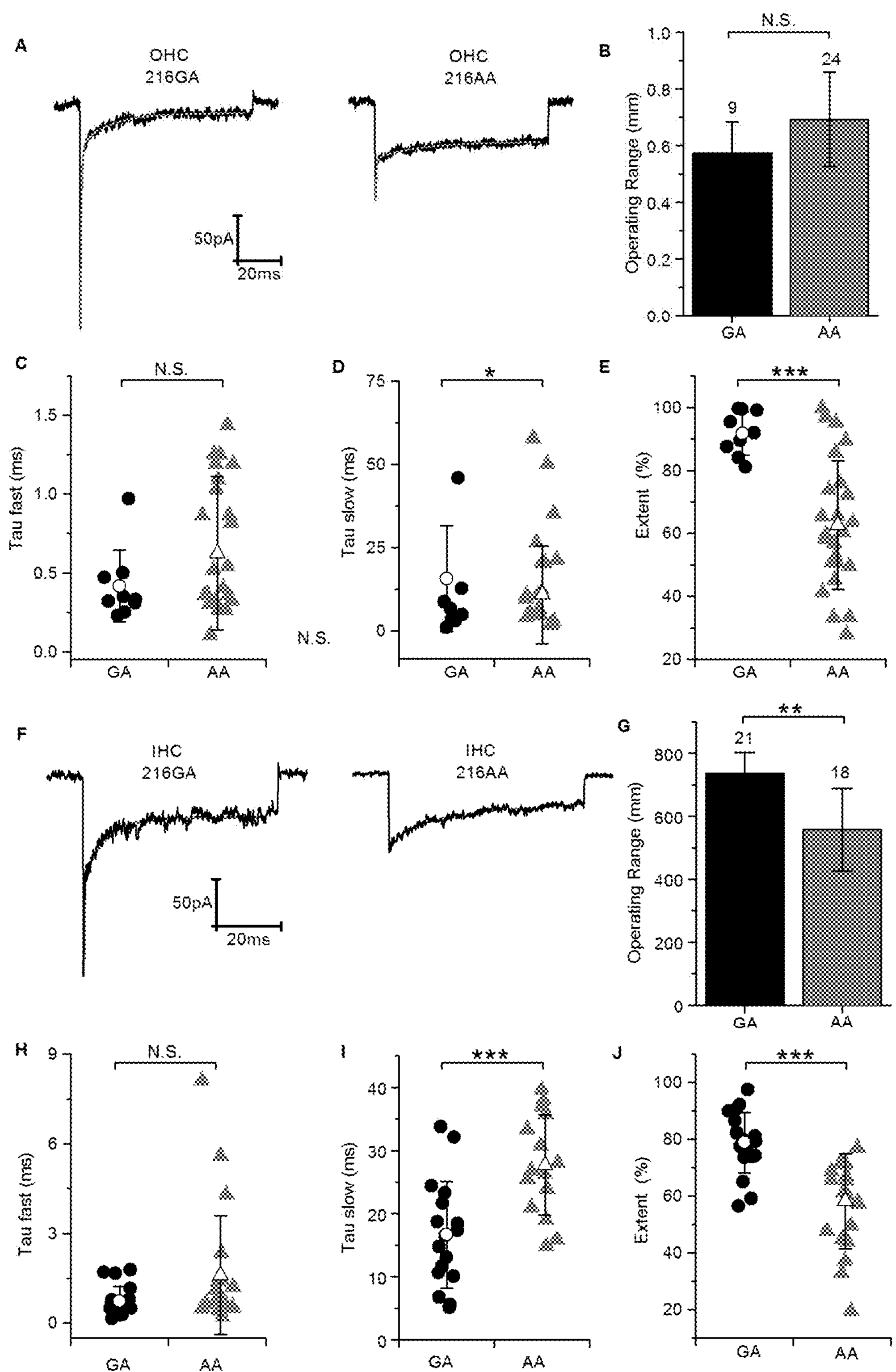
FIGs. 20A-J

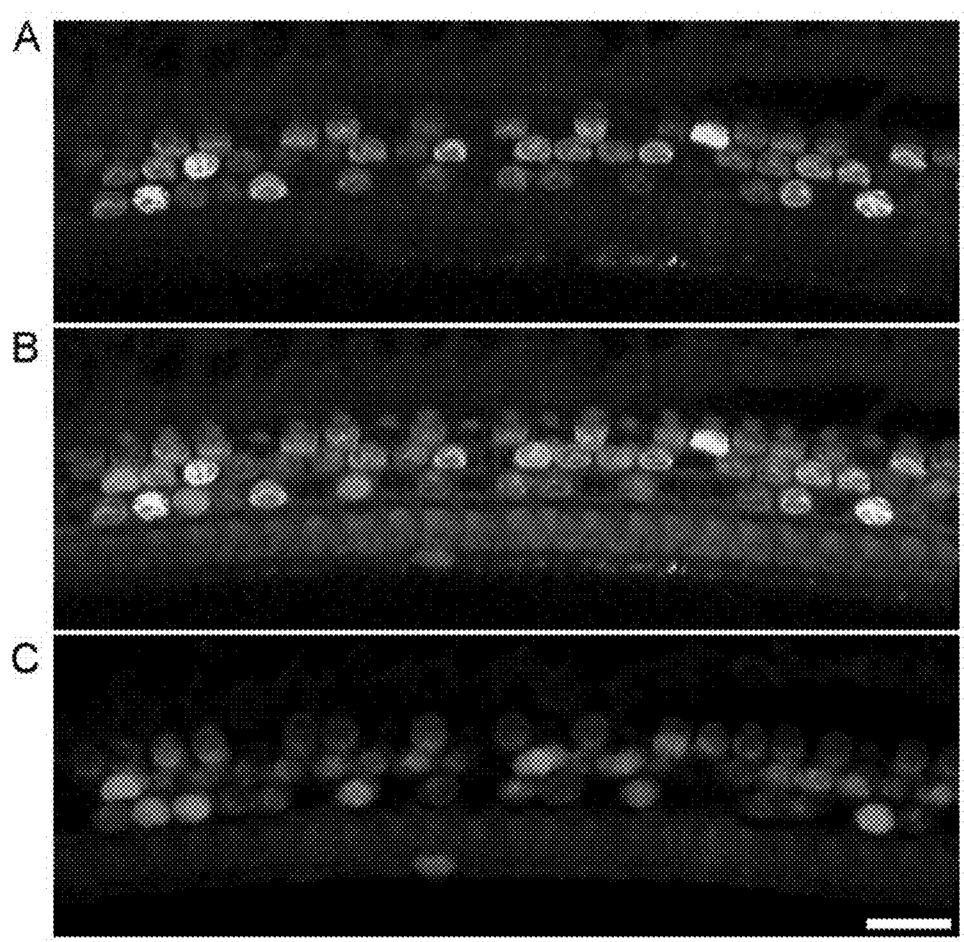
FIGs. 21A-C

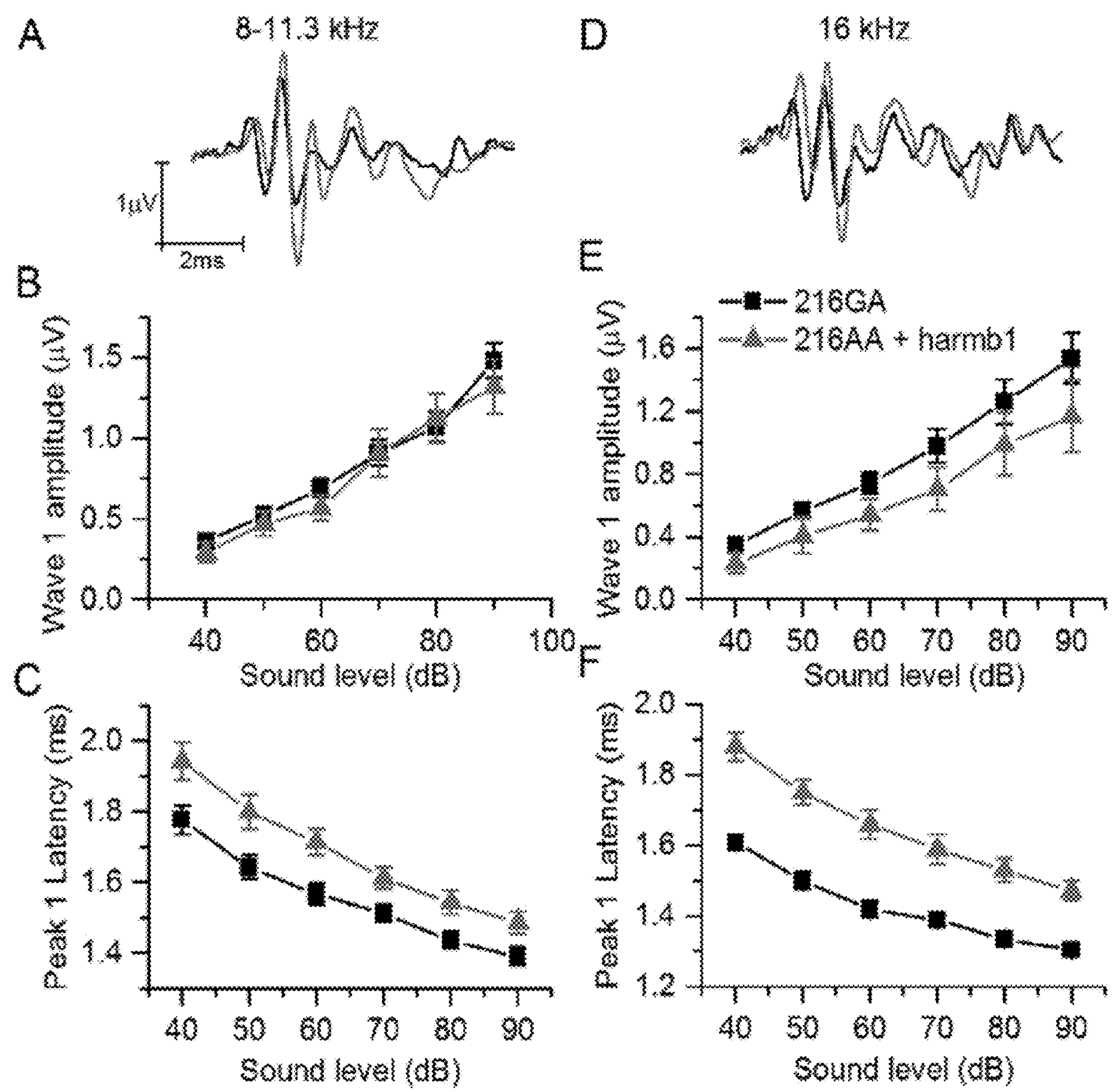
FIGs. 22A-F

Figure 23A:
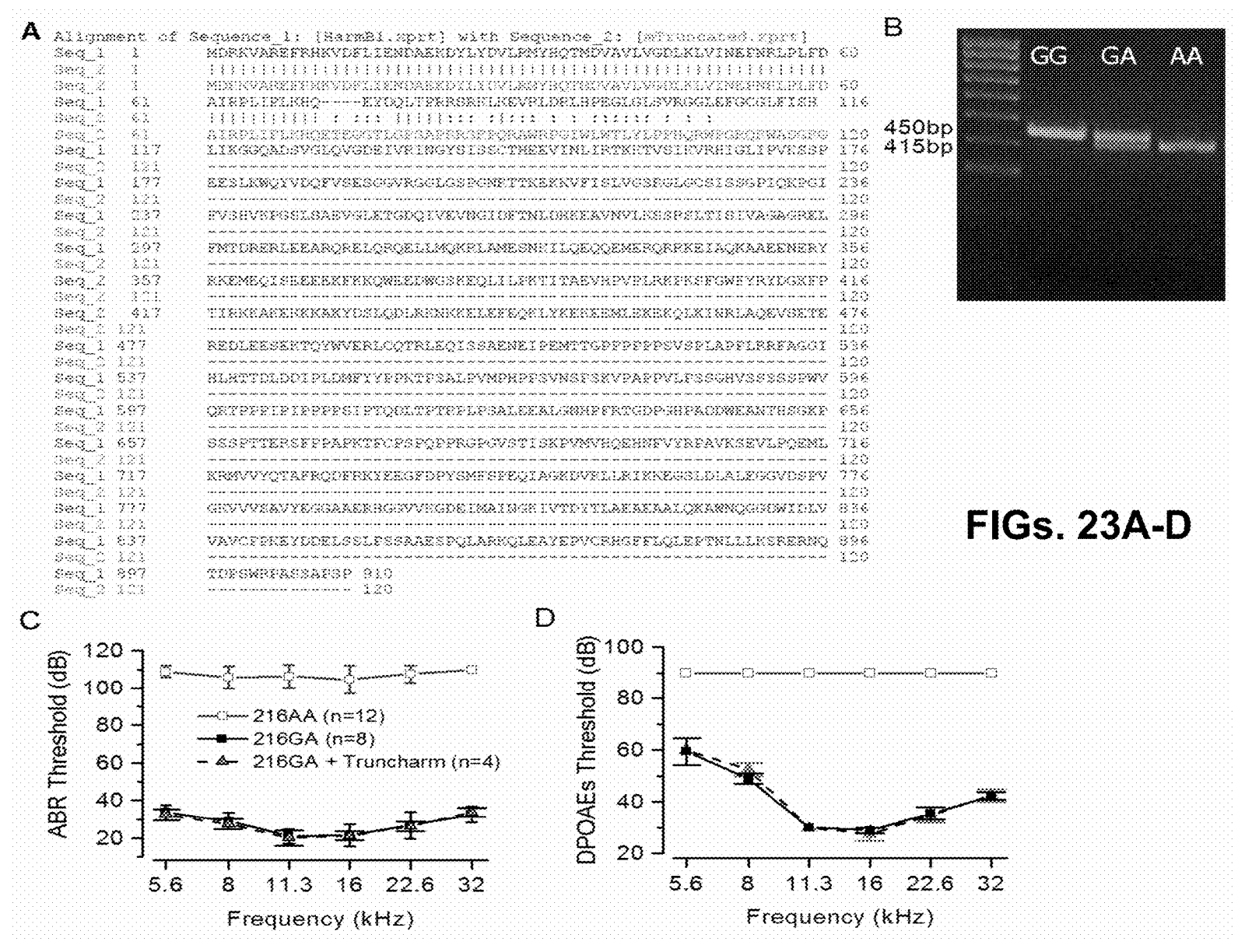

A

B

GG GA AA

450bp
415bp

C

ABR Threshold (dB)

120 100 80 60 40 20

216AA (n=12)
216GA (n=8)
216GA + Truncharm (n=4)

5.6 8 11.3 16 22.6 32

Frequency (kHz)

D

DPOAEs Threshold (dB)

100 80 60 40 20

5.6 8 11.3 16 22.6 32

Frequency (kHz)

FIGs. 23A-D

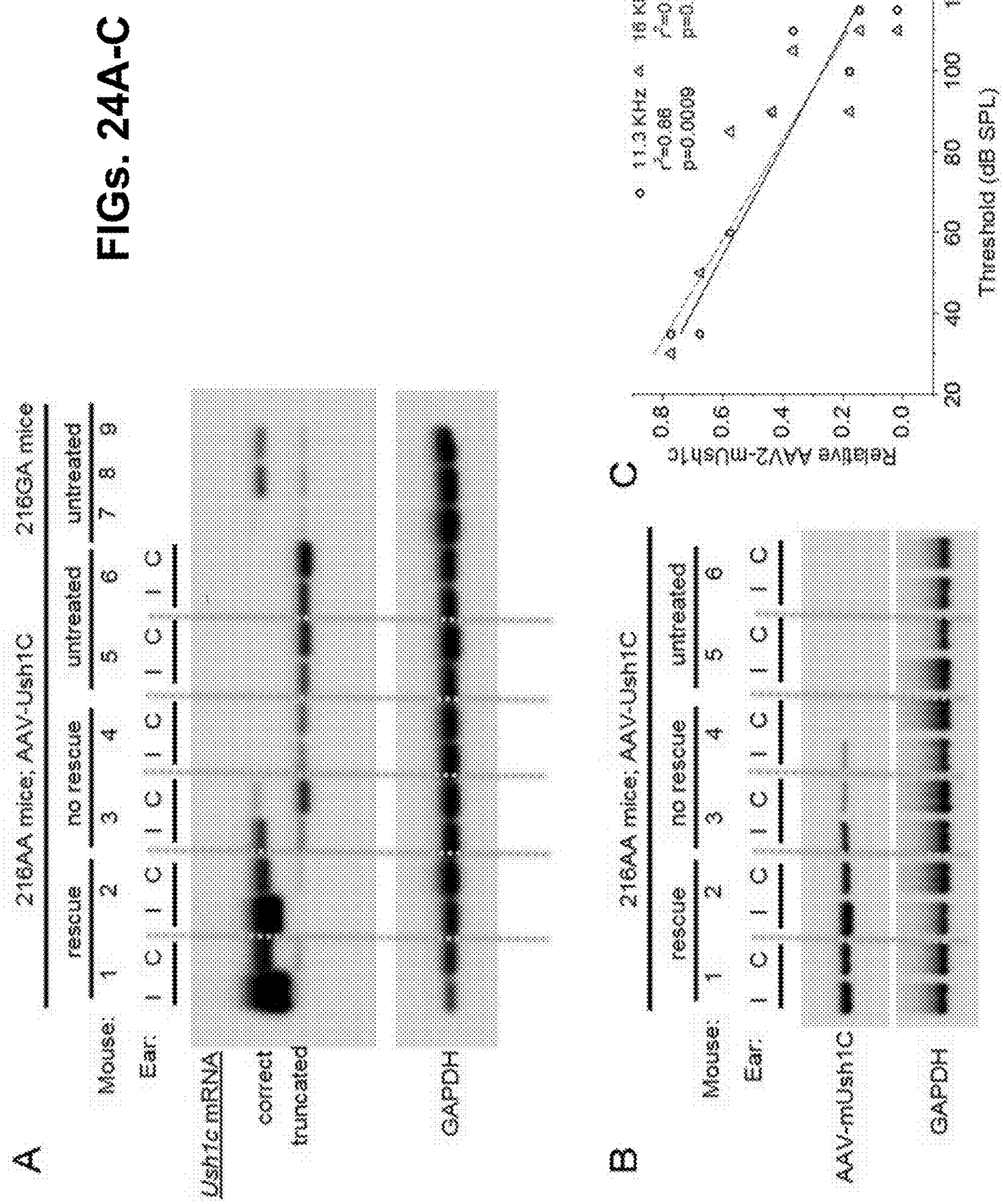
FIGs. 24A-C
A
Mouse:
Ear:
216AA mice; AAV-Ush1C
216GA mice
rescue
no rescue
untreated
untreated
1 2 3 4 5 6 7 8 9
I C I C I C I C I C I C
Ush1c mRNA
correct
truncated
GAPDH
B
216AA mice; AAV-Ush1C
rescue
no rescue
untreated
1 2 3 4 5 6
AAV-mUsh1C
GAPDH
C
Relative AAV2-mUsh1c
0.0 0.2 0.4 0.6 0.8
20 40 60 80 100 120
Threshold (dB SPL)
11.3 KHz
$r^2$=0.88
p=0.0009
16 KHz
$r^2$=0.75
p=0.005

FIGs. 26A-D

A
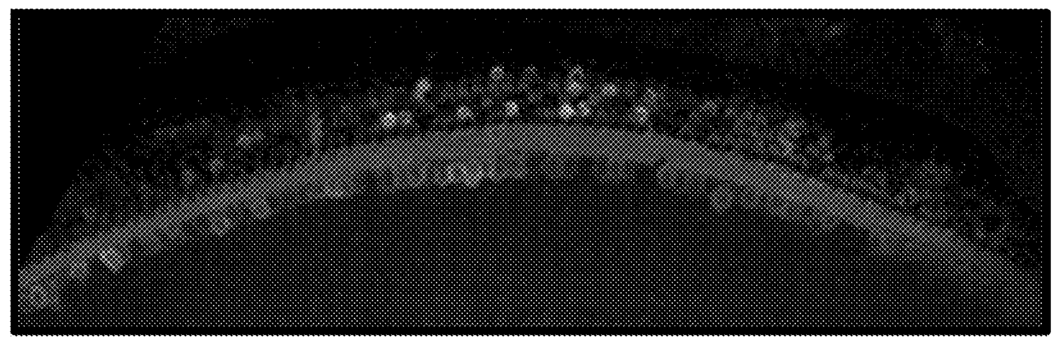
B
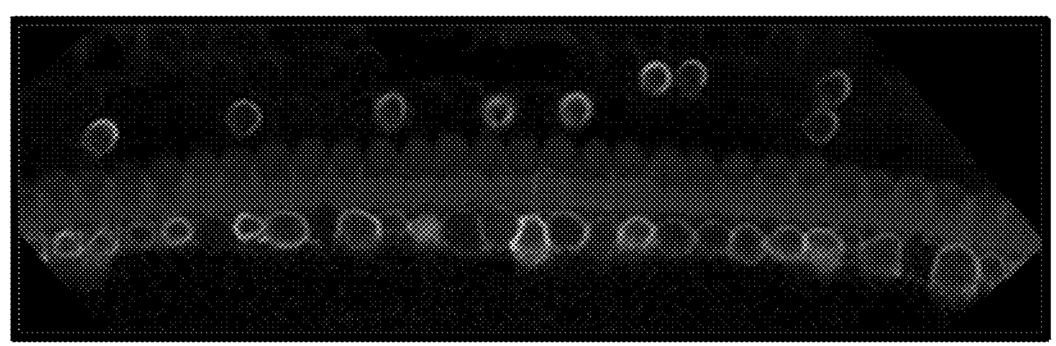
C
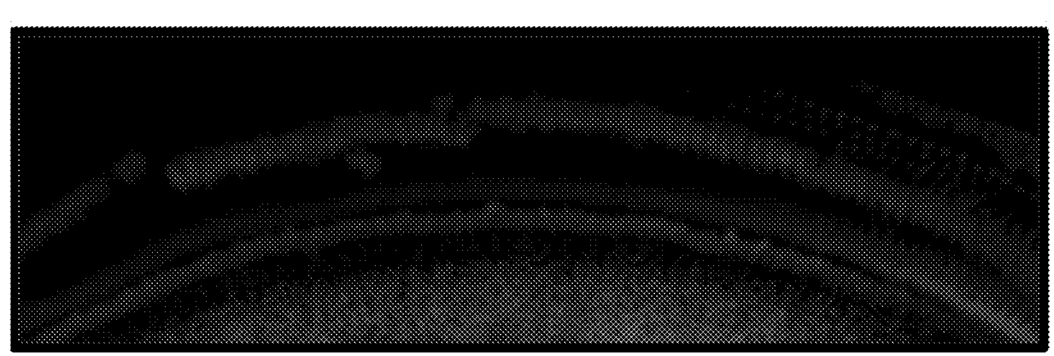
FIGs. 28A-C

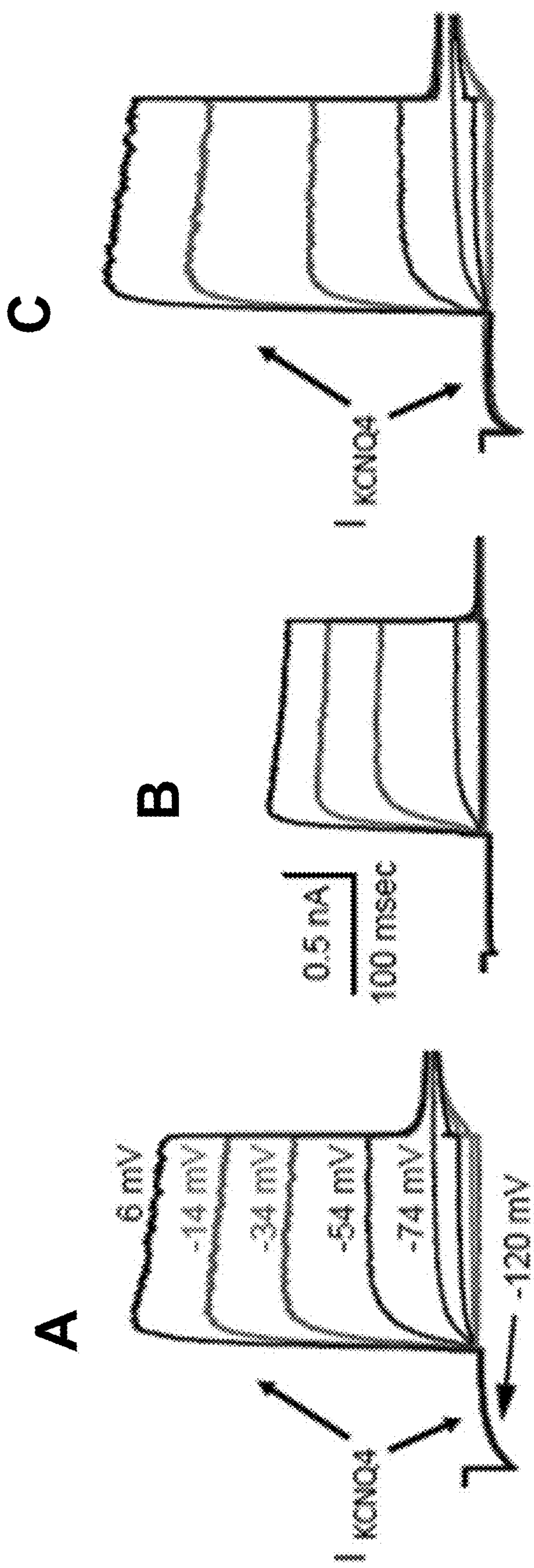
FIGs. 29A-C

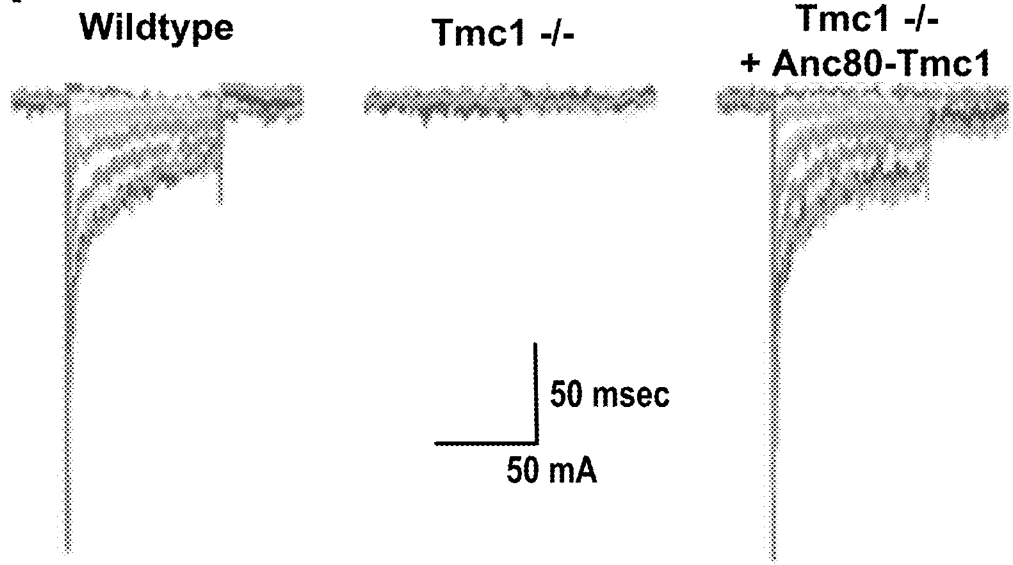
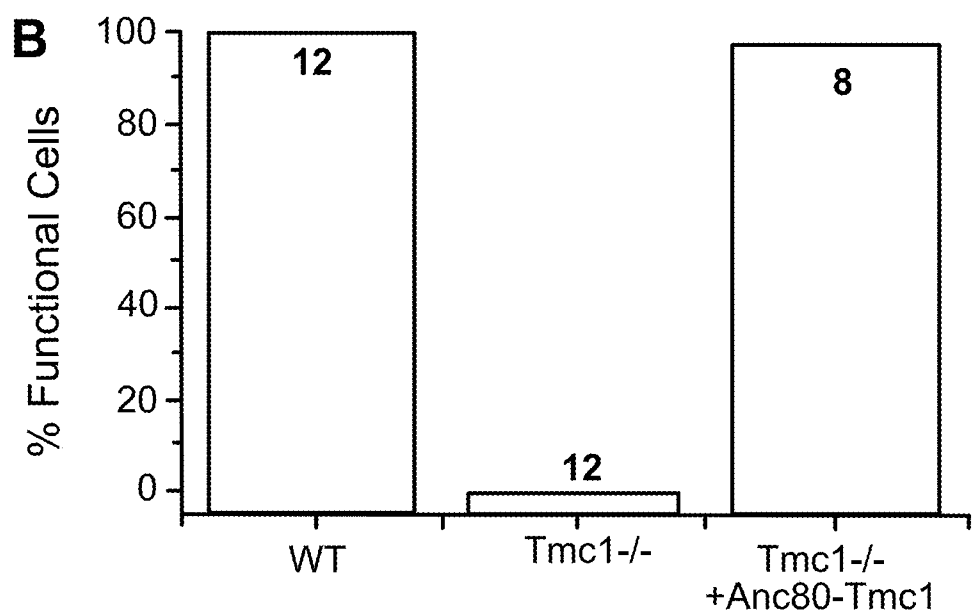
FIGs. 31A-B

SEQUENCE LISTING

```
<160> NUMBER OF SEQ ID NOS: 20

<210> SEQ ID NO 1
<211> LENGTH: 736
<212> TYPE: PRT
<213> ORGANISM: Artificial Sequence
<220> FEATURE:
<223> OTHER INFORMATION: synthetic viral capsid protein
<220> FEATURE:
<221> NAME/KEY: misc_feature
<222> LOCATION: (168)..(168)
<223> OTHER INFORMATION: Xaa can be any naturally occurring amino acid
<220> FEATURE:
<221> NAME/KEY: misc_feature
<222> LOCATION: (204)..(204)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (311)..(311)
<223> OTHER INFORMATION: Xaa can be any naturally occurring amino acid
<220> FEATURE:
<221> NAME/KEY: misc_feature
<222> LOCATION: (411)..(411)
<223> OTHER INFORMATION: Xaa can be any naturally occurring amino acid
<220> FEATURE:
<221> NAME/KEY: misc_feature
<222> LOCATION: (460)..(460)
<223> OTHER INFORMATION: Xaa can be any naturally occurring amino acid
<220> FEATURE:
<221> NAME/KEY: misc_feature
<222> LOCATION: (493)..(493)
<223> OTHER INFORMATION: Xaa can be any naturally occurring amino acid
<220> FEATURE:
<221> NAME/KEY: misc_feature
```

```
<222> LOCATION: (562)..(562)
<223> OTHER INFORMATION: Xaa can be any naturally occurring amino acid
<220> FEATURE:
<221> NAME/KEY: misc_feature
<222> LOCATION: (576)..(576)
<223> OTHER INFORMATION: Xaa can be any naturally occurring amino acid
<220> FEATURE:
<221> NAME/KEY: misc_feature
<222> LOCATION: (587)..(587)
<223> OTHER INFORMATION: Xaa can be any naturally occurring amino acid
<220> FEATURE:
<221> NAME/KEY: misc_feature
<222> LOCATION: (609)..(609)
<223> OTHER INFORMATION: Xaa can be any naturally occurring amino acid

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Xaa Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Xaa Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Xaa Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Xaa Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335
```

```
Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Xaa Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Xaa Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Xaa Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Xaa Glu Glu Glu Ile Lys Thr Thr Asn Pro Val Ala Thr Glu Xaa
                565                 570                 575

Tyr Gly Thr Val Ala Thr Asn Leu Gln Ser Xaa Asn Thr Ala Pro Ala
            580                 585                 590

Thr Gly Thr Val Asn Ser Gln Gly Ala Leu Pro Gly Met Val Trp Gln
        595                 600                 605

Xaa Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

<210> SEQ ID NO 2
<211> LENGTH: 736

<212> TYPE: PRT
<213> ORGANISM: Artificial Sequence
<220> FEATURE:
<223> OTHER INFORMATION: synthetic viral capsid protein

<400> SEQUENCE: 2

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Lys Gly Gln Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Ser Gly Val Gly Ser Asn Thr Met Ala Ala Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Gly Ser Thr Asn Asp Asn Thr
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Lys Leu Asn Phe Lys Leu Phe Asn Ile Gln
305                 310                 315                 320

Val Lys Glu Val Thr Thr Asn Asp Gly Thr Thr Thr Ile Ala Asn Asn
                325                 330                 335

Leu Thr Ser Thr Val Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380
```

```
Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Ser Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Ser Gly Thr Ala Gly Asn Arg Thr Leu Gln Phe Ser
    450                 455                 460

Gln Ala Gly Pro Ser Ser Met Ala Asn Gln Ala Lys Asn Trp Leu Pro
465                 470                 475                 480

Gly Pro Cys Tyr Arg Gln Gln Arg Val Ser Lys Thr Thr Asn Gln Asn
                485                 490                 495

Asn Asn Ser Asn Phe Ala Trp Thr Gly Ala Thr Lys Tyr His Leu Asn
            500                 505                 510

Gly Arg Asp Ser Leu Val Asn Pro Gly Pro Ala Met Ala Thr His Lys
        515                 520                 525

Asp Asp Glu Asp Lys Phe Phe Pro Met Ser Gly Val Leu Ile Phe Gly
    530                 535                 540

Lys Gln Gly Ala Gly Asn Ser Asn Val Asp Leu Asp Asn Val Met Ile
545                 550                 555                 560

Thr Asn Glu Glu Glu Ile Lys Thr Thr Asn Pro Val Ala Thr Glu Glu
                565                 570                 575

Tyr Gly Thr Val Ala Thr Asn Leu Gln Ser Ala Asn Thr Ala Pro Ala
            580                 585                 590

Thr Gly Thr Val Asn Ser Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Leu Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Thr Asn Val Asp Phe Ala Val Asp Thr Asn Gly Val
705                 710                 715                 720

Tyr Ser Glu Pro Arg Pro Ile Gly Thr Arg Tyr Leu Thr Arg Asn Leu
                725                 730                 735
```

```
<210> SEQ ID NO 3
<211> LENGTH: 7064
<212> TYPE: DNA
<213> ORGANISM: Artificial Sequence
<220> FEATURE:
<223> OTHER INFORMATION: synthetic expression construct

<400> SEQUENCE: 3

ctgcgcgctc gctcgctcac tgaggccgcc cgggcaaagc ccgggcgtcg ggcgaccttt      60

ggtcgcccgg cctcagtgag cgagcgagcg cgcagagagg gagtggccaa ctccatcact     120
```

```
aggggttcct tgtagttaat gattaacccg ccatgctact tatctacgta gccatgctct    180
aggaagatcg gaattcgccc ttaagctagc tagttattaa tagtaatcaa ttacggggtc    240
attagttcat agcccatata tggagttccg cgttacataa cttacggtaa atggcccgcc    300
tggctgaccg cccaacgacc cccgcccatt gacgtcaata atgacgtatg ttcccatagt    360
aacgccaata gggactttcc attgacgtca atgggtggag tatttacggt aaactgccca    420
cttggcagta catcaagtgt atcatatgcc aagtacgccc cctattgacg tcaatgacgg    480
taaatggccc gcctggcatt atgcccagta catgacctta tgggactttc ctacttggca    540
gtacatctac gtattagtca tcgctattac catggtgatg cggttttggc agtacatcaa    600
tgggcgtgga tagcggtttg actcacgggg atttccaagt ctccacccca ttgacgtcaa    660
tgggagtttg ttttggcacc aaaatcaacg ggactttcca aaatgtcgta acaactccgc    720
cccattgacg caaatgggcg gtaggcgtgt acggtgggag gtctatataa gcagagctgg    780
tttagtgaac cgtcagatcc tgcagaagtt ggtcgtgagg cactgggcag gtaagtatca    840
aggttacaag acaggtttaa ggagaccaat agaaactggg cttgtcgaga cagagaagac    900
tcttgcgttt ctgataggca cctattggtc ttactgacat ccactttgcc tttctctcca    960
caggtgtcca ggcggccgcg gatgccaccc aaaaaagtgc aaatccaagt ggaggagaaa   1020
gaagaggata cagaggaaag ctcaagtgaa gaagaagaag ataagctacc cagaagagag   1080
agcttgagac caaagaggaa acggaccaga gatgtcatca atgaggatga cccagaaccg   1140
gagccggagg atgaagaaac aagaaaggca agagaaaaag aaaggcggag gaggctgcgg   1200
agaggagcgg aagaagaaga agaaattgat gaagaggaat tagaacggtt aaaagcactg   1260
ctcgatgaga atagacaaat gatcgctact gtcaaatgta aaccttggaa aatggagaag   1320
aaaattgaag ttctcaagga agcaaagaaa tttgtgagtg agaatgaagg cgctcttggg   1380
aaaggaaagg gaaagaagtg gtttgcattt aagatgatga tggccaagaa atgggcaaaa   1440
ttcctccgag attttgagaa cttcaaagcg gcttgcgtcc catgggaaaa caaaatcaag   1500
gcaattgaaa gtcagtttgg ttcctcagtg gcctcgtact tcctgttcct caggtggatg   1560
tacggcgtca acatggttct ctttgtgttg accttcagcc tcatcatgtt accggagtac   1620
ctctggggtt taccgtacgg cagcttacct aggaaaacag tcccaagagc tgaagaagca   1680
tctgcagcca actttggtgt gttgtatgac ttcaatggcc tggcgcagta ctctgtcctc   1740
ttttatggct attacgacaa taaacgcacg atcggatggc tgaatttccg gctacctctt   1800
tcctacttcc tggtggggat tatgtgcatt ggatacagct tcctggttgt cctcaaagcg   1860
atgaccaaaa atattggtga cgatggtggt ggcgatgaca acactttcaa cttcagctgg   1920
aaggtgttct gtagctggga ctatctgatt ggtaaccctg aaacagccga caacaagttt   1980
aactctatca cgatgaactt taaggaagcc atcatagaag agagagccgc acaggtggag   2040
gagaacatcc acctcatcag atttctgagg tttctcgcta acttcttcgt gttcctcaca   2100
cttggtgcaa gtggatacct catcttttgg gctgtgaagc gatcccagga gttcgcccag   2160
caagatcctg acacccttgg gtggtgggaa aaaaatgaaa tgaacatggt aatgtccctc   2220
ctggggatgt tctgtcccac cctgtttgac ttatttgctg aactggaaga ttaccatcct   2280
ctcattgctc tgaagtggct cctggggcgc atttttgctc ttcttctagg caacttgtat   2340
gtattcattc tcgccttgat ggatgagatt aacaacaaga ttgaagagga gaagcttgtg   2400
aaggccaata ttaccctgtg ggaagccaac atgattaagg cttacaatga atctctctct   2460
```

-continued

```
gggctctctg ggaacaccac aggagcaccc tttttcgttc atcctgcaga tgtccctcgc   2520
ggtccctgct gggaaacaat ggtggggcag gaattcgtgc gtctcaccgt ttctgacgtc   2580
ctgaccactt acgtcacgat cctcattggc gacttcctca gagcatgttt cgtgaggttc   2640
tgcaattact gctggtgctg ggacttagaa tatggatatc cttcatacac agaattcgac   2700
atcagtggca acgtcctcgc tctgatcttc aaccaaggca tgatctggat gggctccttc   2760
ttcgctccta gcctcccggg catcaacatc ctccgtctcc acacatccat gtatttccag   2820
tgctgggctg tgatgtgctg caatgttccc gaggccaggg tgttcaaagc ttccagatcc   2880
aacaacttct acctcggcat gctgctactc atcctcttcc tgtccaccat gccggtcctg   2940
tacatgatcg tctccctccc gccatctttt gattgtgggc ccttcagtgg taaaaacagg   3000
atgtttgaag tcatcggtga gaccctggaa catgacttcc caagctggat ggcgaagatc   3060
ctgaggcagc tttctaaccc cggccttgtc attgctgtca ttctggtgat ggttctgacc   3120
atctattatc tcaatgctac tgccaagggc cagaaagcag cgaatctgga cctcaaaaag   3180
aagatgaaac agcaagcttt ggagaacaaa atgcgaaaca agaaaatggc agcggctcga   3240
gcagctgcag ctgctggtgg ccagtaagga tccaatcaac ctctggatta caaaatttgt   3300
gaaagattga ctggtattct taactatgtt gctcctttta cgctatgtgg atacgctgct   3360
ttaatgcctt tgtatcatgc tattgcttcc cgtatggctt tcattttctc ctccttgtat   3420
aaatcctggt tgctgtctct ttatgaggag ttgtggcccg ttgtcaggca acgtggcgtg   3480
gtgtgcactg tgtttgctga cgcaaccccc actggttggg gcattgccac cacctgtcag   3540
ctcctttccg ggactttcgc tttccccctc cctattgcca cggcggaact catcgccgcc   3600
tgccttgccc gctgctggac aggggctcgg ctgttgggca ctgacaattc cgtggtgttg   3660
tcggggaaat catcgtcctt tccttggctg ctcgcctgtg ttgccacctg gattctgcgc   3720
gggacgtcct tctgctacgt cccttcggcc ctcaatccag cggaccttcc ttcccgcggc   3780
ctgctgccgg ctctgcggcc tcttccgcgt cttcgagatc tgcctcgact gtgccttcta   3840
gttgccagcc atctgttgtt tgcccctccc ccgtgccttc cttgaccctg gaaggtgcca   3900
ctcccactgt cctttcctaa taaaatgagg aaattgcatc gcattgtctg agtaggtgtc   3960
attctattct ggggggtggg gtggggcagg acagcaaggg ggaggattgg gaagacaata   4020
gcaggcatgc tggggactcg agttaagggc gaattcccga taaggatctt cctagagcat   4080
ggctacgtag ataagtagca tggcgggtta atcattaact acaaggaacc cctagtgatg   4140
gagttggcca ctccctctct gcgcgctcgc tcgctcactg aggccgggcg accaaaggtc   4200
gcccgacgcc cgggctttgc ccgggcggcc tcagtgagcg agcgagcgcg cagccttaat   4260
taacctaatt cactggccgt cgttttacaa cgtcgtgact gggaaaaccc tggcgttacc   4320
caacttaatc gccttgcagc acatccccct ttcgccagct ggcgtaatag cgaagaggcc   4380
cgcaccgatc gcccttccca acagttgcgc agcctgaatg gcgaatggga cgcgccctgt   4440
agcggcgcat taagcgcggc gggtgtggtg gttacgcgca gcgtgaccgc tacacttgcc   4500
agcgccctag cgcccgctcc tttcgctttc ttcccttcct ttctcgccac gttcgccggc   4560
tttccccgtc aagctctaaa tcgggggctc cctttagggt tccgatttag tgctttacgg   4620
cacctcgacc ccaaaaaact tgattagggt gatggttcac gtagtgggcc atcgccctga   4680
tagacggttt ttcgcccttt gacgttggag tccacgttct ttaatagtgg actcttgttc   4740
caaactggaa caacactcaa ccctatctcg gtctattctt ttgatttata agggattttg   4800
ccgatttcgg cctattggtt aaaaaatgag ctgatttaac aaaaatttaa cgcgaatttt   4860
```

```
aacaaaatat taacgtttat aatttcaggt ggcatctttc ggggaaatgt gcgcggaacc   4920
cctatttgtt tatttttcta aatacattca aatatgtatc cgctcatgag acaataaccc   4980
tgataaatgc ttcaataata ttgaaaaagg aagagtatga gtattcaaca tttccgtgtc   5040
gcccttattc cctttttgc ggcattttgc cttcctgttt ttgctcaccc agaaacgctg    5100
gtgaaagtaa aagatgctga agatcagttg ggtgcacgag tgggttacat cgaactggat   5160
ctcaatagtg gtaagatcct tgagagtttt cgccccgaag aacgttttcc aatgatgagc   5220
acttttaaag ttctgctatg tggcgcggta ttatcccgta ttgacgccgg gcaagagcaa   5280
ctcggtcgcc gcatacacta ttctcagaat gacttggttg agtactcacc agtcacagaa   5340
aagcatctta cggatggcat gacagtaaga gaattatgca gtgctgccat aaccatgagt   5400
gataacactg cggccaactt acttctgaca acgatcggag gaccgaagga gctaaccgct   5460
tttttgcaca acatggggga tcatgtaact cgccttgatc gttgggaacc ggagctgaat   5520
gaagccatac caaacgacga gcgtgacacc acgatgcctg tagtaatggt aacaacgttg   5580
cgcaaactat taactggcga actacttact ctagcttccc ggcaacaatt aatagactgg   5640
atggaggcgg ataaagttgc aggaccactt ctgcgctcgg cccttccggc tggctggttt   5700
attgctgata aatctggagc cggtgagcgt gggtctcgcg gtatcattgc agcactgggg   5760
ccagatggta agccctcccg tatcgtagtt atctacacga cggggagtca ggcaactatg   5820
gatgaacgaa atagacagat cgctgagata ggtgcctcac tgattaagca ttggtaactg   5880
tcagaccaag tttactcata tatactttag attgatttaa aacttcattt ttaatttaaa   5940
aggatctagg tgaagatcct ttttgataat ctcatgacca aaatccctta acgtgagttt   6000
tcgttccact gagcgtcaga ccccgtagaa aagatcaaag gatcttcttg agatcctttt   6060
tttctgcgcg taatctgctg cttgcaaaca aaaaaaccac cgctaccagc ggtggtttgt   6120
ttgccggatc aagagctacc aactcttttt ccgaaggtaa ctggcttcag cagagcgcag   6180
ataccaaata ctgtccttct agtgtagccg tagttaggcc accacttcaa gaactctgta   6240
gcaccgccta catacctcgc tctgctaatc ctgttaccag tggctgctgc cagtggcgat   6300
aagtcgtgtc ttaccgggtt ggactcaaga cgatagttac cggataaggc gcagcggtcg   6360
ggctgaacgg ggggttcgtg cacacagccc agcttggagc gaacgaccta caccgaactg   6420
agatacctac agcgtgagct atgagaaagc gccacgcttc ccgaagggag aaaggcggac   6480
aggtatccgg taagcggcag ggtcggaaca ggagagcgca cgagggagct tccaggggga   6540
aacgcctggt atctttatag tcctgtcggg tttcgccacc tctgacttga gcgtcgattt   6600
ttgtgatgct cgtcaggggg gcggagccta tggaaaaacg ccagcaacgc ggccttttta   6660
cggttcctgg ccttttgctg cggttttgct cacatgttct ttcctgcgtt atcccctgat   6720
tctgtggata accgtattac cgcctttgag tgagctgata ccgctcgccg cagccgaacg   6780
accgagcgca gcgagtcagt gagcgaggaa gcggaagagc gcccaatacg caaaccgcct   6840
ctccccgcgc gttggccgat tcattaatgc agctggcacg acaggtttcc cgactggaaa   6900
gcgggcagtg agcgcaacgc aattaatgtg agttagctca ctcattaggc accccaggct   6960
ttacacttta tgcttccggc tcgtatgttg tgtggaattg tgagcggata acaatttcac   7020
acaggaaaca gctatgacca tgattacgcc agatttaatt aagg                    7064
```

<210> SEQ ID NO 4
<211> LENGTH: 7052
<212> TYPE: DNA

<213> ORGANISM: Artificial Sequence
<220> FEATURE:
<223> OTHER INFORMATION: synthetic expression construct

<400> SEQUENCE: 4

```
ctgcgcgctc gctcgctcac tgaggccgcc cgggcaaagc ccgggcgtcg ggcgaccttt     60
ggtcgcccgg cctcagtgag cgagcgagcg cgcagagagg gagtggccaa ctccatcact    120
aggggttcct tgtagttaat gattaacccg ccatgctact tatctacgta gccatgctct    180
aggaagatcg gaattcgccc ttaagctagc tagttattaa tagtaatcaa ttacggggtc    240
attagttcat agcccatata tggagttccg cgttacataa cttacggtaa atggcccgcc    300
tggctgaccg cccaacgacc cccgcccatt gacgtcaata atgacgtatg ttcccatagt    360
aacgccaata gggactttcc attgacgtca atgggtggag tatttacggt aaactgccca    420
cttggcagta catcaagtgt atcatatgcc aagtacgccc cctattgacg tcaatgacgg    480
taaatggccc gcctggcatt atgcccagta catgacctta tgggactttc ctacttggca    540
gtacatctac gtattagtca tcgctattac catggtgatg cggttttggc agtacatcaa    600
tgggcgtgga tagcggtttg actcacgggg atttccaagt ctccacccca ttgacgtcaa    660
tgggagtttg ttttggcacc aaaatcaacg ggactttcca aaatgtcgta acaactccgc    720
cccattgacg caaatgggcg gtaggcgtgt acggtgggag gtctatataa gcagagctgg    780
tttagtgaac cgtcagatcc tgcagaagtt ggtcgtgagg cactgggcag gtaagtatca    840
aggttacaag acaggtttaa ggagaccaat agaaactggg cttgtcgaga cagagaagac    900
tcttgcgttt ctgataggca cctattggtc ttactgacat ccactttgcc tttctctcca    960
caggtgtcca ggcggccgcg gatgttgcaa atccaagtgg aggagaaaga agaggataca   1020
gaggaaagct caagtgaaga agaagaagat aagctaccca gaagagagag cttgagacca   1080
aagaggaaac ggaccagaga tgtcatcaat gaggatgacc cagaaccgga gccggaggat   1140
gaagaaacaa gaaaggcaag agaaaaagaa aggcggagga ggctgcggag aggagcggaa   1200
gaagaagaag aaattgatga agaggaatta gaacggttaa aagcactgct cgatgagaat   1260
agacaaatga tcgctactgt caaatgtaaa ccttggaaaa tggagaagaa aattgaagtt   1320
ctcaaggaag caaagaaatt tgtgagtgag aatgaaggcg ctcttgggaa aggaaaggga   1380
aagaagtggt ttgcatttaa gatgatgatg gccaagaaat gggcaaaatt cctccgagat   1440
tttgagaact tcaaagcggc ttgcgtccca tgggaaaaca aaatcaaggc aattgaaagt   1500
cagtttggtt cctcagtggc ctcgtacttc ctgttcctca ggtggatgta cggcgtcaac   1560
atggttctct ttgtgttgac cttcagcctc atcatgttac cggagtacct ctggggttta   1620
ccgtacggca gcttacctag gaaaacagtc ccaagagctg aagaagcatc tgcagccaac   1680
tttggtgtgt tgtatgactt caatggcctg gcgcagtact ctgtcctctt ttatggctat   1740
tacgacaata aacgcacgat cggatggctg aatttccggc tacctctttc ctacttcctg   1800
gtggggatta tgtgcattgg atacagcttc ctggttgtcc tcaaagcgat gaccaaaaat   1860
attggtgacg atggtggtgg cgatgacaac actttcaact tcagctggaa ggtgttctgt   1920
agctgggact atctgattgg taaccctgaa acagccgaca acaagtttaa ctctatcacg   1980
atgaacttta aggaagccat catagaagag agagccgcac aggtggagga gaacatccac   2040
ctcatcagat ttctgaggtt tctcgctaac ttcttcgtgt tcctcacact tggtgcaagt   2100
ggatacctca tcttttgggc tgtgaagcga tcccaggagt tcgcccagca agatcctgac   2160
acccttgggt ggtgggaaaa aaatgaaatg aacatggtaa tgtccctcct ggggatgttc   2220
```

```
tgtcccaccc tgtttgactt atttgctgaa ctggaagatt accatcctct cattgctctg   2280
aagtggctcc tggggcgcat ttttgctctt cttctaggca acttgtatgt attcattctc   2340
gccttgatgg atgagattaa caacaagatt gaagaggaga agcttgtgaa ggccaatatt   2400
accctgtggg aagccaacat gattaaggct tacaatgaat ctctctctgg gctctctggg   2460
aacaccacag gagcaccctt tttcgttcat cctgcagatg tccctcgcgg tccctgctgg   2520
gaaacaatgg tggggcagga attcgtgcgt ctcaccgttt ctgacgtcct gaccacttac   2580
gtcacgatcc tcattggcga cttcctcaga gcatgtttcg tgaggttctg caattactgc   2640
tggtgctggg acttagaata tggatatcct tcatacacag aattcgacat cagtggcaac   2700
gtcctcgctc tgatcttcaa ccaaggcatg atctggatgg gctccttctt cgctcctagc   2760
ctcccgggca tcaacatcct ccgtctccac acatccatgt atttccagtg ctgggctgtg   2820
atgtgctgca atgttcccga ggccagggtg ttcaaagctt ccagatccaa caacttctac   2880
ctcggcatgc tgctactcat cctcttcctg tccaccatgc cggtcctgta catgatcgtc   2940
tccctcccgc catcttttga ttgtgggccc ttcagtggta aaaacaggat gtttgaagtc   3000
atcggtgaga ccctggaaca tgacttccca agctggatgg cgaagatcct gaggcagctt   3060
tctaaccccg gccttgtcat tgctgtcatt ctggtgatgg ttctgaccat ctattatctc   3120
aatgctactg ccaagggcca gaaagcagcg aatctggacc tcaaaaagaa gatgaaacag   3180
caagctttgg agaacaaaat gcgaaacaag aaaatggcag cggctcgagc agctgcagct   3240
gctggtggcc agtaaggatc caatcaacct ctggattaca aaatttgtga aagattgact   3300
ggtattctta actatgttgc tccttttacg ctatgtggat acgctgcttt aatgcctttg   3360
tatcatgcta ttgcttcccg tatggctttc attttctcct ccttgtataa atcctggttg   3420
ctgtctcttt atgaggagtt gtggcccgtt gtcaggcaac gtggcgtggt gtgcactgtg   3480
tttgctgacg caacccccac tggttggggc attgccacca cctgtcagct cctttccggg   3540
actttcgctt tccccctccc tattgccacg gcggaactca tcgccgcctg ccttgcccgc   3600
tgctggacag gggctcggct gttgggcact gacaattccg tggtgttgtc ggggaaatca   3660
tcgtcctttc cttggctgct cgcctgtgtt gccacctgga ttctgcgcgg gacgtccttc   3720
tgctacgtcc cttcggccct caatccagcg gaccttcctt cccgcggcct gctgccggct   3780
ctgcggcctc ttccgcgtct tcgagatctg cctcgactgt gccttctagt tgccagccat   3840
ctgttgtttg cccctccccc gtgccttcct tgaccctgga aggtgccact cccactgtcc   3900
tttcctaata aaatgaggaa attgcatcgc attgtctgag taggtgtcat tctattctgg   3960
ggggtggggt ggggcaggac agcaaggggg aggattggga agacaatagc aggcatgctg   4020
gggactcgag ttaagggcga attcccgata aggatcttcc tagagcatgg ctacgtagat   4080
aagtagcatg gcgggttaat cattaactac aaggaacccc tagtgatgga gttggccact   4140
ccctctctgc gcgctcgctc gctcactgag gccgggcgac caaaggtcgc ccgacgcccg   4200
ggctttgccc gggcggcctc agtgagcgag cgagcgcgca gccttaatta acctaattca   4260
ctggccgtcg ttttacaacg tcgtgactgg gaaaaccctg gcgttaccca acttaatcgc   4320
cttgcagcac atccccctttt cgccagctgg cgtaatagcg aagaggcccg caccgatcgc   4380
ccttcccaac agttgcgcag cctgaatggc gaatgggacg cgccctgtag cggcgcatta   4440
agcgcggcgg gtgtggtggt tacgcgcagc gtgaccgcta cacttgccag cgccctagcg   4500
cccgctcctt tcgctttctt cccttccttt ctcgccacgt tcgccggctt tccccgtcaa   4560
```

```
gctctaaatc gggggctccc tttagggttc cgatttagtg ctttacggca cctcgacccc   4620
aaaaaacttg attagggtga tggttcacgt agtgggccat cgccctgata gacggttttt   4680
cgccctttga cgttggagtc cacgttcttt aatagtggac tcttgttcca aactggaaca   4740
acactcaacc ctatctcggt ctattctttt gatttataag ggattttgcc gatttcggcc   4800
tattggttaa aaaatgagct gatttaacaa aaatttaacg cgaattttaa caaaatatta   4860
acgtttataa tttcaggtgg catctttcgg ggaaatgtgc gcggaacccc tatttgttta   4920
tttttctaaa tacattcaaa tatgtatccg ctcatgagac aataaccctg ataaatgctt   4980
caataatatt gaaaaaggaa gagtatgagt attcaacatt tccgtgtcgc ccttattccc   5040
ttttttgcgg cattttgcct tcctgttttt gctcacccag aaacgctggt gaaagtaaaa   5100
gatgctgaag atcagttggg tgcacgagtg ggttacatcg aactggatct caatagtggt   5160
aagatccttg agagttttcg ccccgaagaa cgttttccaa tgatgagcac ttttaaagtt   5220
ctgctatgtg gcgcggtatt atcccgtatt gacgccgggc aagagcaact cggtcgccgc   5280
atacactatt ctcagaatga cttggttgag tactcaccag tcacagaaaa gcatcttacg   5340
gatggcatga cagtaagaga attatgcagt gctgccataa ccatgagtga taacactgcg   5400
gccaacttac ttctgacaac gatcggagga ccgaaggagc taaccgcttt tttgcacaac   5460
atgggggatc atgtaactcg ccttgatcgt tgggaaccgg agctgaatga agccatacca   5520
aacgacgagc gtgacaccac gatgcctgta gtaatggtaa caacgttgcg caaactatta   5580
actggcgaac tacttactct agcttcccgg caacaattaa tagactggat ggaggcggat   5640
aaagttgcag gaccacttct gcgctcggcc cttccggctg gctggtttat tgctgataaa   5700
tctggagccg gtgagcgtgg gtctcgcggt atcattgcag cactggggcc agatggtaag   5760
ccctcccgta tcgtagttat ctacacgacg gggagtcagg caactatgga tgaacgaaat   5820
agacagatcg ctgagatagg tgcctcactg attaagcatt ggtaactgtc agaccaagtt   5880
tactcatata tactttagat tgatttaaaa cttcattttt aatttaaaag gatctaggtg   5940
aagatccttt ttgataatct catgaccaaa atcccttaac gtgagttttc gttccactga   6000
gcgtcagacc ccgtagaaaa gatcaaagga tcttcttgag atcctttttt tctgcgcgta   6060
atctgctgct tgcaaacaaa aaaaccaccg ctaccagcgg tggtttgttt gccggatcaa   6120
gagctaccaa ctctttttcc gaaggtaact ggcttcagca gagcgcagat accaaatact   6180
gtccttctag tgtagccgta gttaggccac cacttcaaga actctgtagc accgcctaca   6240
tacctcgctc tgctaatcct gttaccagtg gctgctgcca gtggcgataa gtcgtgtctt   6300
accgggttgg actcaagacg atagttaccg gataaggcgc agcggtcggg ctgaacgggg   6360
ggttcgtgca cacagcccag cttggagcga acgacctaca ccgaactgag atacctacag   6420
cgtgagctat gagaaagcgc cacgcttccc gaagggagaa aggcggacag gtatccggta   6480
agcggcaggg tcggaacagg agagcgcacg agggagcttc cagggggaaa cgcctggtat   6540
ctttatagtc ctgtcgggtt tcgccacctc tgacttgagc gtcgattttt gtgatgctcg   6600
tcaggggggc ggagcctatg gaaaaacgcc agcaacgcgg cctttttacg gttcctggcc   6660
ttttgctgcg gttttgctca catgttcttt cctgcgttat cccctgattc tgtggataac   6720
cgtattaccg cctttgagtg agctgatacc gctcgccgca gccgaacgac cgagcgcagc   6780
gagtcagtga gcgaggaagc ggaagagcgc ccaatacgca aaccgcctct ccccgcgcgt   6840
tggccgattc attaatgcag ctggcacgac aggtttcccg actggaaagc gggcagtgag   6900
cgcaacgcaa ttaatgtgag ttagctcact cattaggcac cccaggcttt acactttatg   6960
```

```
cttccggctc gtatgttgtg tggaattgtg agcggataac aatttcacac aggaaacagc   7020

tatgaccatg attacgccag atttaattaa gg                                 7052


<210> SEQ ID NO 5
<211> LENGTH: 7451
<212> TYPE: DNA
<213> ORGANISM: Artificial Sequence
<220> FEATURE:
<223> OTHER INFORMATION: synthetic expression construct

<400> SEQUENCE: 5

ctgcgcgctc gctcgctcac tgaggccgcc cgggcaaagc ccgggcgtcg ggcgaccttt     60

ggtcgcccgg cctcagtgag cgagcgagcg cgcagagagg gagtggccaa ctccatcact    120

aggggttcct tgtagttaat gattaacccg ccatgctact tatctacgta gccatgctct    180

aggaagatcg gaattcgccc ttaagctagc tagttattaa tagtaatcaa ttacggggtc    240

attagttcat agcccatata tggagttccg cgttacataa cttacggtaa atggcccgcc    300

tggctgaccg cccaacgacc cccgcccatt gacgtcaata atgacgtatg ttcccatagt    360

aacgccaata gggactttcc attgacgtca atgggtggag tatttacggt aaactgccca    420

cttggcagta catcaagtgt atcatatgcc aagtacgccc cctattgacg tcaatgacgg    480

taaatggccc gcctggcatt atgcccagta catgacctta tgggactttc ctacttggca    540

gtacatctac gtattagtca tcgctattac catggtgatg cggttttggc agtacatcaa    600

tgggcgtgga tagcggtttg actcacgggg atttccaagt ctccacccca ttgacgtcaa    660

tgggagtttg ttttggcacc aaaatcaacg ggactttcca aaatgtcgta acaactccgc    720

cccattgacg caaatgggcg gtaggcgtgt acggtgggag gtctatataa gcagagctgg    780

tttagtgaac cgtcagatcc tgcagaagtt ggtcgtgagg cactgggcag gtaagtatca    840

aggttacaag acaggtttaa ggagaccaat agaaactggg cttgtcgaga cagagaagac    900

tcttgcgttt ctgataggca cctattggtc ttactgacat ccactttgcc tttctctcca    960

caggtgtcca ggcggccgcc atgagccccc agttaaagag cttggacgag gaaggtgaca   1020

agtcagcaag aagacccaca aggaaacaaa cctccagagc tgcatgtccc caagacgggc   1080

accgagccca atctagccgg aaggatcctg ctaagggtag cccaagacca gggtcttccc   1140

ggaagaaaca gatggaacat ggaagctatc acaaggggtt gcagggacag aaaccacgaa   1200

aggtggagag gtctctacaa gggaggaaga aggatcggag aacttccctt aaggagcaga   1260

gagcatctcc aaagaaggag agggaggctc tgaggaagga ggcaggcaag cagctgagaa   1320

aacccaggtc cacttccttg ggctccagtg tctctactgg agactccctg tctgaggagg   1380

agctggctca gatcctggaa caggtagaag aaaaaaagaa gctcatcact accgtgagga   1440

acaaaccctg gcccatggca aagaagctga gggaactcag ggaagcccaa gcctttgtgg   1500

agaagtatga aggagccttg ggaaaaggca agggcaaaca cctctacgcc tacaggatga   1560

tgatggctaa gaaatgggtc aagtttaaga gggactttga taatttcaag actcaatgta   1620

ttccctggga aatgaagatc aaggacattg aaagtcactt cggttcttct gtggcatctt   1680

acttcatctt tctccgatgg atgtatggag ttaaccttgt cctttttggc ttaatatttg   1740

gtctagtcat catcccagag gtgctgatgg gcatgcccta tggaagtata cccagaaaga   1800

cggtgcctcg ggctgaggaa gagcgagcca tggacttctc tgtcctttgg gattttgagg   1860

gctacatcaa atattctgct ctcttctatg gctactacaa caaccagcgg accattggat   1920
```

```
ggctgaggta caggctgccc atggcttact ttatggtggg ggtcagcgtg tttggctaca   1980
gcttgatgat cgtcattagg tcgatggcca gcaataccca gggtagcacc agtgaggggg   2040
acagtgacag cttcacgttc agcttcaaga tgttcaccag ctgggactac ctcatcggga   2100
attcagagac agcagacaac aaatatgtct ccatcactac cagcttcaag gagtctatag   2160
tggacgaaca agagagtaac aaagaaggga atatccacct gacaagattc ctccgcgtcc   2220
tggccaactt tctcattctc tgctgtctgt gtggaagcgg gtacctcatt tactttgtgg   2280
tgaaacggtc ccaggagttc tccaaaaatgc aaaatgtcag ctggtatgaa aggaatgagg   2340
tggagatcgt gatgtctctg ctagggatgt tttgtccccc tctgtttgaa accatcgctg   2400
ccttggagaa ttatcaccca cgaactgggc tgaagtggca gctgggccgc atctttgccc   2460
ttttcctggg aaacctctac acgtttctcc tggccctcat ggacgatgtc caccttaagc   2520
tttctaatga ggaaaaaatc aagaacatca ctcactggac cctgtttaac tattacaatt   2580
cctcaggtgg gaatgagagt gtgccccggc caccaccaca ccctgcagat gtgcccagag   2640
gttcttgctg ggagacagct gtgggcattg agtttatgag gctcaccgtg tctgacatgc   2700
tggtaacata cctcaccatc ttggtcggag atttcctccg agcttgtttt gtccggttca   2760
tgaatcactg ctggtgttgg gacctcgagg ctggttttcc ctcatatgcc gagtttgata   2820
ttagtggaaa tgtgttgggt ttgatcttca accaaggaat gatctggatg ggctccttct   2880
atgctccagg actggtgggc atcaatgtcc tgcgcctgtt gacctccatg tacttccagt   2940
gctgggcagt gatgagcagc aacgttcccc atgagcgtgt gtttaaagcc tcccgatcca   3000
acaacttcta catgggcctg ctgctgttgg tgctcttcct cagcctcctg cctgtggcct   3060
acactgtcat gtctctccca ccctcgtttg actgtggccc cttcagtggg aaaaacagaa   3120
tgtacgatgt cctccatgag accatcgaga acgatttccc taagttcctg ggcaagatct   3180
ttgcgttcct tgccaaccca ggcctgatca ttccagccat cctgctaatg tttctggcca   3240
tttactacct gaactcagtt tcaaaaagtc tttccagagc taatgcccag ctgcgaaaga   3300
agatccaagc gctccgtgaa gttgagaaga accataaatc catcaaggga aaagccatag   3360
tcacatattc agaggacaca atcaagaaca gctccaaaaa tgccacccag atacatctta   3420
ctaaagaaga gcccacatct cactcttcca gccaaatcca gaccctggac aagaaagcgc   3480
agggcccccca cacctccagt actgagggtg gggcctcgcc gtctacctcc tggcaccatg   3540
ttgggtctca accaccgaga ggcagacgag attctggcca accccagtct cagacttata   3600
caggcaggtc accttctgga aagagaaccc agaggcctca caactgataa gcttggatcc   3660
aatcaacctc tggattacaa aatttgtgaa agattgactg gtattcttaa ctatgttgct   3720
ccttttacgc tatgtggata cgctgcttta atgcctttgt atcatgctat tgcttcccgt   3780
atggctttca ttttctcctc cttgtataaa tcctggttgc tgtctcttta tgaggagttg   3840
tggcccgttg tcaggcaacg tggcgtggtg tgcactgtgt ttgctgacgc aacccccact   3900
ggttggggca ttgccaccac ctgtcagctc ctttccggga ctttcgcttt ccccctccct   3960
attgccacgg cggaactcat cgccgcctgc cttgcccgct gctggacagg ggctcggctg   4020
ttgggcactg acaattccgt ggtgttgtcg gggaaatcat cgtcctttcc ttggctgctc   4080
gcctgtgttg ccacctggat tctgcgcggg acgtccttct gctacgtccc ttcggccctc   4140
aatccagcgg accttccttc ccgcggcctg ctgccggctc tgcggcctct tccgcgtctt   4200
cgagatctgc ctcgactgtg ccttctagtt gccagccatc tgttgtttgc ccctcccccg   4260
tgccttcctt gaccctggaa ggtgccactc ccactgtcct ttcctaataa aatgaggaaa   4320
```

```
ttgcatcgca ttgtctgagt aggtgtcatt ctattctggg gggtggggtg gggcaggaca   4380
gcaaggggga ggattgggaa gacaatagca ggcatgctgg ggactcgagt taagggcgaa   4440
ttcccgataa ggatcttcct agagcatggc tacgtagata agtagcatgg cgggttaatc   4500
attaactaca aggaacccct agtgatggag ttggccactc cctctctgcg cgctcgctcg   4560
ctcactgagg ccgggcgacc aaaggtcgcc cgacgcccgg gctttgcccg ggcggcctca   4620
gtgagcgagc gagcgcgcag ccttaattaa cctaattcac tggccgtcgt tttacaacgt   4680
cgtgactggg aaaaccctgg cgttacccaa cttaatcgcc ttgcagcaca tccccctttc   4740
gccagctggc gtaatagcga agaggcccgc accgatcgcc cttcccaaca gttgcgcagc   4800
ctgaatggcg aatgggacgc gccctgtagc ggcgcattaa gcgcggcggg tgtggtggtt   4860
acgcgcagcg tgaccgctac acttgccagc gccctagcgc ccgctccttt cgctttcttc   4920
ccttcctttc tcgccacgtt cgccggcttt ccccgtcaag ctctaaatcg ggggctccct   4980
ttagggttcc gatttagtgc tttacggcac ctcgacccca aaaaacttga ttagggtgat   5040
ggttcacgta gtgggccatc gccctgatag acggtttttc gccctttgac gttggagtcc   5100
acgttcttta atagtggact cttgttccaa actggaacaa cactcaaccc tatctcggtc   5160
tattcttttg atttataagg gattttgccg atttcggcct attggttaaa aaatgagctg   5220
atttaacaaa aatttaacgc gaattttaac aaaatattaa cgtttataat ttcaggtggc   5280
atctttcggg gaaatgtgcg cggaacccct atttgtttat ttttctaaat acattcaaat   5340
atgtatccgc tcatgagaca ataaccctga taaatgcttc aataatattg aaaaaggaag   5400
agtatgagta ttcaacattt ccgtgtcgcc cttattccct tttttgcggc attttgcctt   5460
cctgtttttg ctcacccaga aacgctggtg aaagtaaaag atgctgaaga tcagttgggt   5520
gcacgagtgg gttacatcga actggatctc aatagtggta agatccttga gagttttcgc   5580
cccgaagaac gttttccaat gatgagcact tttaaagttc tgctatgtgg cgcggtatta   5640
tcccgtattg acgccgggca agagcaactc ggtcgccgca tacactattc tcagaatgac   5700
ttggttgagt actcaccagt cacagaaaag catcttacgg atggcatgac agtaagagaa   5760
ttatgcagtg ctgccataac catgagtgat aacactgcgg ccaacttact tctgacaacg   5820
atcggaggac cgaaggagct aaccgctttt ttgcacaaca tgggggatca tgtaactcgc   5880
cttgatcgtt gggaaccgga gctgaatgaa gccataccaa acgacgagcg tgacaccacg   5940
atgcctgtag taatggtaac aacgttgcgc aaactattaa ctggcgaact acttactcta   6000
gcttcccggc aacaattaat agactggatg gaggcggata aagttgcagg accacttctg   6060
cgctcggccc ttccggctgg ctggtttatt gctgataaat ctggagccgg tgagcgtggg   6120
tctcgcggta tcattgcagc actggggcca gatggtaagc cctcccgtat cgtagttatc   6180
tacacgacgg ggagtcaggc aactatggat gaacgaaata gacagatcgc tgagataggt   6240
gcctcactga ttaagcattg gtaactgtca gaccaagttt actcatatat actttagatt   6300
gatttaaaac ttcattttta atttaaaagg atctaggtga agatcctttt tgataatctc   6360
atgaccaaaa tcccttaacg tgagttttcg ttccactgag cgtcagaccc cgtagaaaag   6420
atcaaaggat cttcttgaga tccttttttt ctgcgcgtaa tctgctgctt gcaaacaaaa   6480
aaaccaccgc taccagcggt ggtttgtttg ccggatcaag agctaccaac tctttttccg   6540
aaggtaactg gcttcagcag agcgcagata ccaaatactg tccttctagt gtagccgtag   6600
ttaggccacc acttcaagaa ctctgtagca ccgcctacat acctcgctct gctaatcctg   6660
```

```
ttaccagtgg ctgctgccag tggcgataag tcgtgtctta ccgggttgga ctcaagacga   6720

tagttaccgg ataaggcgca gcggtcgggc tgaacggggg gttcgtgcac acagcccagc   6780

ttggagcgaa cgacctacac cgaactgaga tacctacagc gtgagctatg agaaagcgcc   6840

acgcttcccg aagggagaaa ggcggacagg tatccggtaa gcggcagggt cggaacagga   6900

gagcgcacga gggagcttcc agggggaaac gcctggtatc tttatagtcc tgtcgggttt   6960

cgccacctct gacttgagcg tcgatttttg tgatgctcgt caggggggcg gagcctatgg   7020

aaaaacgcca gcaacgcggc ctttttacgg ttcctggcct tttgctgcgg ttttgctcac   7080

atgttctttc ctgcgttatc ccctgattct gtggataacc gtattaccgc ctttgagtga   7140

gctgataccg ctcgccgcag ccgaacgacc gagcgcagcg agtcagtgag cgaggaagcg   7200

gaagagcgcc caatacgcaa accgcctctc cccgcgcgtt ggccgattca ttaatgcagc   7260

tggcacgaca ggtttcccga ctggaaagcg ggcagtgagc gcaacgcaat taatgtgagt   7320

tagctcactc attaggcacc ccaggcttta cactttatgc ttccggctcg tatgttgtgt   7380

ggaattgtga gcggataaca atttcacaca ggaaacagct atgaccatga ttacgccaga   7440

tttaattaag g                                                        7451
```

<210> SEQ ID NO 6
<211> LENGTH: 6999
<212> TYPE: DNA
<213> ORGANISM: Artificial Sequence
<220> FEATURE:
<223> OTHER INFORMATION: synthetic expression construct

<400> SEQUENCE: 6

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtgcaag aaccctcact ggctgaacta    180

tcttgccagc cccttatttt gttttcatat taacctcttt tttctagtaa aggagatgtt    240

tgctctcaaa tttgcatagg aatgtaatat ttaatttaaa aagatgaccc acatatgacc    300

ttataaggac agtaaaatta aacaaccgga aagataaagc gggccagttg gctcagttct    360

ataaaaccag cccacaagga ttgtcactat tcttaggctt gcgcgggcta catgatgagt    420

tccaggactg cctggttaca gaccgagact ctctcaagag tccagataaa caacaacaaa    480

gggggcgagg tggaaataca ggggctgtaa gaagtaaata tgatatctgc atgggaggct    540

agccagagaa gaaaaaattt tcttccgtgg ttcaatcctc caagggctga acaggaagtt    600

gacgcaggca ggtgaggagc acgagcctag atgggctgcg gtgccaccct taatccccac    660

aagcgagttc ctccgcaatt cgcctgtccc actctcaact ttcttcaac tgactctttg     720

ctgtggtccc tcgctgtggc agtggaaaca actaccactg cgaggtaggg aatgtcatga    780

ggggctacct gcagcccttg gcttgcaggg atgcagggat gcggtcggaa cctgaggccc    840

cgcccttctc ttgccccacg ccattaggcc acgcccctac ccagcactcc ttcaaccacc    900

cccttccccg gcgcctcatg aggtcccgcc cctctcaacc ctagctcttg aggcctcccc    960

ttcacagccg ccccggcgtt ccttgacttg aggccacgtc cctctgctcc ttcattccca   1020

agaccctacg ctttgcgagt cctccctgtc ctgctgccta ggaccccgcc cctctcagcc   1080

cttctgcccc aagaccccgc cccttaggct gttcccgccc actggccaat gaagacccgc   1140

cctttcttta gccgccccgc cccggtccca caaaatcccg cctccggccc cgcctcccgc   1200

ccccttgggc gctccgtagc agtgacgtgc gcaggctggg cactctgcag ggctctctgg   1260
```

```
ccggcgggtg gagaccgatc cgggatctgt cccagcagga agcgtatccc ggccgccgtc   1320
gtgctgtcgt ctccggtgct cgctctcggc cgcggtgtcg cgcttgccct tcgcgcccgc   1380
agcccggcag cctctcgagc tcaagcttcg aattcgtcga caggatgcca cccaaaaaag   1440
tgcaaatcca agtggaggag aaagaagagg atacagagga aagctcaagt gaagaagaag   1500
aagataagct acccagaaga gagagcttga gaccaaagag gaaacggacc agagatgtca   1560
tcaatgagga tgacccagaa ccggagccgg aggatgaaga aacaagaaag gcaagagaaa   1620
aagaaaggcg gaggaggctg cggagaggag cggaagaaga agaagaaatt gatgaagagg   1680
aattagaacg gttaaaagca ctgctcgatg agaatagaca aatgatcgct actgtcaaat   1740
gtaaaccttg gaaaatggag aagaaaattg aagttctcaa ggaagcaaag aaatttgtga   1800
gtgagaatga aggcgctctt gggaaaggaa agggaaagaa gtggtttgca tttaagatga   1860
tgatggccaa gaaatgggca aaattcctcc gagattttga gaacttcaaa gcggcttgcg   1920
tcccatggga aaacaaaatc aaggcaattg aaagtcagtt tggttcctca gtggcctcgt   1980
acttcctgtt cctcaggtgg atgtacggcg tcaacatggt tctctttgtg ttgaccttca   2040
gcctcatcat gttaccggag tacctctggg gtttaccgta cggcagctta cctaggaaaa   2100
cagtcccaag agctgaagaa gcatctgcag ccaactttgg tgtgttgtat gacttcaatg   2160
gcctggcgca gtactctgtc ctcttttatg gctattacga caataaacgc acgatcggat   2220
ggctgaattt ccggctacct ctttcctact tcctggtggg gattatgtgc attggataca   2280
gcttcctggt tgtcctcaaa gcgatgacca aaaatattgg tgacgatggt ggtggcgatg   2340
acaacacttt caacttcagc tggaaggtgt tctgtagctg ggactatctg attggtaacc   2400
ctgaaacagc cgacaacaag tttaactcta tcacgatgaa ctttaaggaa gccatcatag   2460
aagagagagc cgcacaggtg gaggagaaca tccacctcat cagatttctg aggtttctcg   2520
ctaacttctt cgtgttcctc acacttggtg caagtggata cctcatcttt tgggctgtga   2580
agcgatccca ggagttcgcc cagcaagatc ctgacaccct tgggtggtgg gaaaaaaatg   2640
aaatgaacat ggtaatgtcc ctcctgggga tgttctgtcc caccctgttt gacttatttg   2700
ctgaactgga agattaccat cctctcattg ctctgaagtg gctcctgggg cgcatttttg   2760
ctcttcttct aggcaacttg tatgtattca ttctcgcctt gatggatgag attaacaaca   2820
agattgaaga ggagaagctt gtgaaggcca atattaccct gtgggaagcc aacatgatta   2880
aggcttacaa tgaatctctc tctgggctct ctgggaacac cacaggagca ccctttttcg   2940
ttcatcctgc agatgtccct cgcggtccct gctgggaaac aatggtgggg caggaattcg   3000
tgcgtctcac cgtttctgac gtcctgacca cttacgtcac gatcctcatt ggcgacttcc   3060
tcagagcatg tttcgtgagg ttctgcaatt actgctggtg ctgggactta gaatatggat   3120
atccttcata cacagaattc gacatcagtg gcaacgtcct cgctctgatc ttcaaccaag   3180
gcatgatctg gatgggctcc ttcttcgctc ctagcctccc gggcatcaac atcctccgtc   3240
tccacacatc catgtatttc cagtgctggg ctgtgatgtg ctgcaatgtt cccgaggcca   3300
gggtgttcaa agcttccaga tccaacaact tctacctcgg catgctgcta ctcatcctct   3360
tcctgtccac catgccggtc ctgtacatga tcgtctccct cccgccatct tttgattgtg   3420
ggcccttcag tggtaaaaac aggatgtttg aagtcatcgg tgagaccctg gaacatgact   3480
tcccaagctg gatggcgaag atcctgaggc agctttctaa ccccggcctt gtcattgctg   3540
tcattctggt gatggttctg accatctatt atctcaatgc tactgccaag ggccagaaag   3600
```

-continued

```
cagcgaatct ggacctcaaa aagaagatga aacagcaagc tttggagaac aaaatgcgaa   3660
acaagaaaat ggcagcggct cgagcagctg cagctgctgg tggccagtaa gcggccgctc   3720
gagcctaagc ttctagaaga tctacgggtg gcatccctgt gacccctccc cagtgcctct   3780
cctggccctg gaagttgcca ctccagtgcc caccagcctt gtcctaataa aattaagttg   3840
catcattttg tctgactagg tgtccttcta taatattatg gggtggaggg gggtggtatg   3900
gagcaagggg caagttggga agacaacctg tagggcctgc ggggtctatt gggaaccaag   3960
ctggagtgca gtggcacaat cttggctcac tgcaatctcc gcctcctggg ttcaagcgat   4020
tctcctgcct cagcctcccg agttgttggg attccaggca tgcatgacca ggctcagcta   4080
atttttgttt ttttggtaga gacggggttt caccatattg gccaggctgg tctccaactc   4140
ctaatctcag gtgatctacc caccttggcc tcccaaattg ctgggattac aggcgtgaac   4200
cactgctccc ttccctgtcc ttctgatttt gtaggtaacc acgtgcggac cgagcggccg   4260
caggaacccc tagtgatgga gttggccact ccctctctgc gcgctcgctc gctcactgag   4320
gccgggcgac caaaggtcgc ccgacgcccg ggctttgccc gggcggcctc agtgagcgag   4380
cgagcgcgca gctgcctgca ggggcgcctg atgcggtatt ttctccttac gcatctgtgc   4440
ggtatttcac accgcatacg tcaaagcaac catagtacgc gccctgtagc ggcgcattaa   4500
gcgcggcggg tgtggtggtt acgcgcagcg tgaccgctac acttgccagc gccctagcgc   4560
ccgctccttt cgctttcttc ccttcctttc tcgccacgtt cgccggcttt ccccgtcaag   4620
ctctaaatcg ggggctccct ttagggttcc gatttagtgc tttacggcac ctcgacccca   4680
aaaaacttga tttgggtgat ggttcacgta gtgggccatc gccctgatag acggtttttc   4740
gccctttgac gttggagtcc acgttcttta atagtggact cttgttccaa actggaacaa   4800
cactcaaccc tatctcgggc tattcttttg atttataagg gattttgccg atttcggcct   4860
attggttaaa aaatgagctg atttaacaaa aatttaacgc gaattttaac aaaatattaa   4920
cgtttacaat tttatggtgc actctcagta caatctgctc tgatgccgca tagttaagcc   4980
agccccgaca cccgccaaca cccgctgacg cgccctgacg ggcttgtctg ctcccggcat   5040
ccgcttacag acaagctgtg accgtctccg ggagctgcat gtgtcagagg ttttcaccgt   5100
catcaccgaa acgcgcgaga cgaaagggcc tcgtgatacg cctattttta taggttaatg   5160
tcatgataat aatggtttct tagacgtcag gtggcacttt tcggggaaat gtgcgcggaa   5220
cccctatttg tttatttttc taaatacatt caaatatgta tccgctcatg agacaataac   5280
cctgataaat gcttcaataa tattgaaaaa ggaagagtat gagtattcaa catttccgtg   5340
tcgcccttat tccctttttt gcggcatttt gccttcctgt ttttgctcac ccagaaacgc   5400
tggtgaaagt aaaagatgct gaagatcagt tgggtgcacg agtgggttac atcgaactgg   5460
atctcaacag cggtaagatc cttgagagtt ttcgccccga agaacgtttt ccaatgatga   5520
gcacttttaa agttctgcta tgtggcgcgg tattatcccg tattgacgcc gggcaagagc   5580
aactcggtcg ccgcatacac tattctcaga atgacttggt tgagtactca ccagtcacag   5640
aaaagcatct tacggatggc atgacagtaa gagaattatg cagtgctgcc ataaccatga   5700
gtgataacac tgcggccaac ttacttctga caacgatcgg aggaccgaag gagctaaccg   5760
cttttttgca caacatgggg gatcatgtaa ctcgccttga tcgttgggaa ccggagctga   5820
atgaagccat accaaacgac gagcgtgaca ccacgatgcc tgtagcaatg gcaacaacgt   5880
tgcgcaaact attaactggc gaactactta ctctagcttc ccggcaacaa ttaatagact   5940
ggatggaggc ggataaagtt gcaggaccac ttctgcgctc ggcccttccg gctggctggt   6000
```

ttattgctga taaatctgga gccggtgagc gtgggtctcg cggtatcatt gcagcactgg 6060
ggccagatgg taagccctcc cgtatcgtag ttatctacac gacggggagt caggcaacta 6120
tggatgaacg aaatagacag atcgctgaga taggtgcctc actgattaag cattggtaac 6180
tgtcagacca agtttactca tatatacttt agattgattt aaaacttcat ttttaattta 6240
aaaggatcta ggtgaagatc ctttttgata atctcatgac caaaatccct taacgtgagt 6300
tttcgttcca ctgagcgtca gaccccgtag aaaagatcaa aggatcttct tgagatcctt 6360
tttttctgcg cgtaatctgc tgcttgcaaa caaaaaaacc accgctacca gcggtggttt 6420
gtttgccgga tcaagagcta ccaactcttt ttccgaaggt aactggcttc agcagagcgc 6480
agataccaaa tactgtcctt ctagtgtagc cgtagttagg ccaccacttc aagaactctg 6540
tagcaccgcc tacatacctc gctctgctaa tcctgttacc agtggctgct gccagtggcg 6600
ataagtcgtg tcttaccggg ttggactcaa gacgatagtt accggataag gcgcagcggt 6660
cgggctgaac ggggggttcg tgcacacagc ccagcttgga gcgaacgacc tacaccgaac 6720
tgagatacct acagcgtgag ctatgagaaa gcgccacgct tcccgaaggg agaaaggcgg 6780
acaggtatcc ggtaagcggc agggtcggaa caggagagcg cacgagggag cttccagggg 6840
gaaacgcctg gtatctttat agtcctgtcg ggtttcgcca cctctgactt gagcgtcgat 6900
ttttgtgatg ctcgtcaggg gggcggagcc tatggaaaaa cgccagcaac gcggcctttt 6960
tacggttcct ggccttttgc tggccttttg ctcacatgt 6999

<210> SEQ ID NO 7
<211> LENGTH: 7728
<212> TYPE: DNA
<213> ORGANISM: Artificial Sequence
<220> FEATURE:
<223> OTHER INFORMATION: synthetic expression construct

<400> SEQUENCE: 7
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtgcaag aaccctcact ggctgaacta 180
tcttgccagc cccttatttt gttttcatat taacctcttt tttctagtaa aggagatgtt 240
tgctctcaaa tttgcatagg aatgtaatat ttaatttaaa aagatgaccc acatatgacc 300
ttataaggac agtaaaatta aacaaccgga aagataaagc gggccagttg gctcagttct 360
ataaaaccag cccacaagga ttgtcactat tcttaggctt gcgcgggcta catgatgagt 420
tccaggactg cctggttaca gaccgagact ctctcaagag tccagataaa caacaacaaa 480
gggggcgagg tggaaataca ggggctgtaa gaagtaaata tgatatctgc atgggaggct 540
agccagagaa gaaaaaattt tcttccgtgg ttcaatcctc caagggctga acaggaagtt 600
gacgcaggca ggtgaggagc acgagcctag atgggctgcg gtgccaccct taatccccac 660
aagcgagttc ctccgcaatt cgcctgtccc actctcaact ttcttcaac tgactctttg 720 ctgtggtccc tcgctgtggc agtggaaaca actaccactg cgaggtaggg aatgtcatga 780
ggggctacct gcagcccttg gcttgcaggg atgcagggat gcggtcggaa cctgaggccc 840
cgcccttctc ttgccccacg ccattaggcc acgcccctac ccagcactcc ttcaaccacc 900
cccttccccg gcgcctcatg aggtcccgcc cctctcaacc ctagctcttg aggcctcccc 960
ttcacagccg ccccggcgtt ccttgacttg aggccacgtc cctctgctcc ttcattccca 1020

```
agaccctacg ctttgcgagt cctccctgtc ctgctgccta ggaccccgcc cctctcagcc   1080

cttctgcccc aagaccccgc cccttaggct gttcccgccc actggccaat gaagacccgc   1140

cctttcttta gccgccccgc cccggtccca caaaatcccg cctccggccc cgcctcccgc   1200

ccccttgggc gctccgtagc agtgacgtgc gcaggctggg cactctgcag ggctctctgg   1260

ccggcgggtg gagaccgatc cgggatctgt cccagcagga agcgtatccc ggccgccgtc   1320

gtgctgtcgt ctccggtgct cgctctcggc cgcggtgtcg cgcttgccct tcgcgcccgc   1380

agcccggcag cctctcgagc tcaagcttcg aattcgtcga caggatgttg caaatccaag   1440

tggaggagaa agaagaggat acagaggaaa gctcaagtga agaagaagaa gataagctac   1500

ccagaagaga gagcttgaga ccaaagagga aacggaccag agatgtcatc aatgaggatg   1560

acccagaacc ggagccggag gatgaagaaa caagaaaggc aagagaaaaa gaaaggcgga   1620

ggaggctgcg gagaggagcg gaagaagaag aagaaattga tgaagaggaa ttagaacggt   1680

taaaagcact gctcgatgag aatagacaaa tgatcgctac tgtcaaatgt aaaccttgga   1740

aaatggagaa gaaaattgaa gttctcaagg aagcaaagaa atttgtgagt gagaatgaag   1800

gcgctcttgg gaaaggaaag ggaaagaagt ggtttgcatt taagatgatg atggccaaga   1860

aatgggcaaa attcctccga gattttgaga acttcaaagc ggcttgcgtc ccatgggaaa   1920

acaaaatcaa ggcaattgaa agtcagtttg gttcctcagt ggcctcgtac ttcctgttcc   1980

tcaggtggat gtacggcgtc aacatggttc tctttgtgtt gaccttcagc ctcatcatgt   2040

taccggagta cctctggggt ttaccgtacg gcagcttacc taggaaaaca gtcccaagag   2100

ctgaagaagc atctgcagcc aactttggtg tgttgtatga cttcaatggc ctggcgcagt   2160

actctgtcct cttttatggc tattacgaca ataaacgcac gatcggatgg ctgaatttcc   2220

ggctacctct ttcctacttc ctggtgggga ttatgtgcat tggatacagc ttcctggttg   2280

tcctcaaagc gatgaccaaa aatattggtg acgatggtgg tggcgatgac aacactttca   2340

acttcagctg gaaggtgttc tgtagctggg actatctgat tggtaaccct gaaacagccg   2400

acaacaagtt taactctatc acgatgaact ttaaggaagc catcatagaa gagagagccg   2460

cacaggtgga ggagaacatc cacctcatca gatttctgag gtttctcgct aacttcttcg   2520

tgttcctcac acttggtgca agtggatacc tcatcttttg ggctgtgaag cgatcccagg   2580

agttcgccca gcaagatcct gacacccttg ggtggtggga aaaaaatgaa atgaacatgg   2640

taatgtccct cctggggatg ttctgtccca ccctgtttga cttatttgct gaactggaag   2700

attaccatcc tctcattgct ctgaagtggc tcctggggcg catttttgct cttcttctag   2760

gcaacttgta tgtattcatt ctcgccttga tggatgagat taacaacaag attgaagagg   2820

agaagcttgt gaaggccaat attaccctgt gggaagccaa catgattaag gcttacaatg   2880

aatctctctc tgggctctct gggaacacca caggagcacc ctttttcgtt catcctgcag   2940

atgtccctcg cggtccctgc tgggaaacaa tggtggggca ggaattcgtg cgtctcaccg   3000

tttctgacgt cctgaccact tacgtcacga tcctcattgg cgacttcctc agagcatgtt   3060

tcgtgaggtt ctgcaattac tgctggtgct gggacttaga atatggatat ccttcataca   3120

cagaattcga catcagtggc aacgtcctcg ctctgatctt caaccaaggc atgatctgga   3180

tgggctcctt cttcgctcct agcctcccgg gcatcaacat cctccgtctc cacacatcca   3240

tgtatttcca gtgctgggct gtgatgtgct gcaatgttcc cgaggccagg gtgttcaaag   3300

cttccagatc caacaacttc tacctcggca tgctgctact catcctcttc ctgtccacca   3360

tgccggtcct gtacatgatc gtctccctcc cgccatcttt tgattgtggg cccttcagtg   3420
```

```
gtaaaaacag gatgtttgaa gtcatcggtg agaccctgga acatgacttc ccaagctgga   3480
tggcgaagat cctgaggcag ctttctaacc ccggccttgt cattgctgtc attctggtga   3540
tggttctgac catctattat ctcaatgcta ctgccaaggg ccagaaagca gcgaatctgg   3600
acctcaaaaa gaagatgaaa cagcaagctt tggagaacaa aatgcgaaac aagaaaatgg   3660
cagcggctcg agcagctgca gctgctggtg gccagtggat ccaccggccg gtcgccacca   3720
tggtgagcaa gggcgaggag ctgttcaccg gggtggtgcc catcctggtc gagctggacg   3780
gcgacgtaaa cggccacaag ttcagcgtgt ccggcgaggg cgagggcgat gccacctacg   3840
gcaagctgac cctgaagttc atctgcacca ccggcaagct gcccgtgccc tggcccaccc   3900
tcgtgaccac cctgacctac ggcgtgcagt gcttcagccg ctaccccgac cacatgaagc   3960
agcacgactt cttcaagtcc gccatgcccg aaggctacgt ccaggagcgc accatcttct   4020
tcaaggacga cggcaactac aagacccgcg ccgaggtgaa gttcgagggc gacaccctgg   4080
tgaaccgcat cgagctgaag ggcatcgact tcaaggagga cggcaacatc ctggggcaca   4140
agctggagta caactacaac agccacaacg tctatatcat ggccgacaag cagaagaacg   4200
gcatcaaggt gaacttcaag atccgccaca acatcgagga cggcagcgtg cagctcgccg   4260
accactacca gcagaacacc cccatcggcg acggccccgt gctgctgccc gacaaccact   4320
acctgagcac ccagtccgcc ctgagcaaag accccaacga gaagcgcgat cacatggtcc   4380
tgctggagtt cgtgaccgcc gccgggatca ctctcggcat ggacgagctg tacaagtaag   4440
cggccgctcg agcctaagct tctagaagat ctacgggtgg catccctgtg acccctcccc   4500
agtgcctctc ctggccctgg aagttgccac tccagtgccc accagccttg tcctaataaa   4560
attaagttgc atcattttgt ctgactaggt gtccttctat aatattatgg ggtggagggg   4620
ggtggtatgg agcaaggggc aagttgggaa gacaacctgt agggcctgcg gggtctattg   4680
ggaaccaagc tggagtgcag tggcacaatc ttggctcact gcaatctccg cctcctgggt   4740
tcaagcgatt ctcctgcctc agcctcccga gttgttggga ttccaggcat gcatgaccag   4800
gctcagctaa tttttgtttt tttggtagag acggggtttc accatattgg ccaggctggt   4860
ctccaactcc taatctcagg tgatctaccc accttggcct cccaaattgc tgggattaca   4920
ggcgtgaacc actgctccct tccctgtcct tctgattttg taggtaacca cgtgcggacc   4980
gagcggccgc aggaacccct agtgatggag ttggccactc cctctctgcg cgctcgctcg   5040
ctcactgagg ccgggcgacc aaaggtcgcc cgacgcccgg gctttgcccg ggcggcctca   5100
gtgagcgagc gagcgcgcag ctgcctgcag gggcgcctga tgcggtattt tctccttacg   5160
catctgtgcg gtatttcaca ccgcatacgt caaagcaacc atagtacgcg ccctgtagcg   5220
gcgcattaag cgcggcgggt gtggtggtta cgcgcagcgt gaccgctaca cttgccagcg   5280
ccctagcgcc cgctcctttc gctttcttcc cttcctttct cgccacgttc gccggctttc   5340
cccgtcaagc tctaaatcgg gggctccctt tagggttccg atttagtgct ttacggcacc   5400
tcgaccccaa aaaacttgat ttgggtgatg gttcacgtag tgggccatcg ccctgataga   5460
cggtttttcg ccctttgacg ttggagtcca cgttctttaa tagtggactc ttgttccaaa   5520
ctggaacaac actcaaccct atctcgggct attcttttga tttataaggg attttgccga   5580
tttcggccta ttggttaaaa aatgagctga tttaacaaaa atttaacgcg aattttaaca   5640
aaatattaac gtttacaatt ttatggtgca ctctcagtac aatctgctct gatgccgcat   5700
agttaagcca gccccgacac ccgccaacac ccgctgacgc gccctgacgg gcttgtctgc   5760
```

```
tcccggcatc cgcttacaga caagctgtga ccgtctccgg gagctgcatg tgtcagaggt   5820

tttcaccgtc atcaccgaaa cgcgcgagac gaaagggcct cgtgatacgc ctatttttat   5880

aggttaatgt catgataata atggtttctt agacgtcagg tggcactttt cggggaaatg   5940

tgcgcggaac ccctatttgt ttatttttct aaatacattc aaatatgtat ccgctcatga   6000

gacaataacc ctgataaatg cttcaataat attgaaaaag gaagagtatg agtattcaac   6060

atttccgtgt cgcccttatt cccttttttg cggcattttg ccttcctgtt tttgctcacc   6120

cagaaacgct ggtgaaagta aaagatgctg aagatcagtt gggtgcacga gtgggttaca   6180

tcgaactgga tctcaacagc ggtaagatcc ttgagagttt tcgccccgaa gaacgttttc   6240

caatgatgag cacttttaaa gttctgctat gtggcgcggt attatcccgt attgacgccg   6300

ggcaagagca actcggtcgc cgcatacact attctcagaa tgacttggtt gagtactcac   6360

cagtcacaga aaagcatctt acggatggca tgacagtaag agaattatgc agtgctgcca   6420

taaccatgag tgataacact gcggccaact tacttctgac aacgatcgga ggaccgaagg   6480

agctaaccgc ttttttgcac aacatggggg atcatgtaac tcgccttgat cgttgggaac   6540

cggagctgaa tgaagccata ccaaacgacg agcgtgacac cacgatgcct gtagcaatgg   6600

caacaacgtt gcgcaaacta ttaactggcg aactacttac tctagcttcc cggcaacaat   6660

taatagactg gatggaggcg gataaagttg caggaccact tctgcgctcg gcccttccgg   6720

ctggctggtt tattgctgat aaatctggag ccggtgagcg tgggtctcgc ggtatcattg   6780

cagcactggg gccagatggt aagccctccc gtatcgtagt tatctacacg acggggagtc   6840

aggcaactat ggatgaacga aatagacaga tcgctgagat aggtgcctca ctgattaagc   6900

attggtaact gtcagaccaa gtttactcat atatacttta gattgattta aaacttcatt   6960

tttaatttaa aaggatctag gtgaagatcc tttttgataa tctcatgacc aaaatccctt   7020

aacgtgagtt ttcgttccac tgagcgtcag accccgtaga aaagatcaaa ggatcttctt   7080

gagatccttt ttttctgcgc gtaatctgct gcttgcaaac aaaaaaacca ccgctaccag   7140

cggtggtttg tttgccggat caagagctac caactctttt tccgaaggta actggcttca   7200

gcagagcgca gataccaaat actgtccttc tagtgtagcc gtagttaggc caccacttca   7260

agaactctgt agcaccgcct acatacctcg ctctgctaat cctgttacca gtggctgctg   7320

ccagtggcga taagtcgtgt cttaccgggt tggactcaag acgatagtta ccggataagg   7380

cgcagcggtc gggctgaacg gggggttcgt gcacacagcc cagcttggag cgaacgacct   7440

acaccgaact gagataccta cagcgtgagc tatgagaaag cgccacgctt cccgaaggga   7500

gaaaggcgga caggtatccg gtaagcggca gggtcggaac aggagagcgc acgagggagc   7560

ttccaggggg aaacgcctgg tatctttata gtcctgtcgg gtttcgccac ctctgacttg   7620

agcgtcgatt tttgtgatgc tcgtcagggg ggcggagcct atggaaaaac gccagcaacg   7680

cggccttttt acggttcctg gccttttgct ggccttttgc tcacatgt                7728
```

<210> SEQ ID NO 8
<211> LENGTH: 7380
<212> TYPE: DNA
<213> ORGANISM: Artificial Sequence
<220> FEATURE:
<223> OTHER INFORMATION: synthetic expression construct

<400> SEQUENCE: 8

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120
```

```
actccatcac taggggttcc tgcggccgca cgcgtgcaag aaccctcact ggctgaacta    180
tcttgccagc cccttatttt gttttcatat taacctcttt tttctagtaa aggagatgtt    240
tgctctcaaa tttgcatagg aatgtaatat ttaatttaaa aagatgaccc acatatgacc    300
ttataaggac agtaaaatta aacaaccgga aagataaagc gggccagttg gctcagttct    360
ataaaaccag cccacaagga ttgtcactat tcttaggctt gcgcgggcta catgatgagt    420
tccaggactg cctggttaca gaccgagact ctctcaagag tccagataaa caacaacaaa    480
gggggcgagg tggaaataca ggggctgtaa gaagtaaata tgatatctgc atgggaggct    540
agccagagaa gaaaaaattt tcttccgtgg ttcaatcctc caagggctga acaggaagtt    600
gacgcaggca ggtgaggagc acgagcctag atggctgcg gtgccaccct taatccccac     660
aagcgagttc ctccgcaatt cgcctgtccc actctcaact tttcttcaac tgactctttg    720
ctgtggtccc tcgctgtggc agtggaaaca actaccactg cgaggtaggg aatgtcatga    780
ggggctacct gcagcccttg gcttgcaggg atgcagggat gcggtcggaa cctgaggccc    840
cgcccttctc ttgccccacg ccattaggcc acgcccctac ccagcactcc ttcaaccacc    900
cccttccccg gcgcctcatg aggtcccgcc cctctcaacc ctagctcttg aggcctcccc    960
ttcacagccg ccccggcgtt ccttgacttg aggccacgtc cctctgctcc ttcattccca   1020
agaccctacg ctttgcgagt cctccctgtc ctgctgccta ggaccccgcc cctctcagcc   1080
cttctgcccc aagaccccgc cccttaggct gttcccgccc actggccaat gaagacccgc   1140
cctttcttta gccgccccgc cccggtccca caaaatcccg cctccggccc cgcctcccgc   1200
ccccttgggc gctccgtagc agtgacgtgc gcaggctggg cactctgcag ggctctctgg   1260
ccggcgggtg gagaccgatc cgggatctgt cccagcagga agcgtatccc ggccgccgtc   1320
gtgctgtcgt ctccggtgct cgctctcggc cgcggtgtcg cgcttgccct tcgcgcccgc   1380
agcccggcag cctctcgagc tcaagcttcg aattcgtcga caggatgagc cccagttaa    1440
agagcttgga cgaggaaggt gacaagtcag caagaagacc cacaaggaaa caaacctcca   1500
gagctgcatg tccccaagac gggcaccgag cccaatctag ccggaaggat cctgctaagg   1560
gtagcccaag accagggtct tcccggaaga aacagatgga acatggaagc tatcacaagg   1620
ggttgcaggg acagaaacca cgaaaggtgg agaggtctct acaagggagg aagaaggatc   1680
ggagaacttc ccttaaggag cagagagcat ctccaaagaa ggagagggag gctctgagga   1740
aggaggcagg caagcagctg agaaaaccca ggtccacttc cttgggctcc agtgtctcta   1800
ctggagactc cctgtctgag gaggagctgg ctcagatcct ggaacaggta gaagaaaaaa   1860
agaagctcat cactaccgtg aggaacaaac cctggcccat ggcaaagaag ctgagggaac   1920
tcagggaagc ccaagccttt gtggagaagt atgaaggagc cttggggaaa ggcaagggca   1980
aacacctcta cgcctacagg atgatgatgg ctaagaaatg ggtcaagttt aagagggact   2040
ttgataattt caagactcaa tgtattccct gggaaatgaa gatcaaggac attgaaagtc   2100
acttcggttc ttctgtggca tcttacttca tctttctccg atggatgtat ggagttaacc   2160
ttgtcctttt tggcttaata tttggtctag tcatcatccc agaggtgctg atgggcatgc   2220
cctatggaag tatacccaga aagacggtgc ctcgggctga ggaagagcga gccatggact   2280
tctctgtcct ttgggatttt gagggctaca tcaaatattc tgctctcttc tatggctact   2340
acaacaacca gcggaccatt ggatggctga ggtacaggct gcccatggct tactttatgg   2400
tgggggtcag cgtgtttggc tacagcttga tgatcgtcat taggtcgatg gccagcaata   2460
```

```
cccagggtag caccagtgag ggggacagtg acagcttcac gttcagcttc aagatgttca   2520
ccagctggga ctacctcatc gggaattcag agacagcaga caacaaatat gtctccatca   2580
ctaccagctt caaggagtct atagtggacg aacaagagag taacaaagaa gggaatatcc   2640
acctgacaag attcctccgc gtcctggcca actttctcat tctctgctgt ctgtgtggaa   2700
gcgggtacct catttacttt gtggtgaaac ggtcccagga gttctccaaa atgcaaaatg   2760
tcagctggta tgaaaggaat gaggtggaga tcgtgatgtc tctgctaggg atgttttgtc   2820
cccctctgtt tgaaaccatc gctgccttgg agaattatca cccacgaact gggctgaagt   2880
ggcagctggg ccgcatcttt gcccttttcc tgggaaacct ctacacgttt ctcctggccc   2940
tcatggacga tgtccacctt aagctttcta atgaggaaaa aatcaagaac atcactcact   3000
ggaccctgtt taactattac aattcctcag gtgggaatga gagtgtgccc cggccaccac   3060
cacaccctgc agatgtgccc agaggttctt gctgggagac agctgtgggc attgagttta   3120
tgaggctcac cgtgtctgac atgctggtaa catacctcac catcttggtc ggagatttcc   3180
tccgagcttg ttttgtccgg ttcatgaatc actgctggtg ttgggacctc gaggctggtt   3240
ttccctcata tgccgagttt gatattagtg gaaatgtgtt gggtttgatc ttcaaccaag   3300
gaatgatctg gatgggctcc ttctatgctc caggactggt gggcatcaat gtcctgcgcc   3360
tgttgacctc catgtacttc cagtgctggg cagtgatgag cagcaacgtt ccccatgagc   3420
gtgtgtttaa agcctcccga tccaacaact tctacatggg cctgctgctg ttggtgctct   3480
tcctcagcct cctgcctgtg gcctacactg tcatgtctct cccaccctcg tttgactgtg   3540
gccccttcag tgggaaaaac agaatgtacg atgtcctcca tgagaccatc gagaacgatt   3600
tccctaagtt cctgggcaag atctttgcgt tccttgccaa cccaggcctg atcattccag   3660
ccatcctgct aatgtttctg gccatttact acctgaactc agtttcaaaa agtctttcca   3720
gagctaatgc ccagctgcga aagaagatcc aagcgctccg tgaagttgag aagaaccata   3780
aatccatcaa gggaaaagcc atagtcacat attcagagga cacaatcaag aacagctcca   3840
aaaatgccac ccagatacat cttactaaag aagagcccac atctcactct tccagccaaa   3900
tccagaccct ggacaagaaa gcgcagggcc cccacacctc cagtactgag ggtggggcct   3960
cgccgtctac ctcctggcac catgttgggt ctcaaccacc gagaggcaga cgagattctg   4020
gccaacccca gtctcagact tatacaggca ggtcaccttc tggaaagaga acccagaggc   4080
ctcacaactg agcggccgct cgagcctaag cttctagaag atctacgggt ggcatccctg   4140
tgacccctcc ccagtgcctc tcctggccct ggaagttgcc actccagtgc ccaccagcct   4200
tgtcctaata aaattaagtt gcatcatttt gtctgactag gtgtccttct ataatattat   4260
ggggtggagg ggggtggtat ggagcaaggg gcaagttggg aagacaacct gtagggcctg   4320
cggggtctat tgggaaccaa gctggagtgc agtggcacaa tcttggctca ctgcaatctc   4380
cgcctcctgg gttcaagcga ttctcctgcc tcagcctccc gagttgttgg gattccaggc   4440
atgcatgacc aggctcagct aatttttgtt tttttggtag agacggggtt tcaccatatt   4500
ggccaggctg gtctccaact cctaatctca ggtgatctac ccaccttggc ctcccaaatt   4560
gctgggatta caggcgtgaa ccactgctcc cttccctgtc cttctgattt tgtaggtaac   4620
cacgtgcgga ccgagcggcc gcaggaaccc ctagtgatgg agttggccac tccctctctg   4680
cgcgctcgct cgctcactga ggccgggcga ccaaaggtcg cccgacgccc gggctttgcc   4740
cgggcggcct cagtgagcga gcgagcgcgc agctgcctgc aggggcgcct gatgcggtat   4800
tttctcctta cgcatctgtg cggtatttca caccgcatac gtcaaagcaa ccatagtacg   4860
```

-continued

```
cgccctgtag cggcgcatta agcgcggcgg gtgtggtggt tacgcgcagc gtgaccgcta   4920
cacttgccag cgccctagcg cccgctcctt tcgctttctt cccttccttt ctcgccacgt   4980
tcgccggctt tccccgtcaa gctctaaatc gggggctccc tttagggttc cgatttagtg   5040
ctttacggca cctcgacccc aaaaaacttg atttgggtga tggttcacgt agtgggccat   5100
cgccctgata gacggttttt cgccctttga cgttggagtc cacgttcttt aatagtggac   5160
tcttgttcca aactggaaca acactcaacc ctatctcggg ctattctttt gatttataag   5220
ggattttgcc gatttcggcc tattggttaa aaaatgagct gatttaacaa aaatttaacg   5280
cgaattttaa caaaatatta acgtttacaa ttttatggtg cactctcagt acaatctgct   5340
ctgatgccgc atagttaagc cagccccgac acccgccaac acccgctgac gcgccctgac   5400
gggcttgtct gctcccggca tccgcttaca gacaagctgt gaccgtctcc gggagctgca   5460
tgtgtcagag gttttcaccg tcatcaccga aacgcgcgag acgaaagggc ctcgtgatac   5520
gcctattttt ataggttaat gtcatgataa taatggtttc ttagacgtca ggtggcactt   5580
ttcggggaaa tgtgcgcgga acccctattt gtttattttt ctaaatacat tcaaatatgt   5640
atccgctcat gagacaataa ccctgataaa tgcttcaata atattgaaaa aggaagagta   5700
tgagtattca acatttccgt gtcgccctta ttcccttttt tgcggcattt tgccttcctg   5760
tttttgctca cccagaaacg ctggtgaaag taaaagatgc tgaagatcag ttgggtgcac   5820
gagtgggtta catcgaactg gatctcaaca gcggtaagat ccttgagagt tttcgccccg   5880
aagaacgttt tccaatgatg agcactttta aagttctgct atgtggcgcg gtattatccc   5940
gtattgacgc cgggcaagag caactcggtc gccgcataca ctattctcag aatgacttgg   6000
ttgagtactc accagtcaca gaaaagcatc ttacggatgg catgacagta agagaattat   6060
gcagtgctgc cataaccatg agtgataaca ctgcggccaa cttacttctg acaacgatcg   6120
gaggaccgaa ggagctaacc gcttttttgc acaacatggg ggatcatgta actcgccttg   6180
atcgttggga accggagctg aatgaagcca taccaaacga cgagcgtgac accacgatgc   6240
ctgtagcaat ggcaacaacg ttgcgcaaac tattaactgg cgaactactt actctagctt   6300
cccggcaaca attaatagac tggatggagg cggataaagt tgcaggacca cttctgcgct   6360
cggcccttcc ggctggctgg tttattgctg ataaatctgg agccggtgag cgtgggtctc   6420
gcggtatcat tgcagcactg gggccagatg gtaagccctc ccgtatcgta gttatctaca   6480
cgacggggag tcaggcaact atggatgaac gaaatagaca gatcgctgag ataggtgcct   6540
cactgattaa gcattggtaa ctgtcagacc aagtttactc atatatactt tagattgatt   6600
taaaacttca tttttaattt aaaaggatct aggtgaagat cctttttgat aatctcatga   6660
ccaaaatccc ttaacgtgag ttttcgttcc actgagcgtc agaccccgta gaaaagatca   6720
aaggatcttc ttgagatcct ttttttctgc gcgtaatctg ctgcttgcaa acaaaaaaac   6780
caccgctacc agcggtggtt tgtttgccgg atcaagagct accaactctt tttccgaagg   6840
taactggctt cagcagagcg cagataccaa atactgtcct tctagtgtag ccgtagttag   6900
gccaccactt caagaactct gtagcaccgc ctacatacct cgctctgcta atcctgttac   6960
cagtggctgc tgccagtggc gataagtcgt gtcttaccgg gttggactca agacgatagt   7020
taccggataa ggcgcagcgg tcgggctgaa cggggggttc gtgcacacag cccagcttgg   7080
agcgaacgac ctacaccgaa ctgagatacc tacagcgtga gctatgagaa agcgccacgc   7140
ttcccgaagg gagaaaggcg gacaggtatc cggtaagcgg cagggtcgga acaggagagc   7200
```

gcacgaggga gcttccaggg ggaaacgcct ggtatcttta tagtcctgtc gggtttcgcc 7260
acctctgact tgagcgtcga tttttgtgat gctcgtcagg ggggcggagc ctatggaaaa 7320
acgccagcaa cgcggccttt ttacggttcc tggccttttg ctggcctttt gctcacatgt 7380

<210> SEQ ID NO 9
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 9
gaggtaccat ggaccggaag gtggcccgag 30

<210> SEQ ID NO 10
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 10
caggatccgg acaatttcat cccctac 27

<210> SEQ ID NO 11
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 11
ctcattgaaa atgacgcaga gaagg 25

<210> SEQ ID NO 12
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 12
tctcactttg atggacacgg tctt 24

<210> SEQ ID NO 13
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 13
gaacccaacc gcctgccg 18

<210> SEQ ID NO 14
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 14
tgcagacggt ccaagcgt 18

-continued

```
<210> SEQ ID NO 15
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 15

gtgaggccgg tgctgagtat g                                               21


<210> SEQ ID NO 16
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 16

gccaaagttg tcatggatga c                                               21


<210> SEQ ID NO 17
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 17

catctgcagc caactttggt gtgt                                            24


<210> SEQ ID NO 18
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 18

agaggtagcc ggaaattcag ccat                                            24


<210> SEQ ID NO 19
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 19

tgagcgcaag tactctgtgt ggat                                            24


<210> SEQ ID NO 20
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 20

actcatcgta ctcctgcttg ctga                                            24
```

MATERIALS AND METHODS FOR DELIVERING NUCLEIC ACIDS TO COCHLEAR AND VESTIBULAR CELLS

CROSS REFERENCE TO RELATED APPLICATIONS

This application is a continuation of U.S. application Ser. No. 16/060,841, filed Jun. 8, 2018, which is a § 371 National Stage Application of PCT/US2016/066225, filed Dec. 12, 2016, which claims the benefit of priority under 35 U.S.C. § 119(e) to U.S. Application No. 62/266,462, filed Dec. 11, 2015 and U.S. Application No. 62/266,477, filed Dec. 11, 2015.

SEQUENCE LISTING

This application contains a Sequence Listing that has been submitted electronically as an ASCII text file named "Sequence_Listing.txt." The ASCII text file, created on Oct. 5, 2021, is 73 KB in size. The material in the ASCII text file is hereby incorporated by reference in its entirety.

TECHNICAL FIELD

This disclosure generally relates to materials and methods for delivering nucleic acids to cochlear and vestibular cells.

BACKGROUND

Genetically-based hearing loss is a significant problem with few therapeutic options other than cochlear implants. Inherited hearing problems are often due to single gene defects. Prelingual deafness is diagnosed in 1/500 infants, of which about 50% have a genetic etiology. Usher syndrome, which is associated with a number of different clinical subtypes, each of which can be caused by a mutation in any of a number of different genes, is responsible for 3 to 6% of early childhood deafness, while one of the more prevalent genetic defects, estimated to be 1-2% of all genetic deafness, occurs in the TMC1 gene.

The inner ear, e.g., cochlea, particularly the inner and outer hair cells (IHCs and OHCs) in the cochlea, is an attractive target for gene therapy approaches to intervene in hearing loss and deafness of various etiologies, most immediately monogenic forms of inherited deafness. However, it has been a challenge to efficiently target and transduce IHCs and OHCs as well as other inner ear cells that may be relevant to gene therapy approaches.

SUMMARY

Hearing loss is the most common sensory disorder worldwide, with half of pre-lingual deafness due to genetic causes. Nonetheless, translation of cochlear gene therapy to the clinic has been slowed by lack of safe, clinically relevant, and efficient delivery modalities. The novel gene delivery modalities described herein, however, which include new compositions and methods based on an adeno-associated virus (AAV) containing an Anc80 capsid protein, provide highly efficient gene transfer to inner ear cells including both IHCs and OHCs. As shown herein, an adeno-associated virus (AAV) containing an ancestral scaffold capsid protein referred to as Anc80 or a specific Anc80 capsid protein (e.g., Anc80-0065) is surprisingly efficient at targeting various cells in the inner ear in vivo, including both IHCs and OHCs.

In one aspect, an AAV vector is provided that includes an Anc80 capsid protein and a TMC1 or TMC2 transgene. In another aspect, an AAV vector is provided that includes an Anc80 capsid protein and one or more transgenes selected from the group consisting of MYO7A, USCH1C, CDH23, PCDH15, SANS, CIB2, USH2A, VLGR1, WHRN, CLRN1, PDZD7. In one embodiment, the AAV vector further comprises a heterologous promoter.

In yet another aspect, a method of delivering a transgene to one or more cells in the inner ear in a subject is provided. Such a method typically includes administering an adeno-associated virus (AAV) to the inner ear in a subject, wherein the AAV comprises an Anc80 capsid protein and a transgene.

In still another aspect, a method of treating a hearing disorder (e.g., hearing restoration) or preventing hearing loss (or further hearing loss) in a subject is provided. Such a method typically includes administering an AAV to the subject, wherein the AAV comprises an Anc80 capsid protein and a transgene that, when expressed in one or more cells in the inner ear, restores hearing to the subject.

In one embodiment, the one or more cells in the inner ear are selected from the group consisting of inner hair cells (IHCs) and outer hair cells (OHCs). In some embodiments, the transgene is delivered to at least 80% of inner hair cells and at least 80% of outer hair cells. In some embodiments, the one or more cells in the inner ear are selected from the group consisting of spiral ganglion neurons, vestibular hair cells, vestibular ganglion neurons, supporting cells, and cells in the stria vascularis.

In some embodiments, the transgene is selected from the group consisting of ACTG1, ADCY1, ATOHI, ATP6V1B1, BDNF, BDP1, BSND, DATSPER2, CABP2, CD164, CDC14A, CDH23, CEACAM16, CHD7, CCDC50, CIB2, CLDN14, CLIC5, CLPP, CLRN1, COCH, COL2A1, COL4A3, COL4A4, COL4A5, COL9A1, COL9A2, COL11A1, COL11A2, CRYM, DCDC2, DFNA5, DFNB31, DFNB59, DIAPH1, EDN3, EDNRB, ELMOD3, EMOD3, EPS8, EPS8L2, ESPN, ESRRB, EYA1, EYA4, FAM65B, FOXI1, GIPC3, GJB2, GJB3, GJB6, GPR98, GRHL2, GPSM2, GRXCR1, GRXCR2, HARS2, HGF, HOMER2, HSD17B4, ILDR1, KARS, KCNE1, KCNJ10, KCNQ1, KCNQ4, KITLG, LARS2, LHFPL5, LOXHD1, LRTOMT, MARVELD2, MCM2, MET, MIR183, MIRN96, MITF, MSRB3, MT-RNR1, MT-TS1, MYH14, MYH9, MYO15A, MYO1A, MYO3A, MYO6, MYO7A, NARS2, NDP, NF2, NT3, OSBPL2, OTOA, OTOF, OTOG, OTOGL, P2RX2, PAX3, PCDH15, PDZD7, PJVK, PNPT1, POLR1D, POLR1C, POU3F4, POU4F3, PRPS1, PTPRQ, RDX, S1PR2, SANS, SEMA3E, SERPINB6, SLC17A8, SLC22A4, SLC26A4, SLC26A5, SIX1, SIX5, SMAC/DIABLO, SNAI2, SOX10, STRC, SYNE4, TBC1D24, TCOF1, TECTA, TIMM8A, TJP2, TNC, TMC1, TMC2, TMIE, TMEM132E, TMPRSS3, TRPN, TRIOBP, TSPEAR, USH1C, USHIG, USH2A, USH2D, VLGR1, WFS1, WHRN, and XIAP.

In some embodiments, the transgene encodes a neurotrophic factor (e.g., GDNF, BDNF, NT3, and HSP70). In some embodiments, the transgene encodes an antibody or fragment thereof. In some embodiments, the transgene encodes an immunomodulatory protein. In some embodiments, the transgene encodes an anti-oncogenic transcript. In some embodiments, the transgene encodes for an antisense, silencing, or long non-coding RNA species. In some embodiments, the transgene encodes a genome editing system selected from the group consisting of a genetically-engineered zinc finger nuclease, TALEN, and CRISPR.

In some embodiments, the Anc80 capsid protein has the sequence shown in SEQ ID NO:1. In some embodiments, the Anc80 capsid protein has the sequence shown in SEQ ID NO:2. In some embodiments, the transgene is under control of a heterologous promoter sequence. Representative heterologous promoter sequences include, without limitation, a CMV promoter, a CBA promoter, a CASI promoter, a PGK promoter, a EF-1 promoter, an alpha9 nicotinic receptor promoter, a prestin promoter, a KCNQ4 promoter, a Myo7a promoter, a Myo6 promoter, a Gfil promoter, a Vglut3 promoter, and an Atoh1 promoter.

In some embodiments, the administering step includes injecting the Anc AAV through the round window. In some embodiments, the Anc AAV is administered via injection through the round window. In some embodiments, the Anc AAV is administered during a cochleostomy or during a canalostomy. In some embodiments, the Anc AAV is administered to the middle ear and/or the round window via one or more drug delivery vehicles.

In some embodiments, expression of the transgene results in regeneration of inner hair cells (IHCs), outer hair cells (OHCs), spiral ganglion neurons, stria vascularis, vestibular hair cells, and/or vestibular ganglion neurons (e.g. Atoh1, NF2), thereby restoring hearing or vestibular function.

In one aspect, an article of manufacture is provided that includes an AAV vector and a pharmaceutical composition. In such an article of manufacture, the AAV vector comprises an Anc80 capsid protein and a transgene operably linked to a promoter. In some embodiments, the transgene is selected from the group consisting of ACTG1, ADCY1, ATOHI, ATP6V1B1, BDNF, BDP1, BSND, DATSPER2, CABP2, CD164, CDC14A, CDH23, CEACAM16, CHD7, CCDC50, CIB2, CLDN14, CLIC5, CLPP, CLRN1, COCH, COL2A1, COL4A3, COL4A4, COL4A5, COL9A1, COL9A2, COL11A1, COL11A2, CRYM, DCDC2, DFNA5, DFNB31, DFNB59, DIAPH1, EDN3, EDNRB, ELMOD3, EMOD3, EPS8, EPS8L2, ESPN, ESRRB, EYA1, EYA4, FAM65B, *FOXI*1, GIPC3, GJB2, GJB3, GJB6, GPR98, GRHL2, GPSM2, GRXCR1, GRXCR2, HARS2, HGF, HOMER2, HSD17B4, ILDR1, KARS, KCNE1, KCNJ10, KCNQ1, KCNQ4, KITLG, LARS2, LHFPL5, LOXHD1, LRTOMT, MARVELD2, MCM2, MET, MIR183, MIRN96, MITF, MSRB3, MT-RNR1, MT-TS1, MYH14, MYH9, MYO15A, MYO1A, MYO3A, MYO6, MYO7A, NARS2, NDP, NF2, NT3, OSBPL2, OTOA, OTOF, OTOG, OTOGL, P2RX2, PAX3, PCDH15, PDZD7, PJVK, PNPT1, POLR1D, POLR1C, POU3F4, POU4F3, PRPS1, PTPRQ, RDX, S1PR2, SANS, SEMA3E, SERPINB6, SLC17A8, SLC22A4, SLC26A4, SLC26A5, SIX1, SIX5, SMAC/DIABLO, SNAI2, SOX10, STRC, SYNE4, TBC1D24, TCOF1, TECTA, TIMM8A, TJP2, TNC, TMC1, TMC2, TMIE, TMEM132E, TMPRSS3, TRPN, TRIOBP, TSPEAR, USH1C, USHIG, USH2A, USH2D, VLGR1, WFS1, WHRN, and XIAP.

In another aspect, a method of delivering a TMC1 or TMC2 transgene to one or more cells in the inner ear in a subject is provided. Such a method typically includes administering an adeno-associated virus (AAV) to the inner ear in a subject, wherein the AAV comprises an Anc80 capsid protein and a transgene. In still another aspect, a method of treating a hearing disorder in a subject is provided. Such a method typically includes administering an AAV to the subject, wherein the AAV comprises an Anc80 capsid protein and a TMC1 or TMC2 transgene that, when expressed in one or more cells in the inner ear, restores hearing to the subject or prevents hearing loss in the subject (e.g., further hearing loss).

In yet another aspect, a method of delivering an Usher transgene to one or more cells in the inner ear in a subject is provided. Such a method typically includes administering an adeno-associated virus (AAV) to the inner ear in a subject, wherein the AAV comprises an Anc80 capsid protein and a transgene. In still another aspect, a method of treating a hearing disorder in a subject is provided. Such a method can include administering an AAV to the subject, wherein the AAV comprises an Anc80 capsid protein and an Usher transgene that, when expressed in one or more cells in the inner ear, restores hearing to the subject. Representative Usher transgenes include, without limitation, MYO7A, USCH1C, CDH23, PCDH15, SANS, CIB2, USH2A, VLGR1, WHRN, CLRN1, PDZD7.

In one embodiment, the one or more cells in the inner ear are selected from the group consisting of inner hair cells (IHCs) and outer hair cells (OHCs). In one embodiment, the transgene is delivered to at least 80% of inner hair cells and at least 80% of outer hair cells. In one embodiment, the one or more cells in the inner ear are selected from the group consisting of spiral ganglion neurons, vestibular hair cells, vestibular ganglion neurons, supporting cells and cells in the stria vascularis.

In one embodiment, the Anc80 capsid protein has the sequence shown in SEQ ID NO: 1. In one embodiment, the Anc80 capsid protein has the sequence shown in SEQ ID NO:2. In one embodiment, the transgene is under control of a heterologous promoter sequence. Representative heterologous promoter sequences include, without limitation, a CMV promoter, a CBA promoter, a CASI promoter, a PGK promoter, a EF-1 promoter, an alpha9 nicotinic receptor promoter, a prestin promoter, a KCNQ4 promoter, a Myo7a promoter, a Myo6 promoter, a Gfil promoter, a Vglut3 promoter, and an Atoh1 promoter.

In one embodiment, the administering step comprises injecting the Anc AAV through the round window. In one embodiment, the Anc AAV is administered via injection through the round window. In one embodiment, the Anc AAV is administered during a cochleostomy or during a canalostomy. In one embodiment, the Anc AAV is administered to the middle ear and/or the round window via one or more drug delivery vehicles.

In one embodiment, expression of the transgene results in regeneration of inner hair cells (IHCs), outer hair cells (OHCs), spiral ganglion neurons, stria vascularis, vestibular hair cells, and/or vestibular ganglion neurons (e.g. Atoh1, NF2), thereby restoring hearing or vestibular function and/or preventing hearing loss (e.g., further hearing loss).

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

Part 1: Highly Efficient Cochlear Gene Transfer

FIGS. 1A-1G show expression at the cochlear base for all serotypes, and apex and base for the indicated AAV. Scale bar=100 μM. Top: Myo7A+TuJ1; bottom: eGFP only; middle: overlay; S. Cells: supporting cells, OHC: outer hair cell, IHC: inner hair cell. FIGS. 1H-1K are graphs showing the percentage of eGFP-positive hair cells per 100 μM after 48 h or 48 h+5 days of incubation. N=3 for 48 h, and N=2 for 48h+5 d. Error bars represent standard error of the mean (SEM).

FIG. 2A are confocal images of mouse organs of Corti, counterstained with Alexa-546-phalloidin (red) and imaged for eGFP (green). Scale bar=50 μm. FIG. 2B is a graph showing quantification of eGFP-positive IHCs in the base and apex of AAV-eGFP injected cochleae. FIG. 2C is a graph showing quantification of eGFP-positive OHCs in the base and apex of AAV-eGFP injected cochleae. FIG. 2D are images showing families of sensory transduction currents recorded at P7 (left) from eGFP-negative OHCs (black) and eGFP-positive OHCs (green). Vertical scale bar indicates 200 pA; horizontal scale bar indicates 20 msec. Currents from eGFP negative (black) and eGFP-positive (green) P35 IHCs are shown on the right. Vertical scale bar indicates 100 pA; horizontal scale bar indicates 20 msec. FIG. 2E is a graph showing sensory transduction current amplitudes plotted for 103 IHCs and OHCs at the ages indicated at the bottom. Data from eGFP-negative (black) and eGFP-positive (green) are shown. The numbers of cells in each group are shown on the graph. FIG. 2F is a graph showing the mean±standard deviation (SD). ABR thresholds plotted for four Anc80-injected ears (green) and four uninjected ears (black) together with data from one injected ear that had no eGFP fluorescence due to injection-related damage (red). FIG. 2G is a graph showing the mean±SD. DPOAE thresholds are plotted for four Anc80-injected ears (green) and four uninjected ears (black) and one negative control ear with injection damage without eGFP fluorescence (red). Injection titers for data points in FIGS. 2B-2G are as in FIG. 2A.

FIG. 3A are images showing mouse utricle from a P1 mouse injected with 1 μL Anc80-eGFP ($1.7\times10^{12}$ GC/mL). The tissue was harvested, fixed and stained with Alexa546-phalloidin (red) and imaged for eGFP (green). Scale bar=100 μm. FIG. 3B are images showing the crista of the posterior semicircular canal from the same mouse described in FIG. 3A. Scale bar=50 μm. FIG. 3C are images showing the sensory epithelium of a human utricle. The tissue was exposed to the Anc80-eGFP vector, cultured, fixed, stained with Alexa546-phalloidin (red) and imaged for eGFP fluorescence (green). Scale bar=100 μm. FIG. 3D are images showing high magnification view of a human epithelium in the utricle stained with Alexa546-phalloidin (red) and Myo7A (blue) and imaged for eGFP (green) transduced in identical conditions as in FIG. 3C. White arrows in the overlay panel indicate selected eGFP-positive/Myo7A-positive cells. Scale bar=20 μm.

FIGS. 4A-4F are images showing results after incubation at equal doses of the AAV serotype. Scale bar=200 μm. The error bars shown in FIGS. 4G-4J represent SEM.

FIG. 8A is an image showing low-magnification of the entire apical portion of a mouse cochlea injected with Anc80-eGFP. The cochlea was harvested and stained with Alexa546-phalloidin (red) and imaged for eGFP (green). Scale bar=100 μm. FIG. 8B is an image showing high magnification view of a basal portion from a different mouse cochlea injected with Anc80-eGFP. The cochlea was harvested and stained with Alexa546-phalloidin (red) and imaged for eGFP (green). Scale bar=20 μm. FIGS. 8C and 8D are graphs showing quantitative comparison of inner and outer hair cell transduction efficiency following round window injection of C57BL/6 mice. FIG. 8E are images showing dose-dependency of Anc80 hair cell transduction. Cochleae were exposed to two different Anc80-eGFP titers, fixed, stained with Alexa546-phalloidin (red) and imaged for eGFP (green). Scale bar=20 μm

FIG. 10C is an image showing anti-AAV neutralizing antibody (NAB) titers in serum and cerebrospinal fluid (CSF) in uninjected and Anc80 RWM-injected animals. Titers reflect the dilution of serum or CSF at which 50% inhibition of transduction was observed in the NAB assay. Due to sample volume limitations, the limit of sensitivity for serum NAB was 1/4 and for CSF was 1/52.5.

FIG. 11A is an image showing expression of eGFP (green) in the vestibular tissue via confocal microscopy with immunofluorescent staining for Myo7A (red). FIG. 11B is a graph showing the mean time until the mice fell off the device+/−SEM. Scale bar=50 μm Part 2—Gene Therapy Restores Function in a Mouse Model of Usher Syndrome FIGS. 12A-12F are images showing basal, middle and apical regions of the organ of Corti imaged in c.216GA and c.216AA mutant mice. FIGS. 12G-12L are high magnification images of OHCs (FIGS. 12G-12H) and IHCs (FIGS. 12I-12J). Stars indicate preserved hair bundles; arrowhead, disorganized hair bundles; and arrows, wavy IHC bundles. Scale bars low mag.: 5 μm (FIGS. 12A-12F); high mag.: 2 μm (FIG. 12G), 3 μm (FIG. 12H), 2 μm (FIGS. 12I-12J) and 1 μm (FIGS. 12K, 12L).

FIGS. 13A-13D are images showing FM1-43 staining to assess the presence of open transduction channels in hair cells of c.216GA and c.216AA mice. IHC FM1-43 fluorescence appears dimmer as IHCs are in a different focal plan. Left: DIC, Right: FM1-43; Scale bar 10 μm; FIG. 13C, scale bar 50 μm; FIG. 13D, scale bar 10 μm. The white line on FIG. 13D delineate the striola (no uptake) and extra-striola regions (uptake). FIGS. 13E-13H are graphs showing mechanotransduction assessed in OHCs, IHCs and VHCs in neonatal c.216GA and c.216AA mice. Representative transduction currents (FIG. 13E), their associated current/displacement plots fitted with a second order Boltzmann function (FIG. 13F) and average peak transduction current are plotted (FIGS. 13G-13H). Average peak transduction was significantly different between the two genotypes in OHCs, IHCs and VHCs (***P<0.01, one-way ANOVA).

FIGS. 14A-14C show acutely dissected inner ear tissue exposed to AAV2/1 vectors, cultured, fixed, counterstained (Alexa Fluor phalloidin, Invitrogen) and imaged with a confocal microscope. FIG. 14A scale bar: 10 μm-upper panels; 5 μm-lower panels; FIG. 14B scale bar: 10 μm; FIG. 14C scale bar: 3 μm; FIG. 14D scale bar: 30 μm; FIG. 14E scale bar: 5 μm.

FIGS. 15A-15C are images showing recovery of mechanotransduction in hair cells of mice injected with Anc80 harmonin vectors. FIGS. 15A-15C show mechanotransduction currents recorded in IHCs of c.216AA uninjected control mice and c.216AA mice injected with Anc80 harmonin-b1 or a combined injection of the Anc80 harmonin-b1 and Anc80 harmonin-a1. Organotypic cultures were prepared and recordings were performed. Corresponding I/X curve for each dataset and double Boltzmann fitting function. Respective maximal mechanotransduction current Imax=102.1 pA (c.216AA); 424.3 pA (c.216AA+harmonin-b1) and 341.1 pA (c.216AA+harmonin-a1&-b1) (FIG. 15B). Average responses (mean±SD) show significant recovery of transduction (*P<0.001) for harmonin-b1 and harmonin-a1+−b1 injected relative to uninjected mice. Average transduction currents were not significantly different in harmonin-b1 injected mice and c.216GA control mice (NS P>0.5). Recovery of mechanotransduction was also not significantly improved when harmonin-a and harmonin-b were combined.

FIG. 16A is an image showing representative ABR responses for 16 kHz tones in c.216AA control mice and c.216AA mice injected with vectors encoding harmonin-a1, harmonin-b1 or a combination of the two. Recovered ABR thresholds near 30 dB SPL were measured in mice injected with harmonin-b1 alone or harmonin-a1 and b1 together. FIG. 16B is an image showing mean ABR responses obtained for: c.216 AA; c.216GA; c.216AA+harmonin-a1; c.216AA+harmonin-b1; c.216AA+harmonin-a1&-b1. Mean±SE, continuous lines. Dotted lines: ABR thresholds for the entire frequency range in mice whose 16 kHz recordings are shown in FIG. 16A. FIG. 16C shows the mean DPOAEs responses obtained for: c.216AA; c.216GA; c.216AA+harmonin-a1; c.216AA+harmonin-b1; c.216AA+harmonin-a1&-b1. Mean±SE, continuous lines. Dotted lines: DPOAEs thresholds for the four mice whose recordings are illustrated in FIG. 16A. Arrows indicate that the thresholds are higher than the maximal stimulus level tested. FIGS. 16D-16E show ABRs and DPOAEs responses obtained at 6 weeks and 3 months in mice that showed initial ABR thresholds under or equal to 45 dB. Six of the eight mice were kept for 6 months and had ABRs and DPOAEs assessed (dotted line). Mean±SE. While ABRs and DPOAEs thresholds shifts were evident over the first three month, hearing rescue was still prominent at 6 months of age in the lower frequency range.

FIG. 17A shows startle response to white noise stimuli recorded in control c.216GA, c.216AA and c.216AA injected mice. Partial startle rescue was evident in mice injected with harmonin-b1 but not harmonin-a1. Averages are shown ±SE. FIG. 17B show rotarod performance in control c.216GA, c.216AA and c.216AA injected mice. Full recovery was observed in mice injected with harmonin-b1 and harmonin-a1/b1; no recovery was observed with harmonin-a1 alone. Averages are shown ±SE. FIGS. 17C-17E show open field observations performed for 5 min in control c.216GA, c.216AA and c.216AA and c.216GA injected mice. Representative tracks over 2.5 min are shown (FIG. 17B). While c.216AA mutant mice explore the entire field and perform repetitive full body rotations, c.216AA mice injected at P1 with harmonin-a1, harmonin-b1 or the combination of the two vectors demonstrate normal behavior similar to their heterozygous c.216GA counterparts or c.216GA mice injected with the truncated vector. FIG. 17C show graphs illustrating the mean±SD for the number of rotations and distance covered per minute. Significant recovery ***P<0.001 was observed between the uninjected and injected mice. Statistical analysis by one-way ANOVA.

FIGS. 19A-19L are images showing analysis of hair bundle morphology in Ush1c c.216G>A mice by SEM. FIGS. 19A-19C show heterozygous c.216GA mice displayed normal hair bundle morphology. FIGS. 19D-19I show disorganized hair bundles observed along the organ of homozygous c.216AA mutant mice. FIGS. 19J-19L show IHCs hair bundle mildly disrupted in c.216AA mice. Distance measured from apex tip: base 3.5-4 mm; mid 1.8-2.2 mm; apex 0.6-0.8 mm. Scale bar low magnification: 5 μm; high magnification: 1 μm.

FIGS. 20A-20J are images showing mechanotranduction properties in c.216AA mutant mice. FIGS. 20A-20E show analysis of mechanotransduction in neonatal OHCs from middle and mid-apical turns of the cochlea. Representative current traces from ~Po=0.5 were fit with a double exponential decay function to assess adaptation in c.216GA and c.216AA mutant (FIG. 20A). Fits were used to generate fast (FIG. 20C) and slow (FIG. 20D) time constants as well as the extent of adaptation (FIG. 20E). The 10-90% operating range was not significantly altered (FIG. 20B). Extent of adaptation in c.216AA mice was significantly less than or heterozygous OHCs as shown in this scatter plot (FIG. 20E). FIGS. 20F-20J show analysis of mechanotransduction in neonatal IHCs. 10-90% operating range values were smaller in c.216GA versus c.216AA IHCs (FIG. 20G). Adaptation was always present albeit slightly slower and with a significant lesser extent in c.216AA IHCs (FIGS. 20H-20J). Statistical analysis is indicated in each plot: *P<0.05, P<0.01 and *P<0.001, one-way ANOVA.

FIGS. 21A-21C are data showing expression of fluorescently labeled harmonin-a and harmonin-b Anc80 vectors at 6 weeks in c.216AA organ of Corti after P1 dual vector injection. FIGS. 21A-21C show confocal images of the basal turn in 6 weeks old c.216AA mice after P1 co-injection of AAV2/Anc80.CMV.tdTomato::harmonin-a1 (0.5 μl; 4.11E^12 gc/ml) and AAV2/Anc80.CMV.eGFP::harmonin-b1 (0.5 μl; 2.99E^12 gc/ml). 69% and 74% of the total number of cells respectively expressed eGFP (FIG. 21A) and tdTomato (FIG. 21C) and 65% expressed both markers demonstrating successful co-transduction. Scale bar: 20 μm.

FIGS. 22A-22F are data showing analysis of ABR response in control c.216GA and injected rescued c.216AA mice. FIGS. 22A and 22D show example of ABR responses at 8 and 16 kHz for control c.216GA and rescued c.216AA mice. FIGS. 22B-22C and 22E-22F show average peak 1 amplitude (FIGS. 22B-22D) and latency (FIGS. 22C-22D) at 8-11.3 and 16 kHz in 6 weeks old mice with comparable thresholds (n=8 c.216GA, n=5 c.216AA+Harmonin-b1 RWM P1). Mean±SE: One-way ANOVA.

FIGS. 23A-23D show the mutant form of harmonin expressed in Ush1c c.216G>A mice does not alter hair cell or auditory function. FIG. 23A is a sequence alignment between the wild-type harmonin-b1 protein and the truncated harmonin that is secreted as a result of the cryptic splicing and frame shift associated with the acadian G>A mutation in exon 3 of the Ush1c gene. FIG. 23B shows semi-quantitative RT-PCR from auditory organs of wild-type mice, c.216GA and c.216AA mutant mice confirms expression of the wild-type (450 bp) and truncated (−35 bp) harmonin in c.216GA and c.216AA mice. FIGS. 23C-23D show auditory brainstem responses (ABR, FIG. 23C) and distortion products (DPOAEs, FIG. 23D) were measured in c.216GA injected mice and control c.216GA and c.216AA mice. Plots are shown as averages ±SE.

FIGS. 24A-24C are images showing recovery of correct Ush1c splicing in the inner ear of 6 weeks old mice injected with AAV2/Anc80.CMV.harmonin-b1. FIG. 24A shows semi-quantitative RT-PCR quantification of correctly spliced (450 bp) and aberrant (415 bp) mRNA from the Ush1c.216A allele shows recovery of correct Ush1c splicing in injected (I) and contralateral ears (FIG. 24C) of c.216AA rescued mice #1 and #2 (35 dB SPL response at 11.3 kHz from injected ears). Mouse #3 with poor ABR response (90 dB SPL at 11.3 kHz) shows modest recovery of correct mRNA expression and mouse #4 (100 dB SPL at 11.3 kHz) shows none. While the correct splice form is not detected in uninjected c.216AA mice (mice #5,6), both the correct and truncated splice forms are detected in c.216GA mice (mice #7,8,9). Corresponding mouse GAPDH shown in the bottom panel was amplified to confirm the relative amount of material. FIG. 24B is an image showing that semi-quantitative radiolabeled PCR analysis confirmed the presence AAV-mUsh1c in injected and contralateral ears of Ush1c.216AA mice. Relative levels of AAV-mUsh1c DNA were present but reduced in mice #3 and #4. FIG. 24C shows relative amount of AAV-mUsh1c correlated with ABR thresholds. Analysis for 11.3 and 16 kHz are illustrated. Linear regressions showed high correlations between the two.

Part 3—Gene Therapy of Additional Mutations Involved in Hearing Loss

FIGS. 26A-26D are representative confocal images of a cochlea from an Ush1c mutant mouse injected through the RWM with of Anc80-Harmonin::GFP (i.e., the GFP is fused to the Harmonin polypeptide), harvested, and stained with actin (red; FIG. 26A), Myo7a (blue; FIG. 26B), and imaged for GFP (green; FIG. 26C). A merged image of FIGS. 26A, 26B, and 26C is shown in FIG. 26D.

Figure 27:
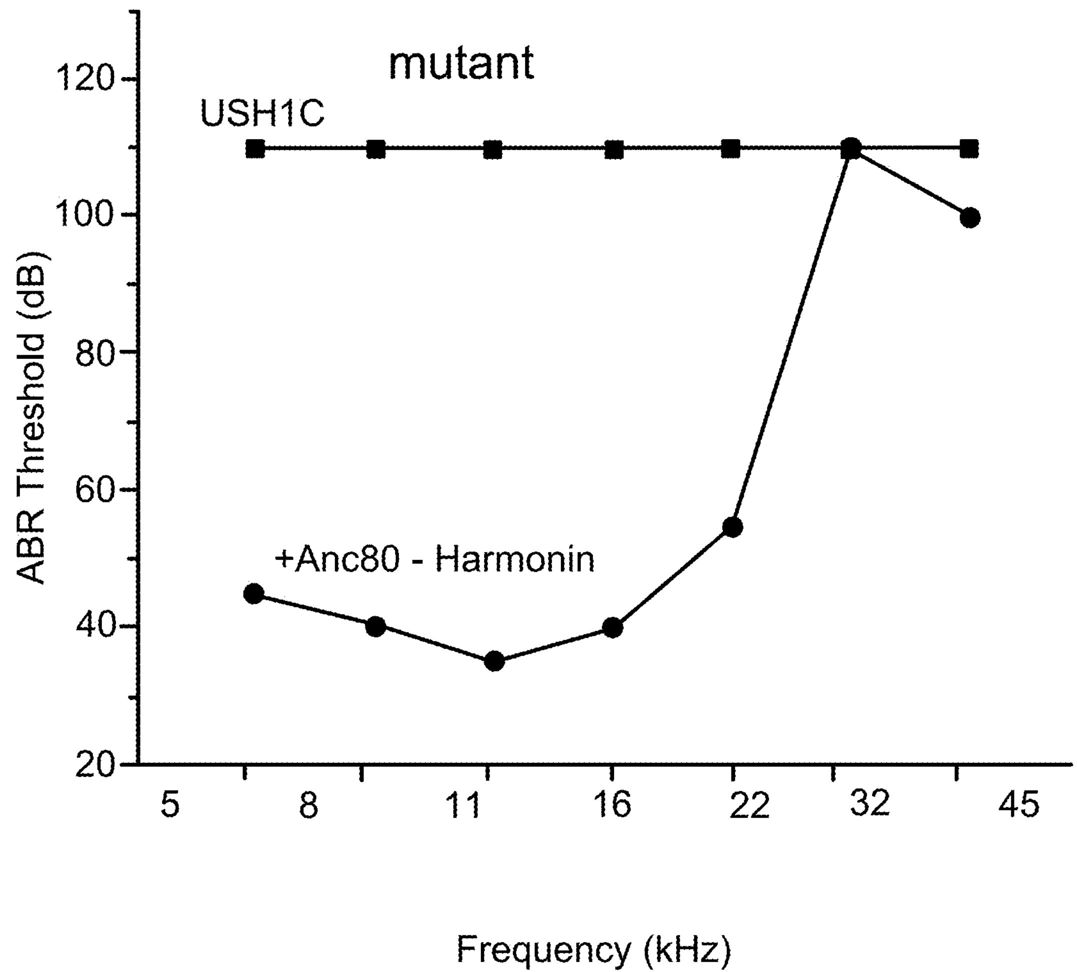

FIG. 27 is a graph showing ABR threshold plotted as a function of sound frequency for an Ush1c mutant mice (squares) and an Ush1c mutant mice injected with an Anc80-Harmonin::GFP vector (circles).

FIGS. 28A-28C show representative confocal images of a KCNQ4−/− cochlea injected through the RWM with Anc80-KCNQ4, harvested, and stained with Alexa 546-phalloidin (red) and an antibody against KCNQ4 (green) at low magnification (FIG. 28A) or high magnification (FIG. 28B) relative to uninjected cochlea at high magnification (FIG. 28C).

FIGS. 29A-29C are a series of graphs that show the KCNQ4 current in a wild type mouse (FIG. 29A), a P10 KCNQ4−/− mouse (FIG. 29B), and a P10 KCNQ4−/− mouse injected with Anc80-KCNQ4 (FIG. 29C). Cochleas were harvested 8 days after injection.

Figure 30:
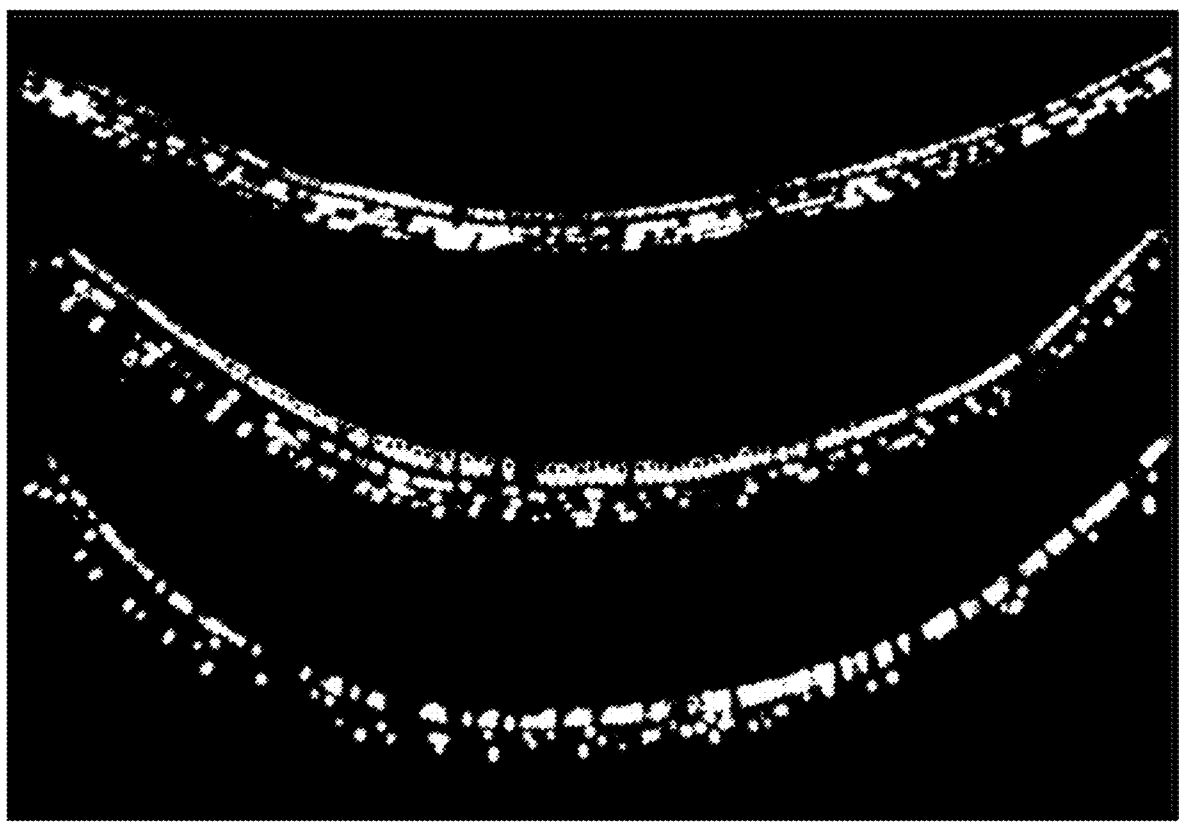

FIG. 30 is a series of three images showing FM1-43 uptake (FM1-43 only permeates functional Tmc1 channels) in Tmc1−/− tissue injected with the Anc80 Tmc1 vector.

FIG. 31A is an image that shows representative families of sensory transduction currents recorded from IHCs of a wild type mouse (left), a Tmc1−/− mouse (middle), and a Tmc1−/− mouse injected with Anc80 Tmc1 (right). Cochleas were harvested 8 days after injection.

FIG. 31B is a graphical representation of the recovery rate of the mice shown in FIG. 31A. The graph in FIG. 31B indicates the percentage of functional cells in a wild type mouse (left), a Tmc1−/− mouse (middle), and a Tmc1−/− mouse injected with Anc80 Tmc1 (right).

Figure 32:
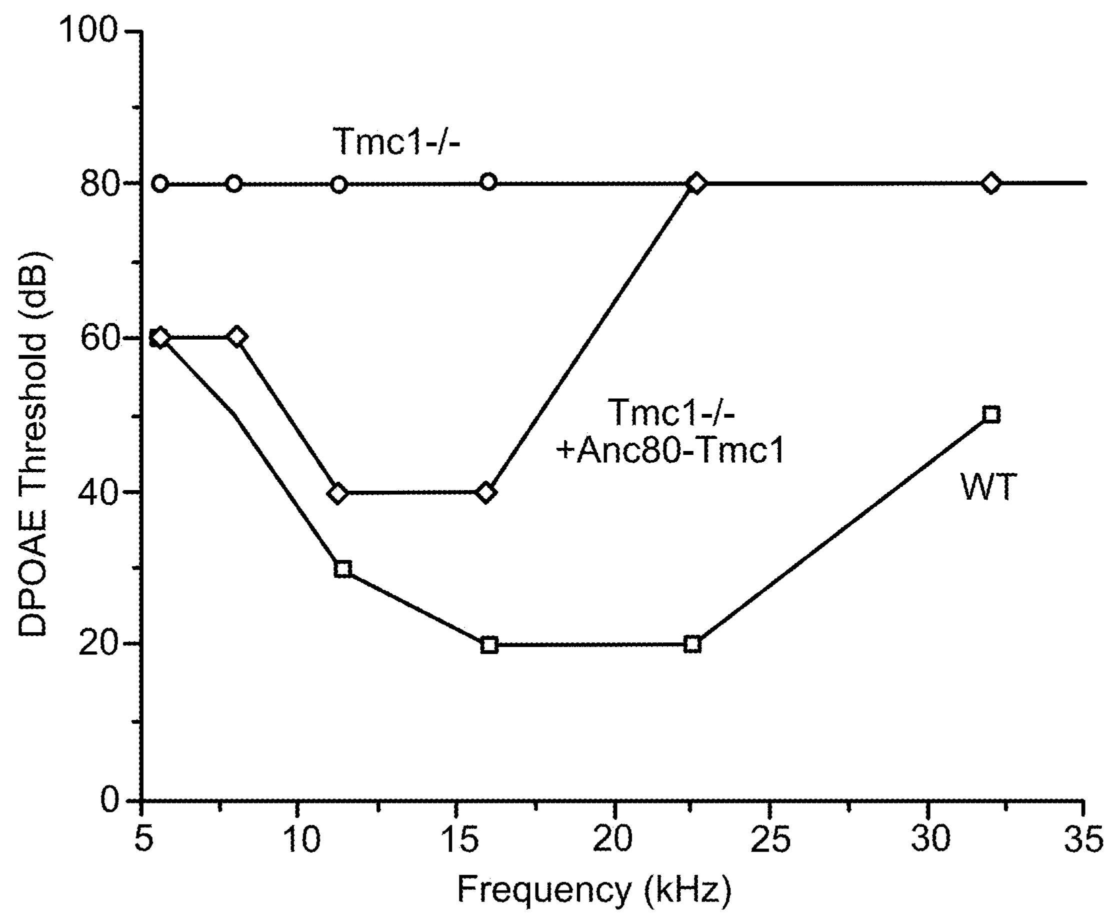

FIG. 32 is a graph showing the Distortion Product Otoacoustic Emissions (DPOAE) thresholds as a function of stimulus frequency for wild type, Tmc1−/− mice, and Tmc1−/− mice injected with Anc80 Tmc1.

DETAILED DESCRIPTION

Since the sensory cells of the adult mammalian cochlea lack the capacity for self-repair, current therapeutic strategies (depending on the level and exact position of impairment) rely on amplification (hearing aids), better transmission of sound (middle ear prostheses/active implants), or direct neuronal stimulation (cochlear implants) to compensate for permanent damage to primary sensory hair cells or spiral ganglion neurons which form the auditory nerve and relay acoustic information to the brain. While these approaches have been transformative, they remain far from optimal in restoring complex human hearing function important for modern life. Specifically, major problems still include limited frequency sensitivity, unnatural sound perception, and limited speech discrimination in noisy environments.

Therapeutic gene transfer to the cochlea has been considered to further improve upon the current standard of care ranging from age-related and environmentally induced hearing loss to genetic forms of deafness. More than 300 genetic loci have been linked to hereditary hearing loss with over 70 causative genes described (Parker & Bitner-Glindzicz, 2015, *Arch. Dis. Childhood,* 100:271-8). Therapeutic success in these approaches relies significantly on the safe and efficient delivery of exogenous gene constructs to the relevant therapeutic cell targets in the organ of Corti (OC) in the cochlea.

The OC includes two classes of sensory hair cells: IHCs, which convert mechanical information carried by sound into electrical signals transmitted to neuronal structures and OHCs which serve to amplify and tune the cochlear response, a process required for complex hearing function. Other potential targets in the inner ear include spiral ganglion neurons, columnar cells of the spiral limbus, which are important for the maintenance of the adjacent tectorial membrane or supporting cells, which have protective functions and can be triggered to trans-differentiate into hair cells up to an early neonatal stage.

Injection to the cochlear duct, which is filled with high potassium endolymph fluid, could provide direct access to hair cells. However, alterations to this delicate fluid environment may disrupt the endocochlear potential, heightening the risk for injection-related toxicity. The perilymph-filled spaces surrounding the cochlear duct, scala tympani and scala vestibuli, can be accessed from the middle ear, either through the oval or round window membrane (RWM). The RWM, which is the only non-bony opening into the inner ear, is relatively easily accessible in many animal models and administration of viral vector using this route is well tolerated. In humans, cochlear implant placement routinely relies on surgical electrode insertion through the RWM.

Previous studies evaluating AAV serotypes in organotypic cochlear explant and in vivo inner ear injection have resulted in only partial rescue of hearing in mouse models of inherited deafness. Unexpectedly, an adeno-associated virus (AAV) containing an ancestral AAV capsid protein transduces OHCs with high efficiency. This finding overcomes the low transduction rates that have limited successful development of cochlear gene therapy using conventional AAV serotypes. An AAV containing an ancestral AAV capsid protein as described herein provides a valuable platform for inner ear gene delivery to IHCs and OHCs, as well as an array of other inner ear cell types that are compromised by genetic hearing and balance disorders. In addition to providing high transduction rates, an AAV containing an ancestral AAV capsid protein as described herein was shown to have an analogous safety profile in mouse and nonhuman primate upon systemic injection, and is antigenically distinct from circulating AAVs, providing a potential benefit in terms of pre-existing immunity that limits the efficacy of conventional AAV vectors.

Compositions and methods are described herein, however, that allow for highly efficient delivery of nucleic acids to cells, particularly cells within the inner ear, e.g., in the cochlea (or cells of the cochlea or cochlear cells). As used herein, inner ear cells refer to, without limitation, inner hair cells (IHCs), outer hair cells (OHCs), spiral ganglion neurons, vestibular hair cells, vestibular ganglion neurons, supporting cells and cells in the stria vascularis. Supporting cells refer to cells in the ear that are not excitable, e.g., cells that are not hair cells or neurons. An example of a supporting cell is a Schwann cell.

Delivery of one or more of the nucleic acids described herein to inner ear cells can be used to treat any number of inherited or acquired hearing disorders, which are typically defined by partial hearing loss or complete deafness. The methods described herein can be used to treat a hearing disorder such as, without limitation, recessive deafnesses, dominant deafnesses, Usher syndrome, and other syndromic deafnesses as well as hearing loss due to trauma or aging.

Methods of Making Viruses Carrying Specific Transgenes

As described herein, an adeno-associated virus (AAV) containing an ancestral AAV capsid protein are particularly efficient at delivering nucleic acids (e.g., transgenes) to inner ear cells, and a particularly effective class of ancestral AAV capsid proteins is designated by an ancestral scaffold capsid protein designated Anc80, which is shown in SEQ ID NO:1. One particular ancestral capsid protein that falls within the class of Anc80 ancestral capsid proteins is Anc80-0065 (SEQ ID NO:2), however, WO 2015/054653 describes a number of additional ancestral capsid proteins that fall within the class of Anc80 ancestral capsid proteins.

The viruses described herein that contain an Anc80 capsid protein can be used to deliver a variety of nucleic acids to inner ear cells. A nucleic acid sequence delivered to a cell for the purpose of expression oftentimes is referred to as a transgene. Representative transgenes that can be delivered to, and expressed in, inner ear cells include, without limitation, a transgene that encodes a neurotrophic factor (e.g., glial cell line-derived neurotrophic factor (GDNF), brain-derived neurotrophic factor (BDNF), neurotrophin-3 (NT3), or heat shock protein (HSP)-70), an immunomodulatory protein or an anti-oncogenic transcript. In addition, representative transgenes that can be delivered to, and expressed in, inner ear cells also include, without limitation, a transgene that encodes an antibody or fragment thereof, an antisense, silencing or long non-coding RNA species, or a genome editing system (e.g., a genetically-modified zinc finger nuclease, transcription activator-like effector nucleases (TALENs), or clustered regularly interspaced short palindromic repeats (CRISPRs)). Further, representative transgenes that can be delivered to, and expressed in, inner ear cells include nucleic acids designated ACTG1, ADCY1, ATOHI, ATP6V1B1, BDNF, BDP1, BSND, DATSPER2, CABP2, CD164, CDC14A, CDH23, CEACAM16, CHD7, CCDC50, CIB2, CLDN14, CLIC5, CLPP, CLRN1, COCH, COL2A1, COL4A3, COL4A4, COL4A5, COL9A1, COL9A2, COL11A1, COL11A2, CRYM, DCDC2, DFNA5, DFNB31, DFNB59, DIAPH1, EDN3, EDNRB, ELMOD3, EMOD3, EPS8, EPS8L2, ESPN, ESRRB, EYA1, EYA4, FAM65B, FOXI1, GIPC3, GJB2, GJB3, GJB6, GPR98, GRHL2, GPSM2, GRXCR1, GRXCR2, HARS2, HGF, HOMER2, HSD17B4, ILDR1, KARS, KCNE1, KCNJ10, KCNQ1, KCNQ4, KITLG, LARS2, LHFPL5, LOXHD1, LRTOMT, MARVELD2, MCM2, MET, MIR183, MIRN96, MITF, MSRB3, MT-RNR1, MT-TS1, MYH14, MYH9, MYO15A, MYO1A, MYO3A, MYO6, MYO7A, NARS2, NDP, NF2, NT3, OSBPL2, OTOA, OTOF, OTOG, OTOGL, P2RX2, PAX3, PCDH15, PDZD7, PJVK, PNPT1, POLR1D, POLR1C, POU3F4, POU4F3, PRPS1, PTPRQ, RDX, S1PR2, SANS, SEMA3E, SERPINB6, SLC17A8, SLC22A4, SLC26A4, SLC26A5, SIX1, SIX5, SMAC/DIABLO, SNAI2, SOX10, STRC, SYNE4, TBC1D24, TCOF1, TECTA, TIMM8A, TJP2, TNC, TMC1, TMC2, TMIE, TMEM132E, TMPRSS3, TRPN, TRIOBP, TSPEAR, USH1C, USH1G, USH2A, USH2D, VLGR1,WFS1, WHRN, and XIAP. Descriptions and definitions of the nomenclature used herein can be found at hereditaryhearingloss.org/ on the World Wide Web.

Expression of a transgene may be directed by the transgene's natural promoter (i.e., the promoter found naturally with the transgenic coding sequence) or expression of a transgene may be directed by a heterologous promoter. For example, any of the transgenes described herein can be used with its natural promoter. Alternatively, any of the transgenes described herein can be used with a heterologous promoter. As used herein, a heterologous promoter refers to a promoter that does not naturally direct expression of that sequence (i.e., is not found with that sequence in nature). Representative heterologous promoters that can be used to direct expression of any of the transgenes indicated herein include, for example, a cytomegalovirus (CMV) promoter, a chicken beta actin (CBA) promoter, a synthetic CASI promoter, a phosphoglycerate kinase (PGK) promoter, and a elongation factor (EF)-1 promoter, an alpha9 nicotinic receptor promoter, a prestin promoter, a growth factor independent (GFI1) promoter, and a vesicular glutamate transporter 3 (VGLUT3) promoter. In addition, a promoter that naturally directs expression of one of the above-referenced transgenes (e.g., a KCNQ4 promoter, a Myo7a promoter, a Myo6 promoter or an ATOH1 promoter) can be used as a heterologous promoter to direct expression of a transgene.

Methods of making a transgene for packaging into a virus that contains an Anc80 capsid protein are known in the art, and utilize conventional molecular biology and recombinant nucleic acid techniques. In one embodiment, a construct that includes a nucleic acid sequence encoding an Anc80 capsid protein and a construct carrying the transgene flanked by suitable Inverted Terminal Repeats (ITRs) are provided, which allows for the transgene to be packaged within the Anc80 capsid protein.

The transgene can be packaged into an AAV containing an Anc80 capsid protein using, for example, a packaging host cell. The components of a virus particle (e.g., rep sequences, cap sequences, inverted terminal repeat (ITR) sequences) can be introduced, transiently or stably, into a packaging host cell using one or more constructs as described herein. The viruses described herein contain at least an Anc80 capsid protein; the other components of a virus particle (e.g., rep sequences, ITR sequences) can be based on an ancestral sequence or a contemporary sequence. In some instances, for example, the entire virus particle can be based on ancestral sequences. Such viruses can be purified using routine methods.

It would be appreciated that one or more than one transgene can be delivered to the inner ear. It also would be appreciated that more than one transgene can be delivered to the inner ear using a single AAV vector that includes an Anc80 capsid protein or using multiple AAV vectors that includes an Anc80 capsid protein.

In general, as used herein, "nucleic acids," can include DNA and RNA, and also can include nucleic acids that contain one or more nucleotide analogs or backbone modifications. Nucleic acids can be single-stranded or double-stranded, which usually depends upon its intended use. Nucleic acids that can be used in the methods described herein can be identical to a known nucleic acid sequence, or nucleic acids that can be used in the methods described herein can differ in sequence from such known sequences. Simply by way of example, nucleic acids (or the encoded polypeptides) can have at least 75% sequence identity (e.g., at least 80%, 81%, 82%, 83%, 84%, 85%, 86%, 87%, 88%, 89%, 90%, 91%, 92%, 93%, 94%, 95%, 96%, 97%, 98%, or 99% sequence identity) to a known sequence.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region.

The alignment of two or more sequences to determine percent sequence identity is performed using the computer program ClustalW and default parameters, which allows alignments of nucleic acid or polypeptide sequences to be carried out across their entire length (global alignment). Chenna et al., 2003, Nucleic Acids Res., 31(13):3497-500. ClustalW calculates the best match between a query and one or more subject sequences, and aligns them so that identities, similarities and differences are determined. Gaps of one or more residues can be inserted into a query sequence, a subject sequence, or both, to maximize sequence alignments. For pairwise alignment of nucleic acid sequences, the default parameters are used (i.e., word size: 2; window size: 4; scoring method: percentage; number of top diagonals: 4;

and gap penalty: 5); for an alignment of multiple nucleic acid sequences, the following parameters are used: gap opening penalty: 10.0; gap extension penalty: 5.0; and weight transitions: yes. For pairwise alignment of polypeptide sequences, the following parameters are used: word size: 1; window size: 5; scoring method: percentage; number of top diagonals: 5; and gap penalty: 3. For multiple alignment of polypeptide sequences, the following parameters are used: weight matrix: BLOSUM (blocks substitution matrix); gap opening penalty: 10.0; gap extension penalty: 0.05; hydrophilic gaps: on; hydrophilic residues: Gly, Pro, Ser, Asn, Asp, Gln, Glu, Arg, and Lys; and residue-specific gap penalties: on. ClustalW can be run, for example, at the Baylor College of Medicine Search Launcher website or at the European Bioinformatics Institute website on the World Wide Web.

Changes can be introduced into a nucleic acid sequence, which can lead to changes in the amino acid sequence of the encoded polypeptide if the nucleic acid sequence is a coding sequence. For example, changes can be introduced into nucleic acid coding sequences using mutagenesis (e.g., site-directed mutagenesis, PCR-mediated mutagenesis) or by chemically synthesizing a nucleic acid molecule having such changes. Such nucleic acid changes can lead to conservative and/or non-conservative amino acid substitutions at one or more amino acid residues. A "conservative amino acid substitution" is one in which one amino acid residue is replaced with a different amino acid residue having a similar side chain (see, for example, Dayhoff et al. (1978, in Atlas of Protein Sequence and Structure, 5(Suppl. 3):345-352), which provides frequency tables for amino acid substitutions), and a non-conservative substitution is one in which an amino acid residue is replaced with an amino acid residue that does not have a similar side chain.

A nucleic acid can be contained within a construct, which also can be referred to as a vector or a plasmid. Constructs are commercially available or can be produced by recombinant techniques routine in the art. A construct containing a nucleic acid can have expression elements that direct and/or regulate expression of such a nucleic acid, and also can include sequences such as those for maintaining the construct (e.g., origin of replication, a selectable marker). Expression elements are known in the art and include, for example, promoters, introns, enhancer sequences, response elements, or inducible elements.

Methods of Delivering Nucleic Acids to Inner Ear Cells

Methods of delivering nucleic acids to cells generally are known in the art, and methods of delivering viruses (which also can be referred to as viral particles) containing a transgene to inner ear cells in vivo are described herein. As described herein, about $10^8$ to about $10^{12}$ viral particles can be administered to a subject, and the virus can be suspended within a suitable volume (e.g., 10 μL, 50 μL, 100 μL, 500 μL, or 1000 μL) of, for example, artificial perilymph solution.

A virus containing a transgene as described herein can be delivered to inner ear cells (e.g., cells in the cochlea) using any number of mechanisms. For example, a therapeutically effective amount of a composition including virus particles containing one or more different types of transgenes as described herein can be injected through the round window or the oval window, typically in a relatively simple (e.g., outpatient) procedure. In some embodiments, a composition comprising a therapeutically effective number of virus particles containing a transgene, or containing one or more sets of different virus particles, wherein each particle in a set can contain the same type of transgene, but wherein each set of particles contains a different type of transgene than in the other sets, as described herein can be delivered to the appropriate position within the ear during surgery (e.g., a cochleostomy or a canalostomy).

In addition, delivery vehicles (e.g., polymers) are available that facilitate the transfer of agents across the tympanic membrane and/or through the round window, and any such delivery vehicles can be used to deliver the viruses described herein. See, for example, Arnold et al., 2005, *Audiol. Neurootol.,* 10:53-63.

The compositions and methods described herein enable the highly efficient delivery of nucleic acids to inner ear cells, e.g., cochlear cells. For example, the compositions and methods described herein enable the delivery to, and expression of, a transgene in at least 80% (e.g., at least 85, 90, 91, 92, 93, 94, 95, 96, 97, 98, or 99%) of inner hair cells or delivery to, and expression in, at least 80% (e.g., at least 85, 90, 91, 92, 93, 94, 95, 96, 97, 98, or 99) of outer hair cells.

As demonstrated herein, expression of a transgene delivered using an AAV containing an Anc80 capsid protein can result in regeneration of inner hair cells (IHCs), outer hair cells (OHCs), spiral ganglion neurons, stria vascularis, vestibular hair cells, and/or vestibular ganglion neurons (e.g. Atoh1, NF2) such that hearing or vestibular function is restored for an extended period of time (e.g., months, years, decades, a life time).

As discussed in WO 2015/054653, an AAV containing an Anc80 capsid protein can be characterized by its seroprevelance and/or the extent it is neutralized relative to conventional AAVs (i.e., an AAV not containing an Anc80 capsid protein). Seroprevalence is understood in the art to refer to the proportion of subjects in a population that is seropositive (i.e., has been exposed to a particular pathogen or immunogen), and is calculated as the number of subjects in a population who produce an antibody against a particular pathogen or immunogen divided by the total number of individuals in the population examined. Determining the seroprevalence of a virus is routinely performed in the art and typically includes using an immunoassay to determine the prevalence of one or more antibodies in samples (e.g., blood samples) from a particular population of individuals. In addition, several methods to determine the extent of neutralizing antibodies in a serum sample are available. For example, a neutralizing antibody assay measures the titer at which an experimental sample contains an antibody concentration that neutralizes infection by 50% or more as compared to a control sample without antibody. See, also, Fisher et al. (1997, *Nature Med.,* 3:306-12) and Manning et al. (1998, *Human Gene Ther.,* 9:477-85). Representative conventional AAVs include, without limitation, AAV8 (or a virus comprising an AAV8 capsid protein) and/or AAV2 (or a virus comprising an AAV2 capsid protein).

Usher Syndrome

Human Usher syndrome (USH) is a rare genetic condition responsible for combined deafness and blindness. Inherited as an autosomal recessive trait, it affects 16,000 to 20,000 people in the United States and is responsible for 3 to 6% of early childhood deafness. Usher syndrome is classified under three clinical subtypes (USH-1, -2 and -3) according to the severity of the symptoms. USH1 is the most severe form. Patients who are affected by USH1 suffer congenital bilateral profound sensorineural hearing loss, vestibular areflexia and pre-pubertal retinitis pigmentosa (a progressive, bilateral, symmetric degeneration of rod and cone function of the retina). Unless fitted with a cochlear implant, individuals do not typically develop the ability to generate speech. While no biological treatments currently exist for Usher patients, early reintroduction of the wild-type form of the defective gene may allow for reversal of the disease.

Six Usher genes are associated with USH1: MYO7A (myosin 7a), USH1C (harmonin), CDH23 (cadherin 23), PCDH15 (protocadherin 15), SANS (sans) and CIB2 (calcium and integrin binding protein 2). These genes encode proteins that are involved in hair bundle morphogenesis in the inner ear and are part of an interactome (see, for example, Mathur & Yang, 2015, *Biochim. Biophys. Acta,* 1852:406-20). Harmonin resides at the center of the USH1 interactome where it binds to other Usher 1 proteins. Because of its PDZ (PSD-59 95/Dlg/ZO-1) interaction domains, harmonin has been proposed to function as a scaffolding protein. In vitro binding studies have shown that all other known USH1 proteins bind to PDZ domains of harmonin as do two of the USH2 proteins, usherin, and VLGR1. The USH1C gene consists of 28 exons, which code for 10 alternative splice forms of harmonin, grouped into three different subclasses (a, b and c) depending on the domain composition of the protein. The three isoforms differ in the number of PDZ protein-protein interaction domains, coiled-coiled (CC) domains, and proline-serine-threonine (PST) rich domains.

USH1 proteins are localized to the apex of hair cells in mechanosenosory hair bundles, which are composed of hundreds of stereocilia interconnected by numerous extracellular links. Cadherin 23 and Protocadherin 15, products of Usher genes (USH1D and USH1E, respectively) form tip-links located at the distal end of the stereocilia. Harmonin-b binds to CDH23, PCDH15, F-actin and itself. It is found at the tips of the stereocilia near the tip-link insertion point in hair cells where it is thought to play a functional role in transduction and adaptation in hair cells. Harmonin-b is expressed during early postnatal stages, but its expression diminishes around postnatal day 30 (P30) in both the cochlea and vestibule. Harmonin-a also binds to cadherin 23 and is found in the stereocilia. Recent reports reveal an additional role for harmonin-a at the synapse where it associates with Cav1.3 Ca2+ channels to limit channel availability through an ubiquitin-dependent pathway.

Several mouse models for Usher syndrome have been identified or engineered over the past decade, seven of which affect harmonin. Of these, only one model, the Ush1c c.216G>A model, reproduces both auditory and retinal deficits that characterize human Usher Syndrome. Ush1c c.216G>A is a knock-in mouse model that affects expression of all conventional harmonin isoforms due to a point mutation similar to the one found in a cohort of French-Acadian USH1C patients. The mutation introduces a cryptic splice site at the end of exon three of the Ush1c gene. Use of this cryptic splice site produces a frame-shifted transcript with a 35 bp deletion and results in translation of a severely truncated protein lacking PDZ, PST and CC domains. Homozygous c.216AA knock-in mice suffer from severe hearing loss at 1 month of age while heterozygous c.216GA mice do not present any abnormal phenotype. Cochlear histology in c.216AA mice shows disorganized hair bundles, abnormal cell rows and loss of both inner and outer hair cells in middle and basal turns at P30.

In particular, one can treat a patient diagnosed with Usher Syndrome-related deafness, e.g., USH1C-related deafness, using the ancestral AAV capsid proteins described herein combined with a harmonin transgene to successfully transduce hair cells and drive expression and correct localization of harmonin splice forms, thereby re-introducing wild-type harmonin. Furthermore, it is demonstrated herein that early postnatal round window membrane injection of an AAV containing an ancestral AAV capsid protein as described herein successfully restored auditory and vestibular function in homozygous c.216AA mice. Recovery of auditory function in injected mice is associated with recovery of mRNA expression encoding for wild-type harmonin as well as preservation of hair bundle morphology and mechanotransduction.

TMC1/TMC2

Over 40 distinct mutations have been identified in TMC1 that cause deafness. These are subdivided into 35 recessive mutations and 5 dominant mutations. Most of the recessive mutations cause profound, congenital hearing loss (e.g., DFNB7/11) though a few cause later onset, moderate to severe hearing loss. All of the dominant mutations cause progressive hearing loss (e.g., DFNA36), with onset in the mid-teen years. In particular, an AAV vector that includes an Anc80 capsid protein as described herein can be used to deliver a non-mutant (e.g., wild type) TMC1 sequence or TMC2 sequence, thereby preventing hearing loss (e.g., further hearing loss) and/or restoring hearing function.

Conventional molecular biology, microbiology, biochemical, and recombinant DNA techniques within the skill of the art can be used in accordance with the present disclosure. Such techniques are explained fully in the literature and are exemplified in the certain of the Examples below. The invention will be further described in the following examples, which do not limit the scope of the methods and compositions of matter described in the claims.

EXAMPLES

Part 1: Highly Efficient Cochlear Gene Transfer

Example 1—an Adeno-Associated Virus (AAV) Containing an Ancestral AAV Capsid Protein Results in Safe and Efficient Cochlear Gene Transfer The following methods and materials were used in Example 1.

Viral Vectors

AAV2/1, 2/2, 2/6, 2/8, 2/9 and AAV2/Anc80L65 with a CMV-driven eGFP transgene and the Woodchuck hepatitis virus Post-transcriptional Regulatory Element (WPRE) cassette were prepared at Gene Transfer Vector Core (vector.meei.harvard.edu) at Massachusetts Eye and Ear as previously described (Zinn et al., 2015, Cell Reports, 12:1056-68). AAV2/Anc80L65 plasmid reagents are available through addgene.com.

In Vitro Explant Cultures

A total of 156 cochlear explant cultures from mouse pups of both strains were prepared on postnatal day 4 in order to assess as described in an earlier publication (Dilwali et al., 2015, Scientific Reports, 5:18599). In brief, murine temporal bones were harvested after decapitation and the cochlea was dissected to culture as organotypic explants connected to the spiral ganglion neuron region. Two specimens were obtained per cochlea, one ("apical") consisting of the lower apical and one ("basal") of the upper basal turn. For each serotype, a minimum of 4 (CBA/CaJ, 48h), 2 (CBA/CaJ, 48h+5 d), 3 (C57BL/6, 48h), 2 (C57BL/6, 48h+5 d) basal and apical specimen were inoculated. Specimens were excluded if cochlear morphology was not retained during the culture. Sample numbers were chosen to inform on the variability of transduction and to provide a basis for selection for further in vivo evaluation. Explants were incubated with culture medium (98% Dulbecco's Modified Eagle Medium (DMEM), 1% ampicillin, and 1% N2 supplement during the first 12 hours, plus 1% fetal bovine serum (FBS)) and $10^{10}$ GC of AAV for 48 h in 50 μl. For the 48h+5 d condition, the medium with AAV was replaced with fresh media without AAV for an additional 5 days. Human vestibular epithelia from utricles obtained from four consented, adult patients undergoing vestibular schwannoma tumor resection were cultured as previously described (Kesser et al., 2007, Gene Ther., 14:1121-1131), exposed to $10^{10}$ GC AAV for 24 hours and maintained in culture for 10 days after which the tissue was fixed and stained with phalloidin and imaged. Studies were approved by the Surrey Borders NRES Committee London (Health Research Authority) under reference number 11/LO/0475.

Animal Models and General Methods

Wild-type C57BL/6J and CBA/CaJ mice were obtained from the Jackson Laboratory (Bar Harbor, ME) and animals of either sex were used for experimentation in an estimated 50/50 ratio. Group sizes per experiment for the in vitro and in vivo transduction assays and subsequent endpoints were determined by access to specimen and technical feasibility. Reported observations on Anc80 transduction were qualitatively validated in subsequent experiments with various vector lots (except for the human vestibular tissue transduction due to the unique and limited nature of access to specimen). No statistical analysis between serotype transduction efficiencies was performed due to the limited access to specimen and qualitative nature of the reported findings.

CSF and Blood Sampling

Cerebrospinal fluid (CSF) sampling from the cisterna magna (Lui & Duff, 2008, J. Visualized Exp., 21:e960) and intracardiac blood collection with thoracotomy were performed in a terminal procedure. Through the microcapillary tube, the maximum amount (up to 5 μL) of clear CSF per animal was collected in a volume of 60 μL PBS, leading to slightly different starting dilutions that subsequently were standardized with additional control PBS prior to the start of the experiment. After obtaining the blood sample in a 1.1 mL Z-Gel micro tube (Sarstedt, Nümbrecht, Germany), it was spun down at 8,000 rpm for 8 minutes and serum was stored together with the CSF sample (in PBS) at −80° C. until further use.

Example 1A—Histological Analysis

After a follow-up period of 5 to 29 days, animals were sacrificed and cochlear whole mounts were prepared as previously reported (Sergeyenko et al., 2013, J. Neurosci., 33:13686-94). Both cochlear whole-mounts and explants were stained with antibodies against myosin 7A (Myo7A, #25-6790 Proteus Biosciences, Ramona, CA, 1:400) and beta-tubulin (TuJ1, #MMS-435P Biolegend, San Diego, CA, 1:200), together with corresponding secondary antibodies (Alexa Fluor 555 anti-mouse and Alexa Fluor 647 anti-rabbit, #A-21422 and #A-21245 Thermo Fisher Scientific, Waltham, MA, 1:1000) (Dilwali et al., 2015, Scientific Reports, 5:18599). Mounting of the specimens was followed by confocal microscopy. Every image of a given experimental series was obtained with the same settings, with laser intensity being chosen based on the specimen with the strongest eGFP signal to prevent fluorescence saturation. Z-stacks for overview images and zoomed-in pictures for the organ of Corti and spiral ganglion neuron (SGN) areas were obtained. 3D reconstruction with AMIRA was used to determine SGN transfection more accurately.

Figure 1:
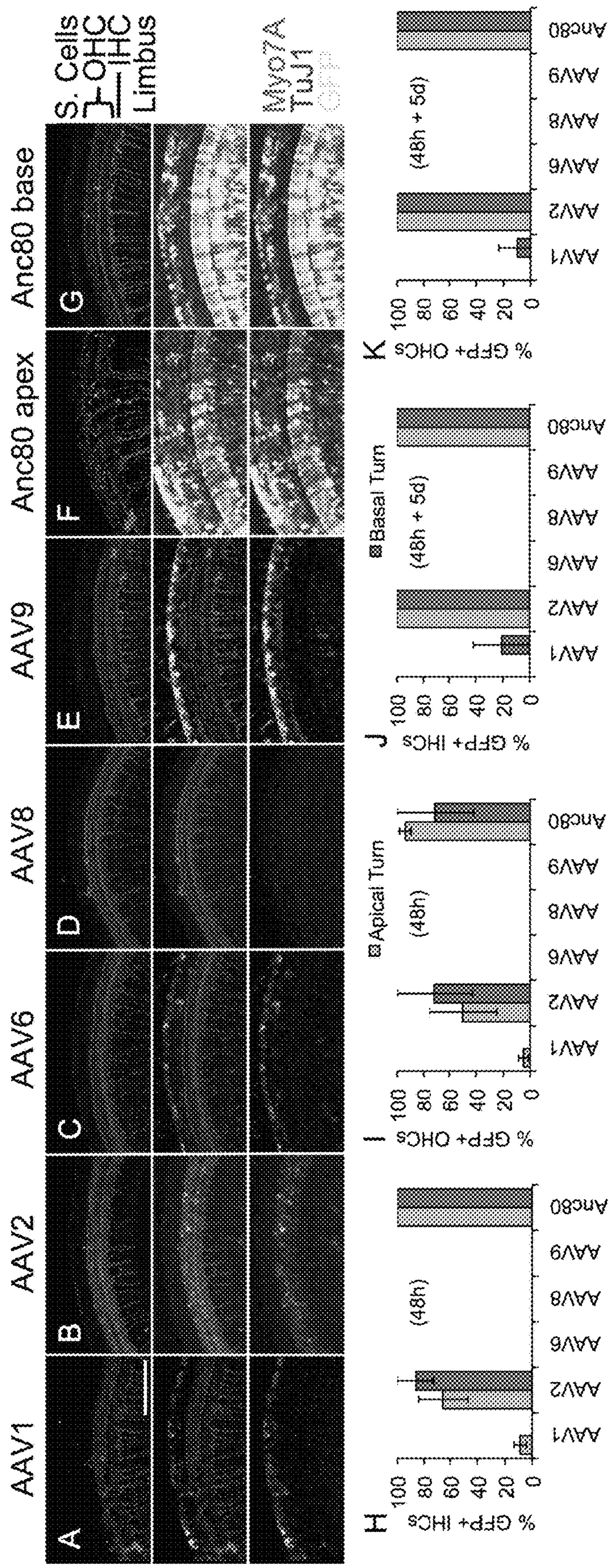
FIGS. 1A-1K are images showing representative confocal projections of an in vitro comparison of several AAV serotypes for eGFP transgene expression in cochlear explants of C57BL/6 mice.
Figure 4:
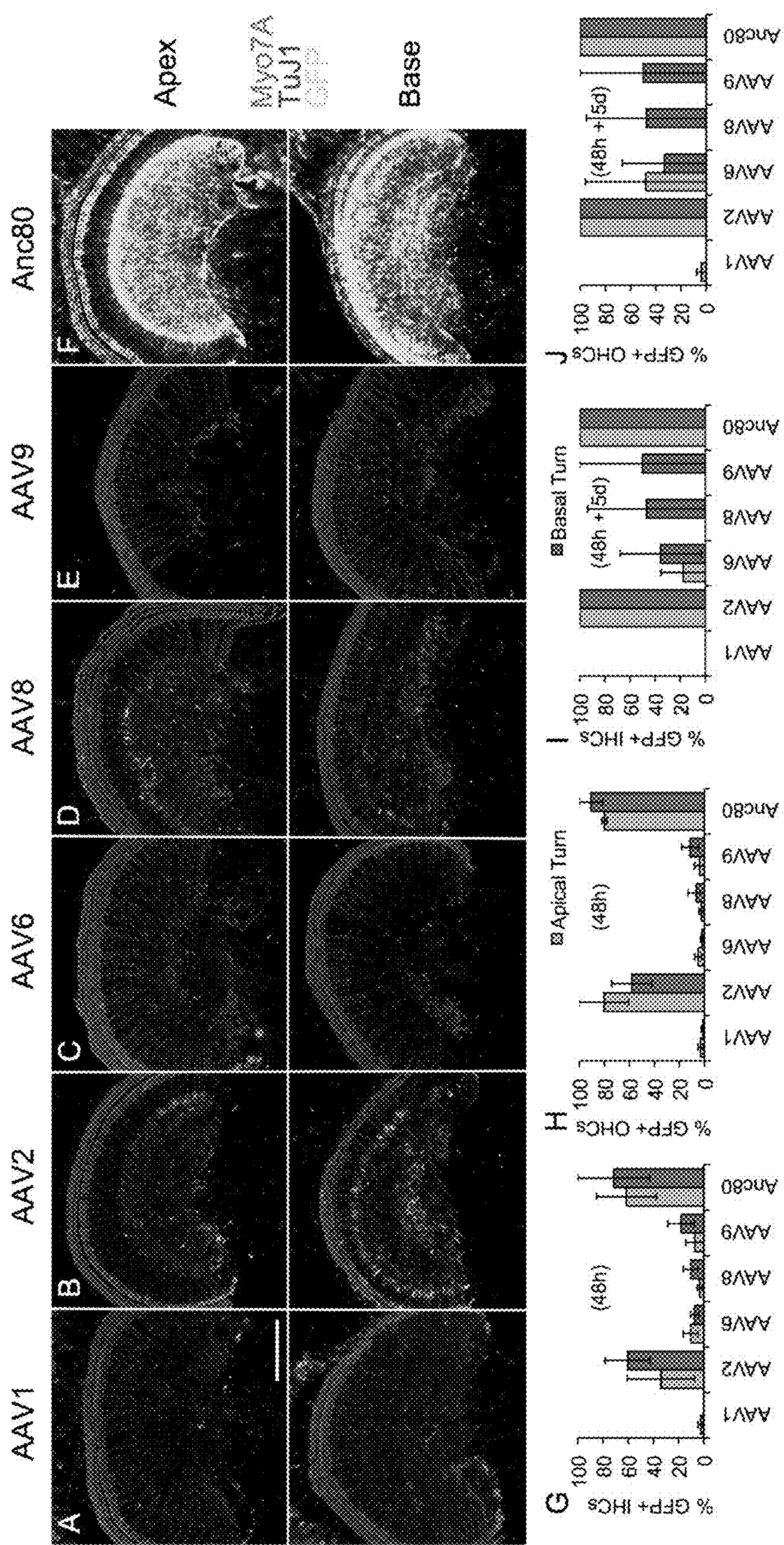
FIGS. 4A-4J are representative images of an in vitro comparison of several AAV serotypes regarding eGFP expression in cochlear explants of CBA/CaJ mice.

The results in FIG. 1 and FIG. 4 illustrate the tropism of the 5 serotypes as monitored by expression of the AAV encoding eGFP in C57BL/6 and CBA/CaJ respectively. Notably, eGFP expression was qualitatively brighter in cochlear cultures exposed to Anc80, with expression apparent in many cochlear cell types.

Example 1B—Quantification of eGFP-Expression

For in vitro data, the percentage of eGFP-positive inner (IHCs) and outer hair cells (OHCs) was manually quantified along the cochlea, by dividing the number of eGFP positive cells by the total number of outer or inner hair cells per one or two 100 μm sections per base and apex sample for each specimen. All visible SGNs in a cochlear explant were evaluated regarding their eGFP expression. The areas of the spiral limbus and supporting cells were assessed with a qualitative approach (as explained above, adjusted for each experimental series) by means of a scale from 0 (no expression) to 3 (strongest signal). Control samples without AAV were used to exclude autofluorescence. The data demonstrated that Anc80 targeted IHCs and OHCs at efficiencies between 60 and 100% in apex and base in both mouse strains tested. Anc80 demonstrated consistently and qualitatively brighter IHC and OHC eGFP expression as compared to AAV2 (FIG. 1 and FIG. 4).

Figure 5:
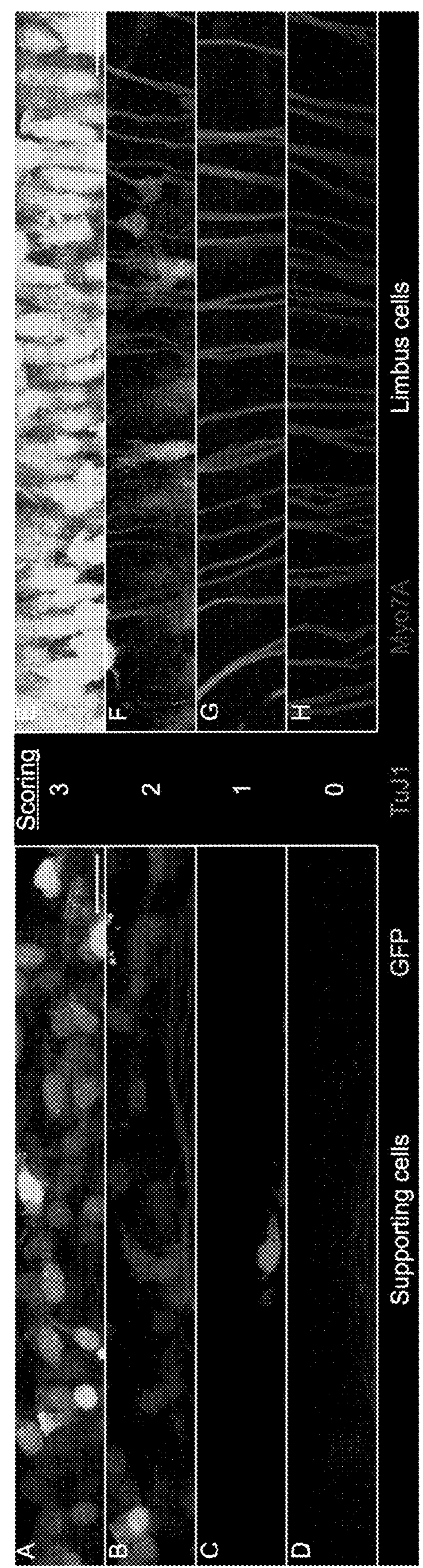
FIGS. 5A-5H are images showing a eGFP qualitative expression scoring system ranging from 0 (FIGS. 5D, 5H) (lowest expression) to 3 (FIGS. 5A, 5E) (highest level of expression) to illustrate the range of expression in terms of intensity and number of infected cells with "0" representing no noted expression (FIGS. 5D, 5H), "1" select number of cells expressing dimly (FIGS. 5C, 5G), "2" low to moderate levels of expression in significant numbers of cells per microscopic field (FIGS. 5B, 5F), and "3" high percentage of cell expressing eGFP at levels ranging from moderate to high (FIGS. 5A, 5E). Scale bar shown in FIG. 5A (for FIGS. 5A-5D) and FIG. 5E (for FIGS. 5E-5H)=20 μm.
Figure 6:
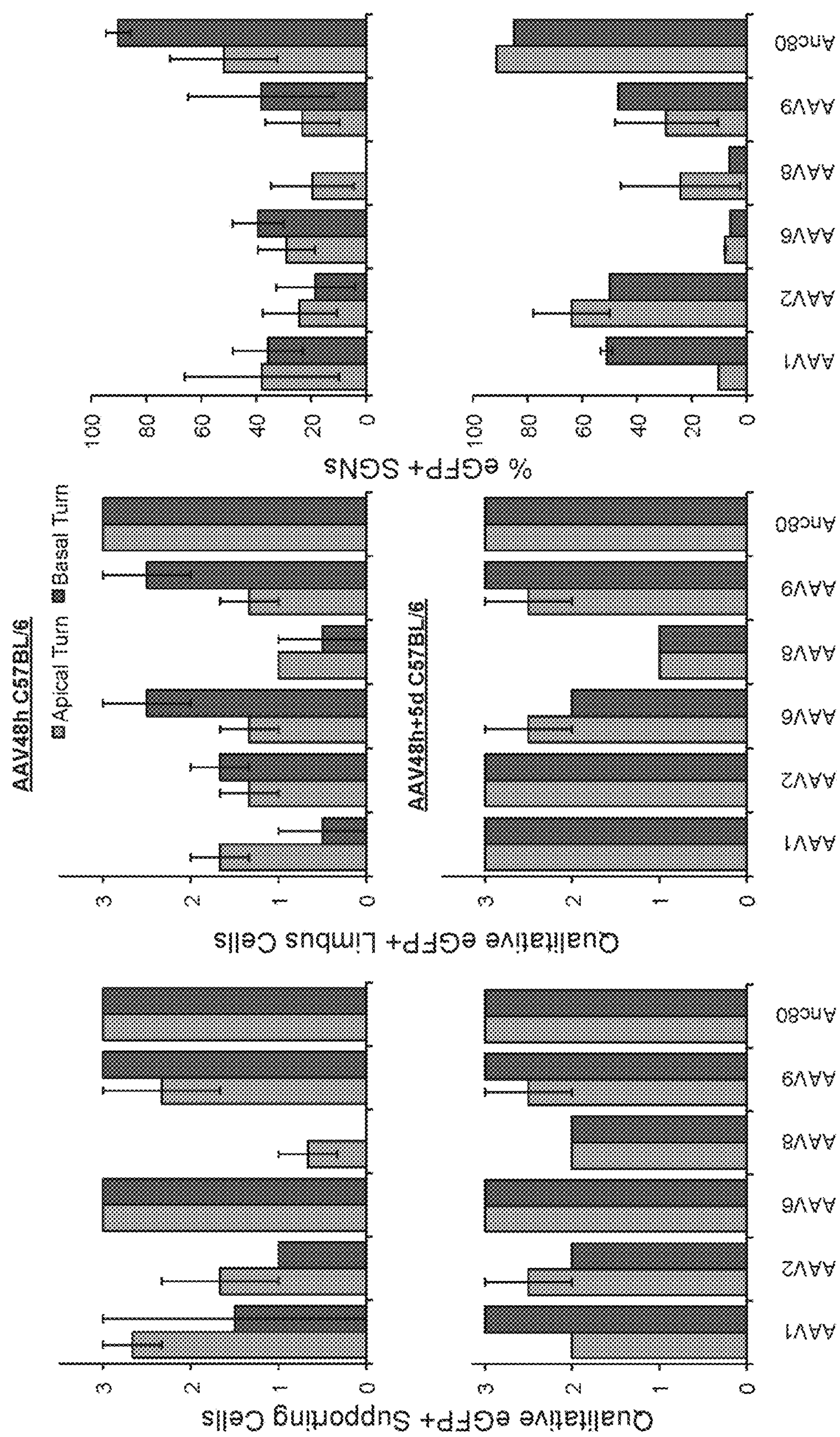
FIG. 6 are graphs showing eGFP expression in limbus, supporting cells, and spiral ganglion neurons of C57BL/6 mice using an eGFP scoring system detailed above in FIG. 5. Error bars represent SEM. SGN transduction was evaluated by eGFP-positive cell counts per microscopic field.
Figure 7:
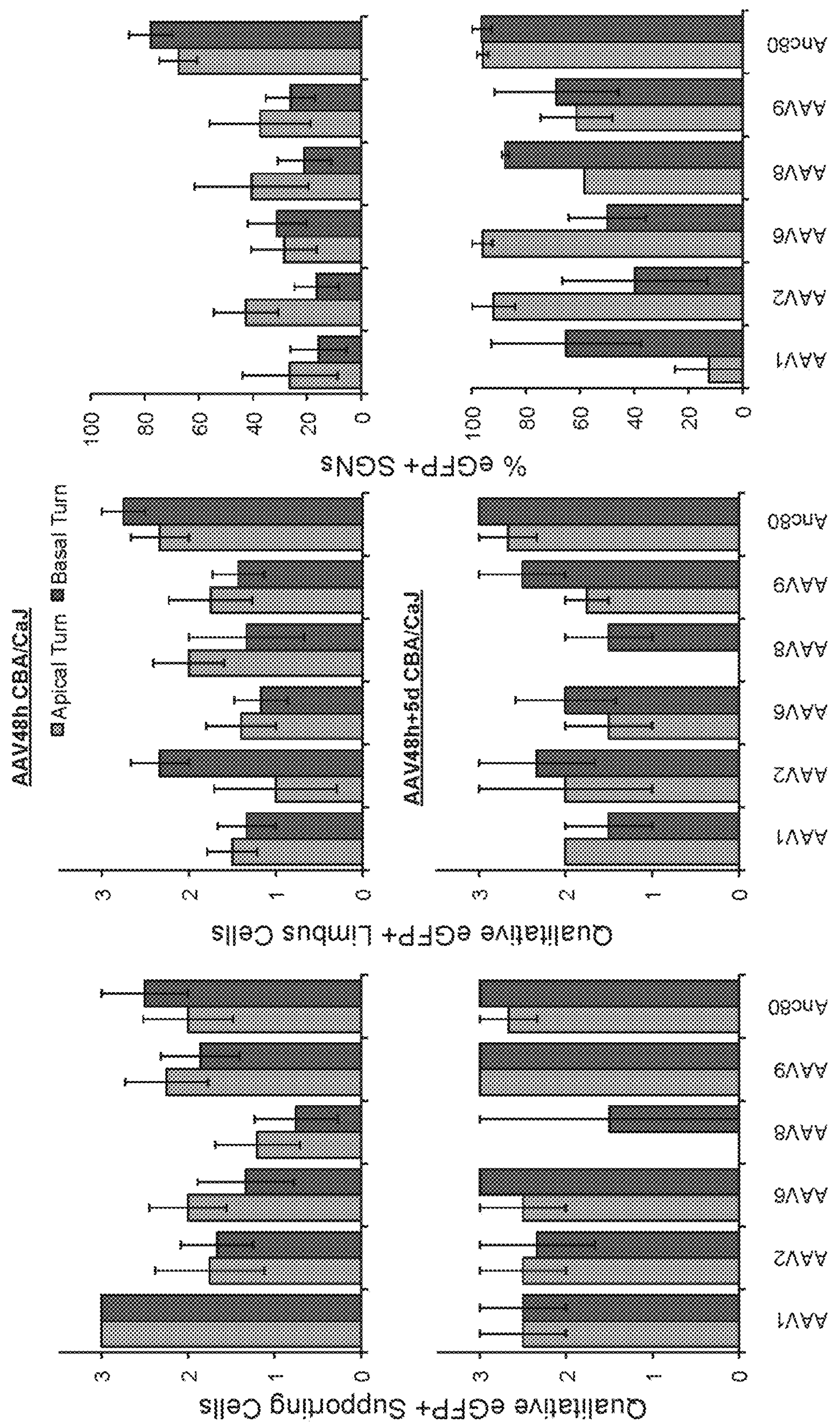
FIG. 7 are graphs showing eGFP expression in limbus, supporting cells, and spiral ganglion neurons of CBA/CaJ mice using an eGFP scoring system detailed above in FIG. 5. Error bars represent SEM. SGN transduction was evaluated by eGFP-positive cell counts per microscopic field.

To control for potential differences in the onset of expression between the different AAVs that may lead to an underestimate of expression at a 2-day (early) time point, a longer experiment was conducted. A new set of cochleae were transduced at identical conditions, yet following 48 h incubation with AAV the vector containing medium of the explant culture was removed and replaced with fresh media to maintain the culture viable for an additional 5 days (referred to as 48h+5 d). A similar pattern of expression was observed in this longer-term study for AAV2 and Anc80. Moderate increases in expression for AAV6, 8, and 9 in CBA/CaJ mice, particularly at the basal turn (FIG. 1J, 1K, and FIG. 41, 4J) were noted. Other cell types were targeted by all serotypes with limbus being more permissive than supporting cells followed by SGN (FIGS. 5, 6, and 7). Consistently, Anc80 transduction yielded higher efficiencies and stronger expression, evidenced by brighter eGFP fluorescence.

Example 1C—In Vivo Injections

Mouse pups (P0 to P2) were injected via the round window membrane (RWM) using beveled glass microinjection pipettes. Pipettes were pulled from capillary glass (WPI) on a P-2000 pipette puller (Sutter Instrument, Novato, CA) and were beveled (~20 μm tip diameter at a 28° angle) using a micropipette beveler (Sutter Instrument, Novato, CA). EMLA cream (lidocaine 2.5% and prilocaine 2.5%) was applied externally for analgesia using sterile swabs to cover the surgical site (left mastoid prominence). Body temperature was maintained on a 38° C. warming pad prior to surgery. Pups were anesthetized by rapid induction of hypothermia into ice/water for 2-3 minutes until loss of consciousness, and this state was maintained on a cooling platform for 5-10 minutes during the surgery. The surgical site was disinfected by scrubbing with Betadine and wiping with 70% Ethanol in repetition three times. A post-auricular incision was made to expose the transparent otic bulla, a micropipette was advanced manually through the bulla and overlying fascia, and the RWM was penetrated by the tip of the micropipette. Approximately 1 μL of virus was injected unilaterally within 1 min into the left ear manually in 5 (AAV1), 4 (AAV2), 2 (AAV8), 1 (AAV6), 3 (Anc80)

C57BL/6 animals. In order to control for factors related to the specific vector preparation such as quality and purity, Anc80 results were confirmed in subsequent studies with different vector lots from independent preparation which were confirmatory of our qualitative findings presented here (data not shown). Injections were performed per group in anon-blinded fashion. Occasionally, the injection needle was inserted too deep, too shallow or at the wrong angle. If there was visible damage to the middle or inner ear structures, the samples were excluded from further analysis. Success rates of injection ranged between ~50% to ~80% depending on the experience level of the injector. After the injection, the skin incision was closed using a 6-0 black monofilament suture (Surgical Specialties, Wyomissing, PA). Pups were subsequently returned to the 38° C. warming pad for 5-10 min and then put back to their mother for breeding.

Figure 2:
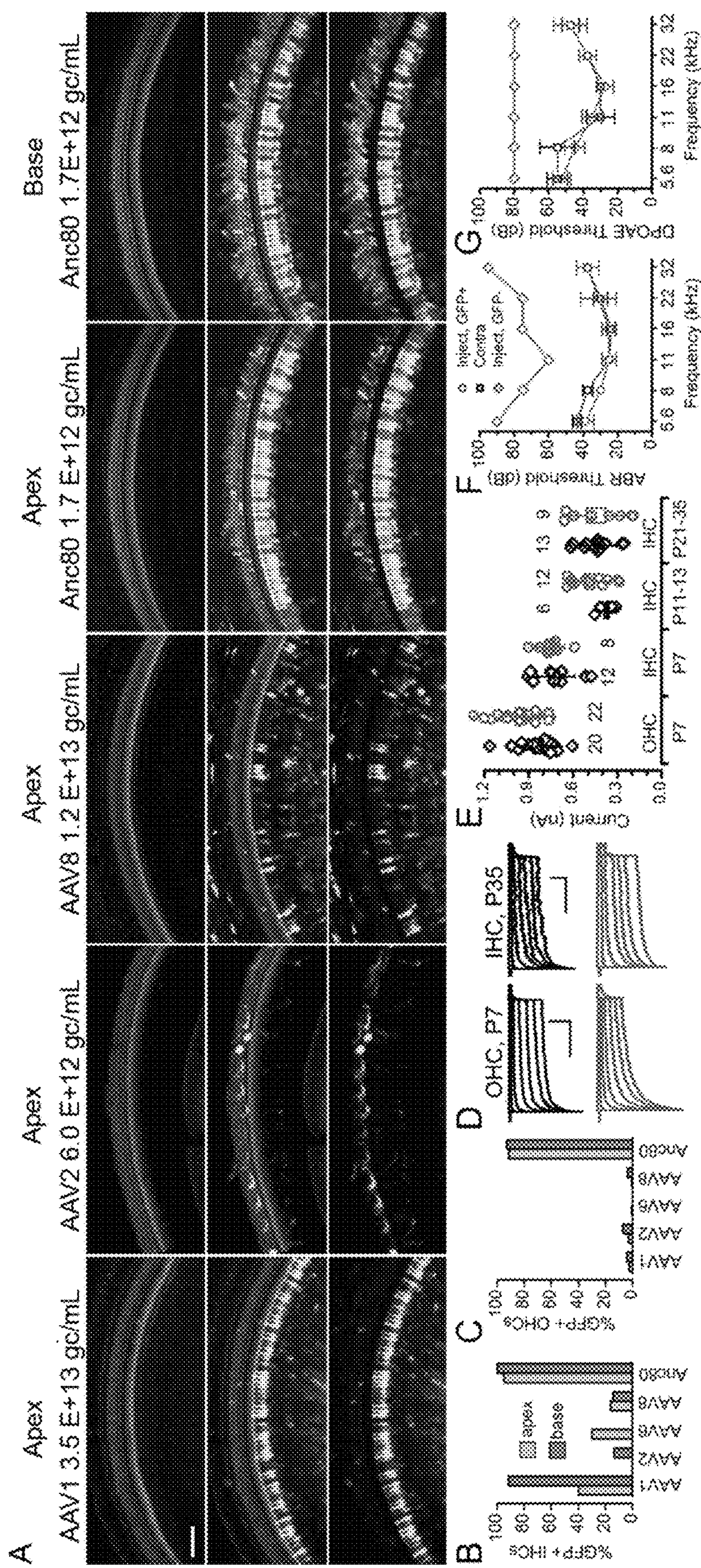
FIGS. 2A-2G are images showing in vivo cochlear transduction of the indicated AAV serotype at the titer indicated above each panel.

Consistent with prior reports, AAV1 transduced IHCs with moderate to high efficiency (FIG. 2A, 2B). These studies indicate AAV2, 6, and 8 targeted low numbers of IHCs, with only AAV8 demonstrating roughly equivalent transduction in apex and base (FIG. 2B). Also, consistent with prior reports, there was minimal OHC transduction (<5%) for all conventional AAV serotypes tested. However, Anc80 transduced nearly 100% of IHCs and ~90% of OHCs (FIG. 2A-2C) at a 20- (for AAV1) to 3-fold (for AAV2) lower dose. Transduction at equal dose of $1.36\times10^{12}$ GC for all serotypes resulted in substantial IHC and OHC transduction for Anc80, but minimal IHC targeting for AAV1, 2, and 8, and none noted in OHCs as observed by live-cell imaging by epifluorescent microscopy (FIG. 8C, 8D).

Figure 8:
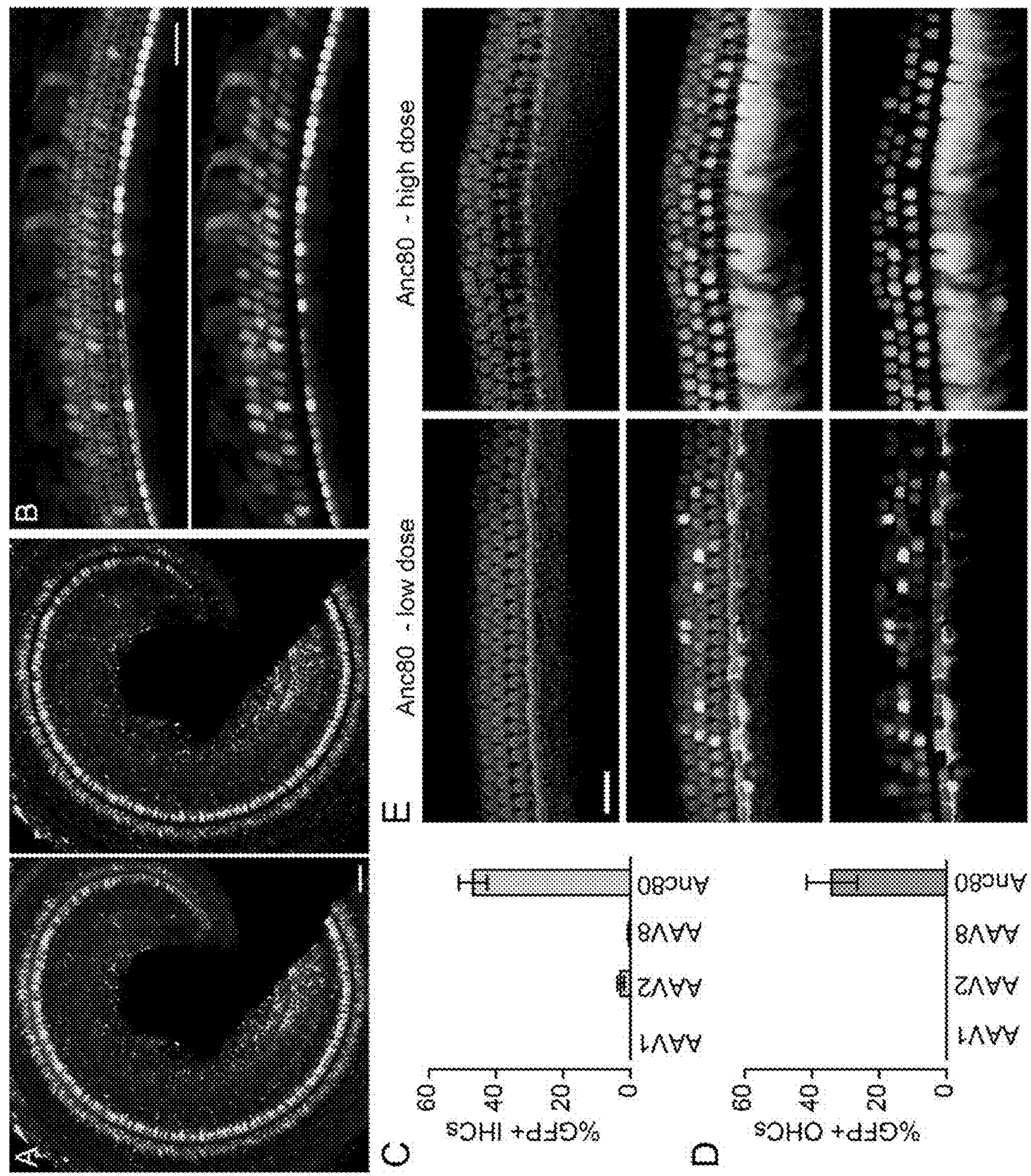
FIGS. 8A-8E are images showing extensive inner and outer hair cell transduction in murine cochleae with Anc80.

The Anc80-transduced samples were subsequently fixed, stained and imaged by confocal microscopy, revealing a dose-dependency of hair cell transduction (FIG. 8E). The unparalleled OHC targeting (FIG. 2C, FIG. 8) illustrates qualitatively distinct transduction biology of Anc80 compared to other AAVs. Similar levels of Anc80 transduction were found throughout the cochlea from base to apex in a total of three Anc80-injected mice (FIG. 2A, B, C). Low magnification views of the cochlear apex (FIG. 8A) showed strong eGFP expression far from the injection site. High magnification images of the base reveal 100% IHC and 95% OHC transduction (FIG. 8B).

Figure 9:
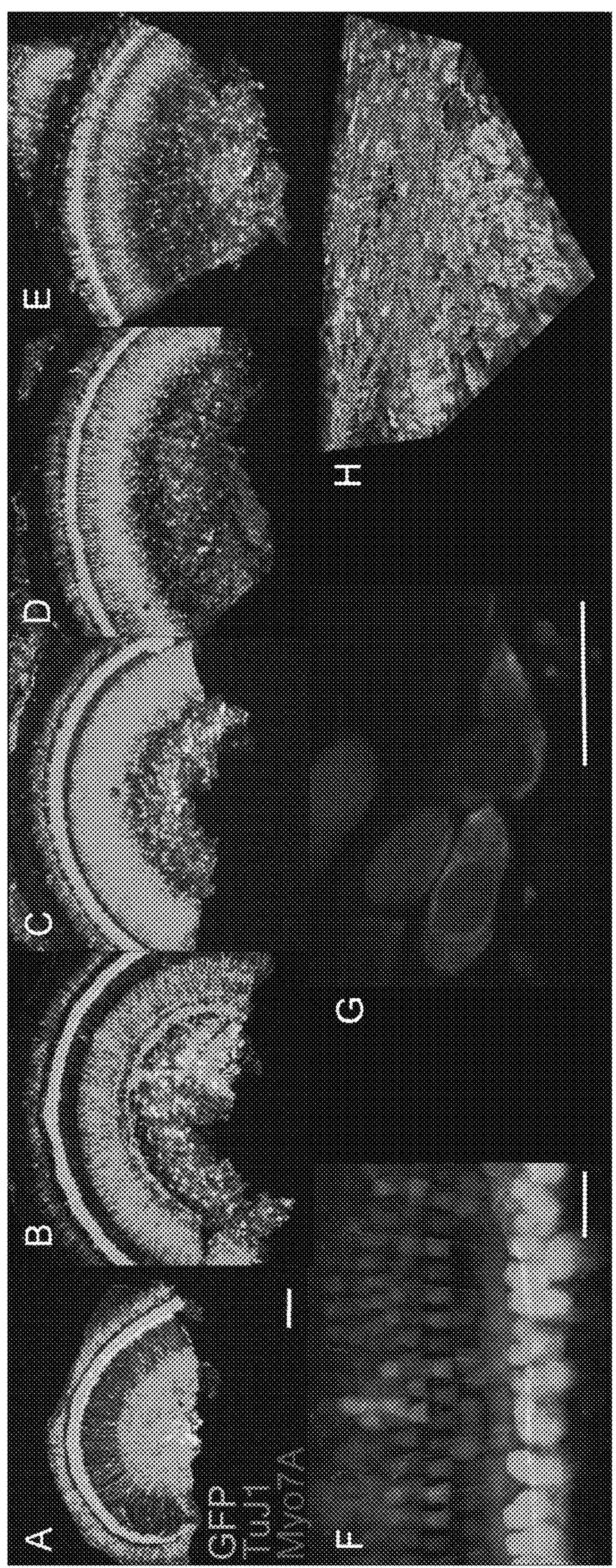
FIGS. 9A-9H are images showing bilateral cochlear transduction from base to apex in mouse cochleae evaluated for eGFP transgene expression in histological sections stained for TuJ1 (Red) and Myo7A (Mangenta). Efficient Anc80 transduction was observed in the injected cochlea extending up to apex (FIGS. 9A/9F) and also in the contralateral uninjected ear (FIGS. 9B-9E=from apex to base). Close-up image of eGFP-positive and TuJ1-positive spiral ganglion neurons (FIG. 9G). Reconstructed 3D image for SGN evaluation of Anc80 transduction (FIG. 9H). Scale bars 100 μm (FIGS. 9A-9E) and 20 μm (FIGS. 9F/9G).
Figure 10:
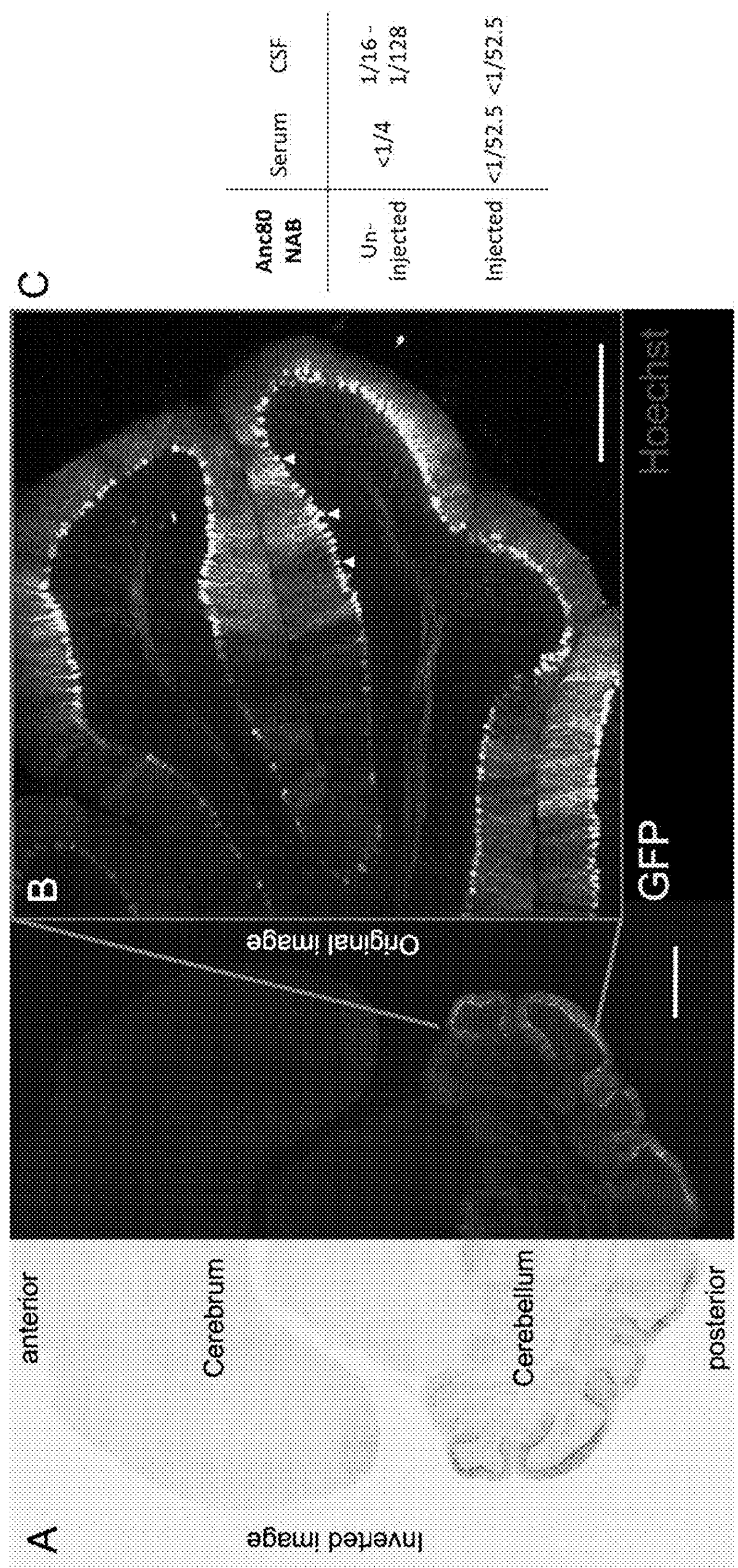
FIGS. 10A-10C are representations of microscopic images showing an axial section of a mouse brain after unilateral cochlear injection with Anc80 (FIG. 10A). Predominant expression was observed in the cerebellum, in particular Purkinje cells (white arrowheads) (FIG. 10B). Scale bars 1 mm (FIG. 10A) and 300 μm (FIG. 10B).

In some animals, robust eGFP expression was found in the contralateral uninjected ear (FIG. 9). In mice, the cochlear aqueduct is patent providing a fluid path from the cochlear perilymph into the CSF, the contralateral aqueduct and into the contralateral cochlea. As such, it was also investigated whether Anc80-eGFP injected via the RWM was capable of transducing neurons in the brain. Indeed, cross-sections of the cerebellum revealed strong eGFP expression in cerebellar Purkinje neurons (FIG. 10A, 10B).

Since some forms of genetic deafness also cause vestibular dysfunction, Anc80 may be a useful vector for gene delivery into human vestibular organs. To investigate this possibility, human vestibular epithelia were harvested from four adult patients undergoing resection of vestibular schwannoma tumors; the sensory epithelium was placed in culture as previously described (Kesser et al., 2007, Gene Ther., 14:1121-31).

Figure 3:
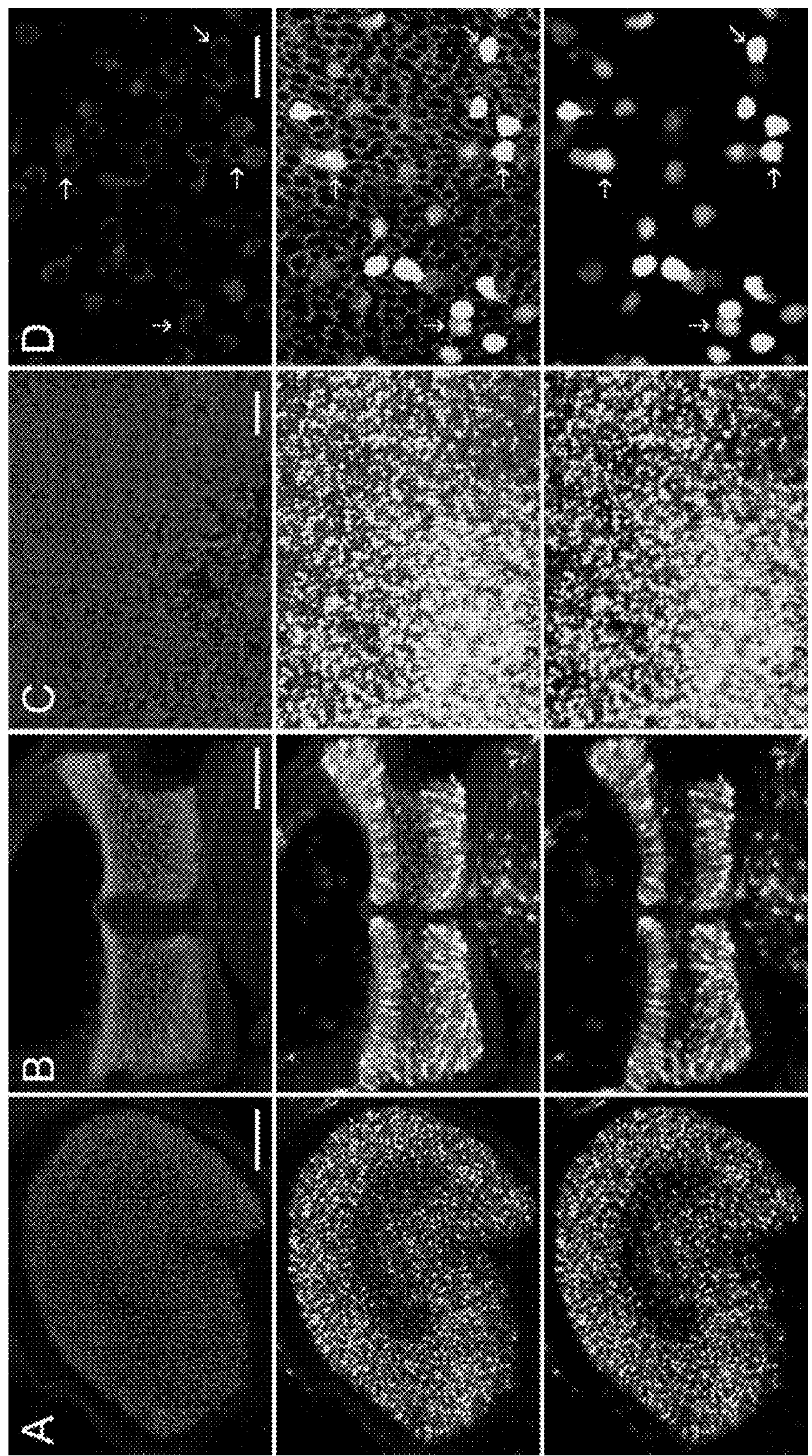
FIGS. 3A-3D are images showing Anc80-eGFP transduction in vestibular sensory epithelia.

For AAV transduced samples, FIG. 3C reveal strong eGFP fluorescence throughout the human vestibular epithelium in both hair cells and supporting cells. A high-magnification view in an epithelium counterstained with Myo7A in FIG. 3D revealed that 83% (19/23) of Myo7A-positive hair cells were also eGFP-positive, suggesting that Anc80 can transduce both mouse and human hair cells efficiently.

Example 1D—Immunological Assays

Antibody titers against Anc80 in CSF and serum were determined through neutralization assays (Zinn et al., 2015, Cell Reports, 12:1056-68). Using a 96-well format, heat-inactivated CSF or serum samples (collected as described above) were serially diluted in serum free medium (Life Technologies, Carlsbad, CA), and then treated with Anc80-luciferase ($10^6$ GC/well) for 1 hour at 37° C. The sample/Anc80-luciferase mix was then transferred onto HEK293 cells, which were treated with adenovirus (MOI 20) the day before. After 1 hour at 37° C., diluted serum medium (1 part serum-free, 2 parts with serum) was added to each well.

Two days later, the cells were treated with lysis buffer (Promega, Madison, WI) and frozen at −80° C. for 30 minutes. The cells were then thawed at 37° C. for 15 minutes before being treated with substrate buffer (Tris-HCl, MgCl2, ATP (Life Technologies, Carlsbad, CA), D-Luciferin (Caliper Life Sciences, Hopkinton, MA)). Luminescence output was read using the Synergy BioTek Plate Reader (BioTek, Winooski, VT).

A low level of neutralization against the vector was detectable in serum of injected mice, but not in CSF, at the level of sensitivity of the assay and sampling (FIG. 10C).

Example 1E—Hair Cell Electrophysiology

Cochleae were excised, mounted on glass coverslips and viewed on an Axio Examiner.A1 upright microscope (Carl Zeiss, Oberkochen, Germany) equipped with a 63× water-immersion objective and differential interference contrast optics. Electrophysiological recordings were performed at room temperature (22° C.-24° C.) in standard solutions containing (in mM): 137 NaCl, 5.8 KCl, 10 HEPES, 0.7 $NaH_2PO_4$, 1.3 $CaCl_2$), 0.9 $MgCl_2$, and 5.6 D-glucose, vitamins (1:100), and amino acids (1:50) as in MEM (Life Technologies, Carlsbad, CA) (pH 7.4; ~310 mOsm/kg).

Recording electrodes (3-4 MΩ) were pulled from R-6 glass (King Precision Glass, Claremont, CA) and filled with intracellular solution containing (in mM): 140 CsCl, 5 EGTA-KOH, 5 HEPES, 2.5 $Na_2ATP$, 3.5 $MgCl_2$, and 0.1 $CaCl_2$) (pH 7.4; ~280 mOsm/kg). The whole-cell, tight-seal technique was used to record mechanotransduction currents using an Axopatch 200B (Molecular Devices, Sunnyvale, CA). Hair cells were held at −84 mV. Currents were filtered at 5 kHz with a low-pass Bessel filter, digitized at ≥20 kHz with a 12-bit acquisition board (Digidata 1440A, Molecular Devices, Sunnyvale, CA), and recorded using pCLAMP 10 software (Molecular Devices, Sunnyvale, CA).

Hair bundles from IHCs and OHCs were deflected using stiff glass probes mounted on a PICMA chip piezo actuator (Physik Instrumente, Karlsruhe, Germany) driven by an LVPZT amplifier (E-500.00, Physik Instrumente, Karlsruhe, Germany) and filtered with an 8-pole Bessel filter (Model 3384 filter, Krohn-Hite Corporation, Brockton, MA) at 40 kHz to eliminate residual pipette resonance. Stiff glass probes were designed to fit into the concave aspect of the array of hair cell stereocilia for whole-bundle recordings (3-4 μm diameter for OHCs and 4-5 μm diameter for IHCs). For the whole cell electrophysiology recording at >P10, cochlea tissues were dissected at P5-7 and incubated in MEM(1×)+GlutaMAX™-I medium with 1% FBS at 37° C., 5% $CO_2$ for up to 30 days.

Representative currents evoked by hair bundle deflections from P7 OHCs and P35 IHCs revealed no differences in amplitude, sensitivity or kinetics, between eGFP positive and eGFP-negative control cells (FIG. 2D). 51 eGFP positive and 52 eGFP-negative hair cells were recorded from all regions of the cochlea and from ages between one and five weeks after exposure to Anc80. Responses were indistinguishable from wild-type in all cases (FIG. 2E), which confirmed that Anc80 transduction had no detrimental effects on sensory cell function.

Example 1F—Hearing Tests

Auditory brainstem response (ABR) and distortion product otoacoustic emissions (DPOAE) data were collected as described previously (Askew et al., 2015, Science Translational Med., 7:285ra108). DPOAE is an assay for proper cochlear amplification and tuning and is a sensitive measure of outer hair cell viability (Guinan et al., 2012, Hearing Res., 293:12-20). Stimuli tested in anesthetized mice varied between 10 and 90 dB sound pressure level at frequencies of 5.6, 8, 11.3, 16, 22.6, and 32 kHz. Four Anc80-injected ears and four uninjected ears and one negative control ear with injection damage without eGFP fluorescence were analyzed at P28-P30.

Minimal sound thresholds required to evoke ABRs were plotted (FIG. 2F) and revealed no difference in threshold between injected and uninjected ears. Histological analysis revealed strong eGFP fluorescence in all four injected ears (data not shown). In one case, there were no eGFP-positive cells and ABR thresholds were elevated (FIG. 2F), suggesting the injection failed and that the needle may have breached the cochlear duct and caused permanent damage. Despite robust outer hair cell transduction by Anc80-eGFP, no difference was found in DPOAE thresholds relative to uninjected control ears (FIG. 2G). Thus, data from ABRs and DPOAEs indicate that RWM injection, Anc80 transduction and transgene expression in IHCs and OHCs are all safe for auditory function.

Example 1G—Rotarod Test

Five C57BL/6 mice were tested for balance behavior on the rotarod device. Mice with impaired vestibular function are known to perform poorly on the rotarod device (Parker & Bitner-Glindzicz, 2015, Archives Dis. Childhood, 100: 271-8). Previous studies highlighted the ability of this rotarod test to detect balance dysfunction when only one ear is affected (Fukui & Raphael, 2013, Hearing Res., 297:99-105; Geleoc & Holt, 2014, Science, 344:1241062). Three mice injected at P1 and tested at P36 and two uninjected control mice at P79. All mice were tested using the following rotarod protocol. On day one, mice were trained to balance on a rod that was rotating at four RPM for five minutes. On day two, the mice were tested in five trials with each trial separated by five minutes. For each trial, the rod accelerated one RPM (Fukui & Rapheal, 2013, Hearing Res., 297:99-105) from a starting rate of two RPM. The time (in seconds) was recorded until the mice fell off the device.

Figure 11:
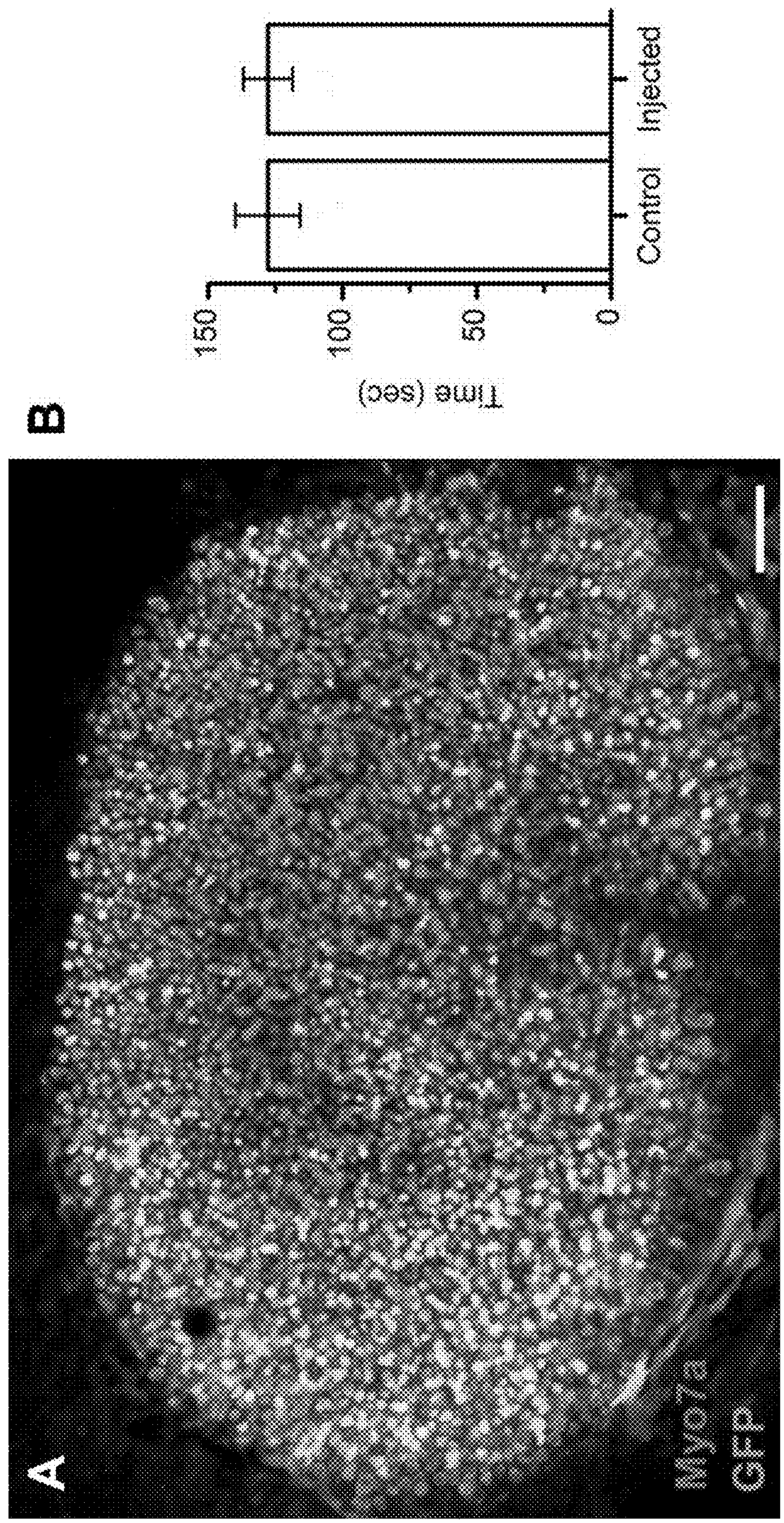
FIGS. 11A-11B are an image and a graph, respectively, showing vestibular function following Anc80 cochlear transduction. Mice were injected with Anc80-eGFP and evaluated for expression and balance function on the rotarod device.

Since the perilymphatic solutions of the cochlea are continuous with those of the vestibular labyrinth, it was evaluated whether Anc80-eGFP injected via the cochlear RWM would transduce vestibular sensory organs. Indeed, whole-mounts of vestibular epithelia revealed robust eGFP expression in both type I and type II hair cells of the utricle, a vestibular organ sensitive to gravity and linear head movements and in the semicircular canals, which are sensitive to rotational head movements (FIG. 3A, 3B). Thus, to address the safety concern that Anc80 transduction may affect balance, injected mice with confirmed vestibular expression performed the rotarod test for vestibular function similarly to uninjected controls (FIG. 11).

Part 2—Gene Therapy Restores Function in a Mouse Model of Usher Syndrome

Example 2—Mouse Model of Usher Syndrome

The following methods and materials were used in Example 2.

Tissue Preparation

Utricle and organ of Corti from Ush1c c.216G>A heterozygous or homozygous mutant mice were harvested from postnatal day 0 to 8 (P0 to P8) for electrophysiological studies. Postnatal mouse pups were killed by rapid decapitation. The temporal bones were excised and bathed in MEM (Invitrogen, Carlsbad, CA) supplemented with 10 mM HEPES (pH 7.4). The organ of Corti was dissected away without the use of enzyme as described previously. Utricles were removed after 10 min protease treatment (Protease XXIV, Sigma) at 0.1 mg/ml. The excised organs were mounted on round glass coverslips. A pair of thin glass fibers previously glued to the coverslip was placed on the edge of the tissue to stabilize it in a flat position. Tissues were either used acutely or kept in culture in presence of 1% Fetal Bovine Serum. Cultures were maintained for 7 to 8 days and the media was replaced every 2 to 3 days for experiments that involved viral vectors infection in vitro.

Animals

Ush1c c.216G>A knock-in mice were obtained from Louisiana State University Health Science Center. The imported strain while on a C57BL6 background were previously bred out of the Cdh23 (Ahl) mutation causing age related hearing loss. Mice were genotyped using toe clip (before P8) or ear punch (after P8) and PCR was performed as described previously (Lentz et al., 2007, Mutat. Res., 616:139-44). For all studies, both male and female mice were used in approximately equal proportions. No randomization paradigm was otherwise applied.

Viral Vector Generation

Total RNA was isolated from cochleae of c.216AA mutant mice (RNAqueous micro kit, Ambion) and reverse transcribed with QuantiTect Reverse Transcription kit (Qiagen). The cDNA of trunc-harmonin was amplified by PCR with Platinum Taq DNA polymerase High Fidelity (Invitrogen) and primers: Trunc-harmonin.F(KpnI) GAG GTA CCA TGG ACC GGA AGG TGG CCC GAG (SEQ ID NO:9); Trunc-harmomin.RV(BamHI) CAG GAT CCG GAC AAT TTC ATC CCC TAC (SEQ ID NO:10). The 387 bp PCR product was cloned with TA cloning kit (Invitrogen), and confirmed by sequencing. To generate a GFP fusion construct, the truncated harmonin fragment was subcloned into pEGFP-C1 with KpnI and BamHI. The NheI-XbaI EGFP::trunc-harmonin cDNA was transferred into an AAV shuttle vector. Custom vectors were packaged with AAV2 inverted terminal repeats (ITRs) into the AAV1 capsid where the transgene cassette was driven by a CMV promoter (AAV2/1.CMV.EGFP::trunc-harmomin.hGH, 1.92 E14gc/m, BCH).

Harmonin-a1 and harmonin-b1 plasmid were prepared in our laboratory from EGFP tagged labeled constructs graciously provided by Lily Zheng and James Bartles (Zheng et al., 2010, J. Neurosci., 30:7187-201) (Department of Cell and Molecular Biology, Northwestern University, Feinberg School of medicine, Chicago, IL). Harmonin-a1 was originally obtained from mouse kidney and harmonin-b1 from isolated mouse cochlea sensory epithelium. The harmonin-a1 construct was further modified to replace the EGFP tag with tdTomato at its N terminal end. Fluorescently labeled and unlabeled constructs were packaged into AAV vectors. Viral vectors were generated by the viral core facility at Boston Children's Hospital and the Gene Transfer Vector Core at the Massachusetts Eye and Ear Infirmary. The following vectors were generated: AAV2/1.CMV.tdTomato::harmonin-a1 4.33 10^13 gc/ml (BCH); AAV2/1.CMV.EGFP::harmonin-b1 2.73 564 10^14 gc/ml (BCH); AAV2/1.CMV.EGFP-harmonin-a1: 2.81 10^12 gc/ml (MEEI); AAV2/1.CMV.EGFP-trunc-harmonin; 1.92 10^14 gc/ml (BCH); AAV2/Anc80.CMV.harmonin-a1: 1.93 10^12 gc/ml (MEEI); AAV2/Anc80.CMV.harmonin-b1: 1.74 10^12 gc/ml (MEEI); AAV2/Anc80.CMV.trunc-harm.WPRE: 9.02 567 10^12 gc/ml (MEEI); For in vitro experiments, 10 μl of concentrated vector was applied to 1 ml MEM supplemented media on acutely dissected tissue in presence of 1% Fetal Bovine Serum for 24 h. Cultures were subsequently maintained for up to 10 days.

Round Window Membrane (RWM) Injection

RWM injections were performed as approved by the Institutional Animal Care and Use Committees at Boston Children's Hospital animal protocol #15-01-2878R. 0.8 μl-1 μl of AAV vectors were injected in neonatal mice P0-P1 and P10-P12. P0-P1 mice were first anesthetized using hypothermia exposure while P10-P12 mice were anesthetized with isoflurane. Upon anesthesia, post-auricular incision was made to expose the otic bulla and visualize the cochlea. Injections were done through the RWM with a glass micropipette controlled by a micromanipulator (Askew et al., 2015, Sci. Transl. Med., 7:295ra108). The volume of the injected materials was controlled at an approximately 0.02 μl/min for 10 min. Standard post-operative care was applied. Sample size for in vivo studies were determined on a continuing basis to optimize the sample size and decrease the variance.

Electrophysiological Recording

Recordings were performed in standard artificial perilymph solution containing (in mM): 144 NaCl, 0.7 $NaH_2PO_4$, 5.8 KCl, 1.3 $CaCl_2$), 0.9 $MgCl_2$, 5.6 D-glucose, and 10 HEPES-NaOH, adjusted to pH 7.4 and 320 mOsmol/kg. Vitamins (1:50) and amino acids (1:100) were added from concentrates (Invitrogen, Carlsbad, CA). Hair cells were viewed from the apical surface using an upright Axioskop FS microscope (Zeiss, Oberkochen, Germany) equipped with a 63× water immersion objective with differential interference contrast optics. Recording pipettes (3-5 MΩ) were pulled from borosilicate capillary glass (Garner Glass, Claremont, CA) and filled with intracellular solution containing (in mM): 135 KCl, 5 EGTA-KOH, 10 HEPES, 2.5 K2ATP, 3.5 $MgCl_2$, 0.1 $CaCl_2$), pH 7.4. Currents were recorded under whole-cell voltage-clamp at a holding potential of −64 mV at room temperature. Data were acquired using an Axopatch Multiclamp 700A or Axopatch 200A (Molecular devices, Palo Alto, CA) filtered at 10 kHz with a low pass Bessel filter, digitized at ≥20 kHz with a 12-bit acquisition board (Digidata 1322) and pClamp 8.2 and 10.5 (Molecular Devices, Palo Alto, CA). Data were analyzed offline with OriginLab software and are presented as means±standard deviations unless otherwise noted.

Statistical Analyses

Test and control vectors were evaluated in at least three mice per group at each time point to ensure reproducibility. Sample sizes are noted in figure legends. All animals with successful RWM injection were included in the study analysis. Those animals with unsuccessful injection were excluded from the mean but included in the legend for full disclosure. Injection success was determined according to ABR recovery with thresholds >90 dB SPL. Statistical analyses were performed with Origin 2016 (OriginLab Corporation). Data are presented as means±standard deviations (SD) or standard error of the mean (SEM) as noted in the text and figure legend. One-way analysis of variance (ANOVA) was used to determine significant differences between the means.

Example 2A—Scanning Electron Microscopy (SEM) in the Mouse Usher Model

SEM was performed at P7, P18 and -P42 (6 weeks) along the organ of Corti of control and mutant mice. P18 SEM was performed in collaboration with Dr. Edwin Rubel at the University of Washington. Inner ears were fixed in 4% glutaraldehyde in 0.1 M sodium phosphate at 4° C. overnight. The next day specimens were rinsed three times in 0.1 M sodium phosphate buffer (PB) and post-fixed in 1% osmium tetroxide in 0.1 M PB for 30 min in an ice bath. Specimens were then rinsed in 0.1 M PB and dehydrated through a graded ethanol series: 35%, 70%, 95%, and 100% (×2). Samples were critical point dried, mounted on SEM stubs, and sputter coated with Au/Pd. SEM was performed using a JEOL JSM-840A scanning electron microscope. A similar preparation was performed for P8 and 6 weeks stages. Organ of Corti explants were fixed in 2.5% glutaraldehyde in 0.1 M cacodylate buffer (Electron Microscopy Sciences) supplemented with 2 mM $CaCl_2$) for 1 h at room temperature. Specimens were dehydrated in a graded series of acetone, critical-point dried from liquid $CO_2$, sputter-coated with 4-5 nm of platinum (Q150T, Quorum Technologies, United Kingdom), and observed with a field emission scanning electron microscope (S-4800, Hitachi, Japan).

Homozygous c.216AA mutant mice are deaf and show circling and head tossing behaviors characteristics of vestibular dysfunction. Previous work (Lentz et al., 2010, Dev., Neurobiol., 70:253-67) described pronounced inner and outer hair cell degeneration at the base of the cochlea at P30. Degeneration and hair cell death was also observed in the middle turn, while the apical portion of the organ was better preserved at 1 month of age. It was hypothesized that hair cell degeneration occurs progressively during development of the inner ear organs and, to assess hair cell survival at earlier stages, SEM analysis was performed along the organ of Corti at P8 and P18. Outer hair cells (OHCs) and inner hair cells (IHCs) of heterozygous c.216GA mice were preserved and their bundles were properly oriented at these ages (FIG. 12A-12C, 12G, 12I and FIG. 19A-19C, 19K). However, disorganized hair bundles were evident along the entire length of the organ of Corti in homozygous c.216AA mice at both ages analyzed (FIG. 12D-12F, 12H, 12J-12L and FIG. 19D-19J, 19L). At P8, IHC bundles were mildly disorganized at the base, mid and apical regions (FIG. 12D-12F, 12J). Numerous IHC bundles displayed a wavy pattern and mild disorganization of the stereocilia rows (FIG. 12J). While many OHCs of c.216AA mutant mice possessed well-preserved hair bundles (FIG. 12H, 12K), fragmented and disorganized hair bundles were evident sporadically along the organ (FIG. 12D-12F, 12L). Disruption was more pronounced at P18, though the majority of hair cells were still present as previously reported (Lentz et al., 2013, Nat. Med., 19:345-50) (FIG. 19D-19F).

Figure 18:
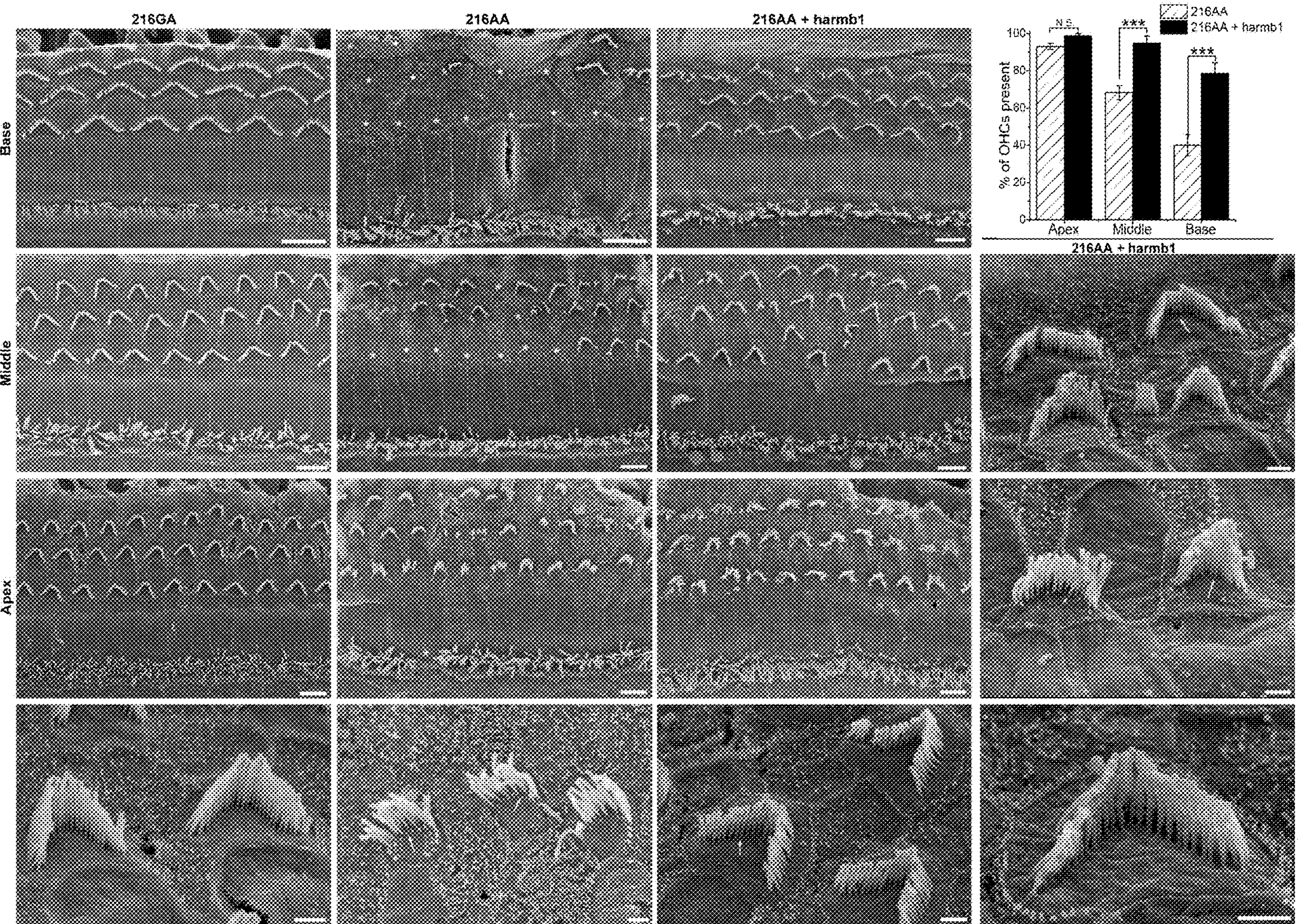
FIG. 18 are scanning electron microscopy images of the organ of Corti in mice injected with Anc80 harmonin-b1. Basal, Middle and Apical regions of the organ of Corti were imaged in c.216GA, c.216AA and c.216AA mice. OHC and IHC hair bundles were preserved in c.216GA mice but appeared disorganized along the organ of Corti in c.216AA mice. Noticeable hair cell loss (asterisk) and hair bundle disorganization was observed in c.216AA mice with more pronounced degeneration in the basal end of the organ. Hair bundles of c.216AA mice lacked normal stereocilia rows. The shorter rows appeared to be retracted while the tallest rows were maintained in c.216AA mice (arrow). While hair cell loss and bundle disorganization were still evident in rescued c.216AA mice, hair cell survival was noticeably higher in the basal and middle regions of the Organ. Hair cell counts are summarized in the bar graph. A total of 1824 cells were counted in c.216AA mice and 792 in rescued c.216AA mice. Mean±SE. High magnification imaging reveals rescue of the staircase array in injected c.216AA mice (arrow) in many but not all cells (arrowhead). Scale bar low magnification: 5 μm; high magnification: 1 μm.

To assess hair bundle morphology in mice that have undergone gene therapy with harmonin-b1, temporal bones of 6-week old untreated (or uninjected) and treated (or injected) mice were prepared for SEM analysis. Untreated c.216AA mice displayed severe hair cells loss at the basal and middle regions of the organ (FIG. 18). In the basal region, OHCs were mostly absent in the first row and present sporadically in the second and third rows. In the middle region of the organ, the first row of OHCs was also largely absent. Milder phenotypes were observed in the apical end. High magnification SEM also revealed severely disorganized hair bundles along the entire length of the organ of c.216AA mutant mice. Remarkably, in 6 weeks old c.216AA mice, no hair bundles were observed that retained the typical staircase structure with all three rows of stereocilia. Instead, hair cells from c.216AA mice displayed disorganized hair bundles with retracted stereocilia along the first row, abnormal second row and fairly preserved tallest row. In contrast, reduced hair cell loss and normal hair bundles were observed in c.216AA mice after treatment with harmonin-b1. Hair cells counts were estimated from the presence or absence of hair bundles in representative fields of view.

The data revealed pronounced preservation of hair cell number in injected mice from the base to the apex of the organ, from 40 to 79% in the base, 68 to 95% in the middle and 93 to 99% in the apex (n=1824 cells from n=4 c.216AA mice ears and n=792 from n=2 rescued c.216AA ears). Although abnormal hair bundles were still evident in harmonin-b1 injected mice, most hair bundles possessed three rows of stereocilia and had morphology almost indistinguishable from their heterozygous controls (FIG. 18).

Example 2B-FM1-43 Imaging in the Usher Mouse Model 5 micromolar FM1-43 (Invitrogen) was diluted in extracellular recording solution and applied to tissues for 10 seconds and then washed 3 times in extracellular recording solution to remove excess dye and prevent uptake via endocytosis. After 5 minutes the intracellular FM1-43 was imaged using an epifluorescence light source, differential interference contrast optics, and an FM1-43 filter set (Chroma Technologies) on a Zeiss Axioscope FS plus with water immersion 20×, 40×, and 63× objectives. Images were captured at 16-bit with a CCD camera and Argus-20 image processor (Hamamatsu) using background fluorescence subtraction. The same gain and contrast settings were maintained for the acquisition of all images and analyzed offline with Adobe Photoshop or Image-J software.

To assess hair cell function at earlier stages, FM1-43 uptake in acutely dissected inner ear organs was analyzed at P4. Upon brief applications (<10 s), FM1-43 permeates hair cells that possess functional mechanosensitive channels. Uniform FM1-43 uptake was observed in hair cells of c.216GA mice (FIG. 13A), but the level of uptake varied among OHCs of c.216AA mice, suggesting that some, but not all, cells retained functional transduction channels (FIG. 13B). Similar observations were made along the entire length of the cochlea. No tonotopic differences were noted. FM1-43 uptake also decreased in IHCs of c.216AA mice during the first postnatal week (data not shown). FM1-43 uptake also was assessed in utricle hair cells of mutant mice. Interestingly, in c.216AA mutant mice, uptake was restricted to the extra-striola region at P6, suggesting that hair cells of the striola region lack mechanosensitive channels open at rest (FIG. 13C, 13D).

Example 2C—Mechanical Stimulation in the Usher Mouse Model

OHCs and IHCs: Mechanical stimuli were transmitted via a stiff glass probe mounted on a one-524 dimensional PICMA chip piezo actuator (Physik Instruments, Waldbronn, Gemamy) driven by a 400 mA ENV400 Amplifier (Piezosystem Jena Germany). The tip of the probe was fired polished (Fire polisher, H602, World Precision Instruments Inc., Sarasota, FL) to fit stereociliary bundle (Stauffer & Holt, 2007, J. Neurophysiol., 98:3360-9). Deflections were evoked by applying voltage steps filtered with an 8-pole Bessel filter (Khron-Hite, 528 Brockton, MA) at 50 kHz to eliminate residual pipette resonance. Hair bundle deflections were monitored using a C2400 CCD camera (Hamamatsu, Japan). Voltage steps were used to calibrate the motion of the stimulus probe around ±2 μm of its rest position. Video images of the probe were recorded to confirm absence of off-axis motion and calibrate the probe motion (spatial resolution of ~4 nm). The 10-90% rise-time of the probe was ~20 μsec.

VHCs: Mechanical stimuli were transmitted via a stiff glass probe mounted on a piezoelectric bimorph element. Coupling was performed by gentle suction of the kinocilium into the stimulus pipette. Deflections were evoked by applying voltage steps to the piezoelectrical device which consisted of two bimorphs mounted in series and directly coupled to the stimulus probe. Voltage steps were controlled by pClamp 8.0 software and filtered with a 8 pole Bessel filter at 1 kHz (Khron-Hite, Brockton, MA). Hair bundle deflections were monitored using a C2400 CCD camera (Hamamatsu, Japan). The motion of the stimulus probe was calibrated around (±2 μm) its rest position prior to the experiments.

Figure 12:
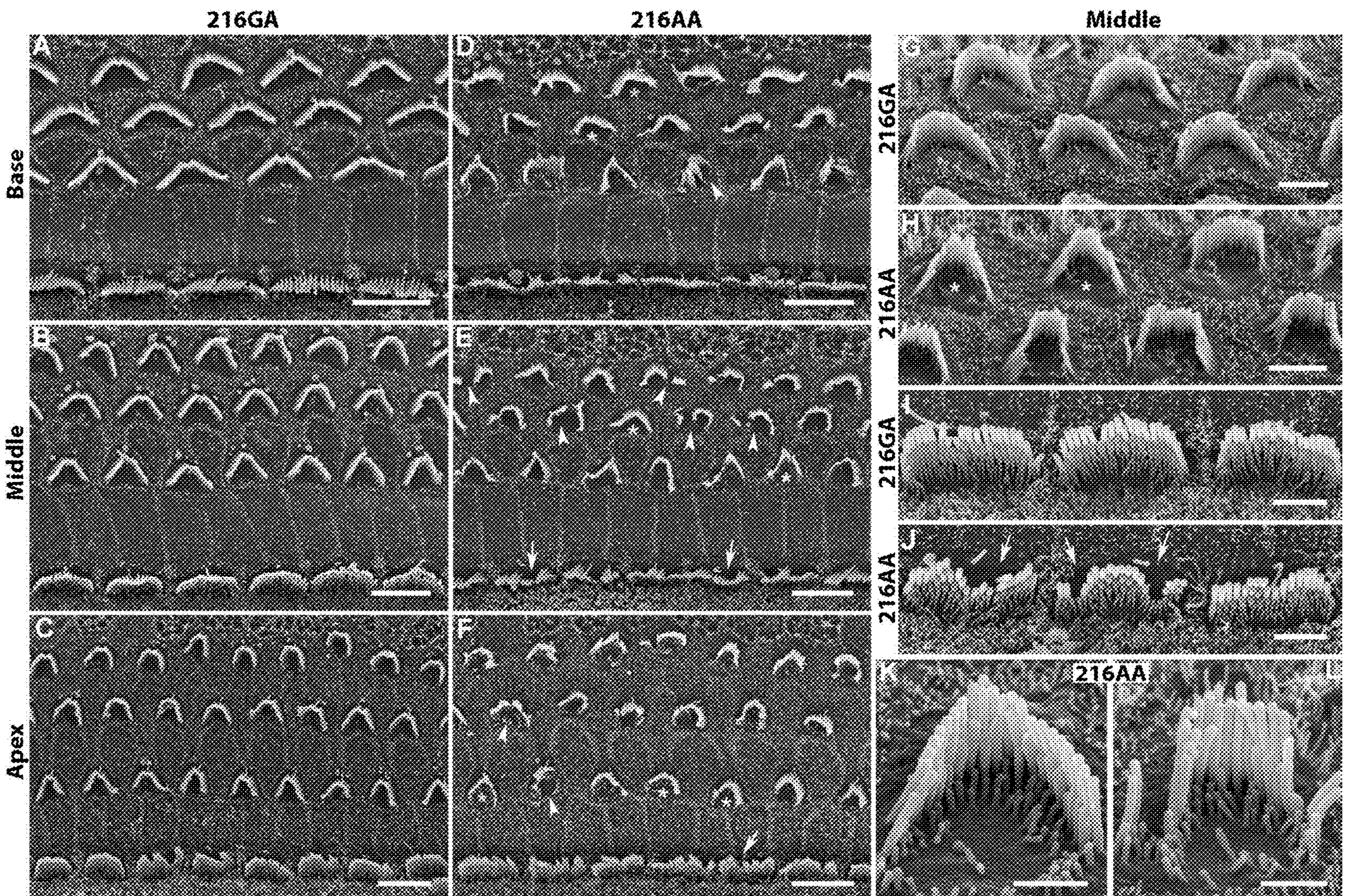
FIGS. 12A-12L are images showing scanning electron microscopy of the organ of *Corti* in Ush1c c.216G>A mutant mice.

During the first postnatal week, auditory and vestibular epithelia retain mechanosensitive hair cells, including some with relatively normal morphology (FIG. 12). In the organ of Corti, recordings were obtained from the middle and apical turns of the cochlea from P3 to P6 c.216AA mice from hair cells with bundles that appeared normal and those with more severely disrupted hair bundles. In c.216AA mutants, OHCs retained mechanosensitivity, although the amplitudes of the responses were significantly reduced by ~63% to 170±80 pA (n=24; p<0.001, FIG. 13E, 13F, 13G). A wide range of response amplitudes was observed in OHCs, between 31 and 292 pA in c.216AA mice. Significant difference (p<0.01) was observed when data were grouped according to hair bundle morphology: currents evoked in mutant hair cells that possessed severely disorganized bundles were smaller than those evoked in mutant cells that had more preserved hair bundles, 120±65 pA (n=9) and 201±74 pA (n=15), respectively. Despite the reduction in current amplitude, hair cell responses to mechanical displacements retained similar properties to those of heterozygous c.216GA mice. Stimulus response [I(X)] curves were fitted using a second-order Boltzmann equation (FIG. 13F) and the fit was used to determine the 10-90% operating range (FIG. 20B). No significant difference (p=0.054) in operating range was observed between OHCs recorded from c.216GA and c.216AA. Similarly, while hair bundles from IHCs of c.216AA mutant mice appeared mildly disrupted under the DIC microscope, transduction currents were significantly reduced at P6 (FIG. 13E, 13F, 13G). At a holding potential of −64 mV, maximum transduction currents in heterozygous c.216GA IHCs (P6-P7) averaged 587±96 pA (n=21) but were reduced by 46% to 316±127 pA (n=19; p<0.001) in c.216AA IHCs. A significant (p<0.01) reduction in the operating range was measured in IHCs of c.216AA mutant mice (FIG. 20G).

Adaptation, defined as a decline in the transduction current in the presence of a constant bundle deflection, was also present in the c.216AA mutant mice. Adaptation kinetics were analyzed using double exponential fits to determine fast and slow components. While both components were slower in IHCs and OHCs from c.216AA mutant mice the difference was only significant for the slow component ($p<0.05$ in OHCs, and $p<0.001$ in IHCs; FIG. 20C, 20D, 20H, 20I). On the other hand, the extent of adaptation measured at Popen=0.5 was significantly less in OHCs and IHCs of c.216AA than c.216GA hair cells (FIG. 20E, 20J; $p<0.001$). Together, these results demonstrate that mechanosensitivity is mildly compromised in inner and outer hair cells of c.216AA mice and importantly that both cell types survive throughout the first postnatal week, a prerequisite for gene therapy and restoration of cellular function.

In vestibular hair cells, a reduction in mechanotransduction currents also was observed in c.216AA mice. In the extra-striola region, c.216AA currents were significantly ($p<0.001$) reduced to 109±30 pA (n=9, P5-P7) versus 231±53 pA (n=8, P6-P7) for c.216GA currents (FIG. 13E, 13F, 13H). Very small or no currents were recorded from hair cell of the striola region (6±13 pA, n=6, P5-P7), in agreement with the absence of FM1-43 uptake in that region (see below; FIG. 13C, 13D). While utricle hair bundles appeared grossly well-preserved by DIC microscopy, transduction currents were significantly reduced or absent from hair cells in the extra-striola and striola, respectively. Thus, with the exception of the striola region, these results suggest that the transduction apparatus is correctly assembled and targeted in mutant mice but that the number of functional complexes is reduced in neonatal mice.

Next, function in c.216AA hair cells exposed to AAV vectors driving harmonin expression was assessed. To enhance the likelihood of functional rescue with exogenous harmonin, untagged harmonin-a1 or harmonin-b1 coding sequences driven by a CMV promoter were packaged into an AAV capsid known as Anc80 (Zinn et al., 2015, Cell Rep., 12:1056-68). As shown herein, the Anc80 capsid transduces 100% of IHCs and 80-90% of OHCs in vivo. It was hypothesized that harmonin-b is required for mechanotransduction in both IHCs and OHCs and is necessary for auditory function in both cell types. RWM injections of AAV2/Anc80.CMV.harmonin-b1 (0.8 μl, 1.9×10^12 gc/ml) and separately a mixture of AAV2/Anc80.CMV.harmonin-a1 (1.7×10^12 gc/ml)+AAV2/Anc80.CMV. harmonin-b1 (0.5 μl+0.5 μl) were performed and mechanotransduction responses assessed 2 weeks after treatment.

Figure 15:
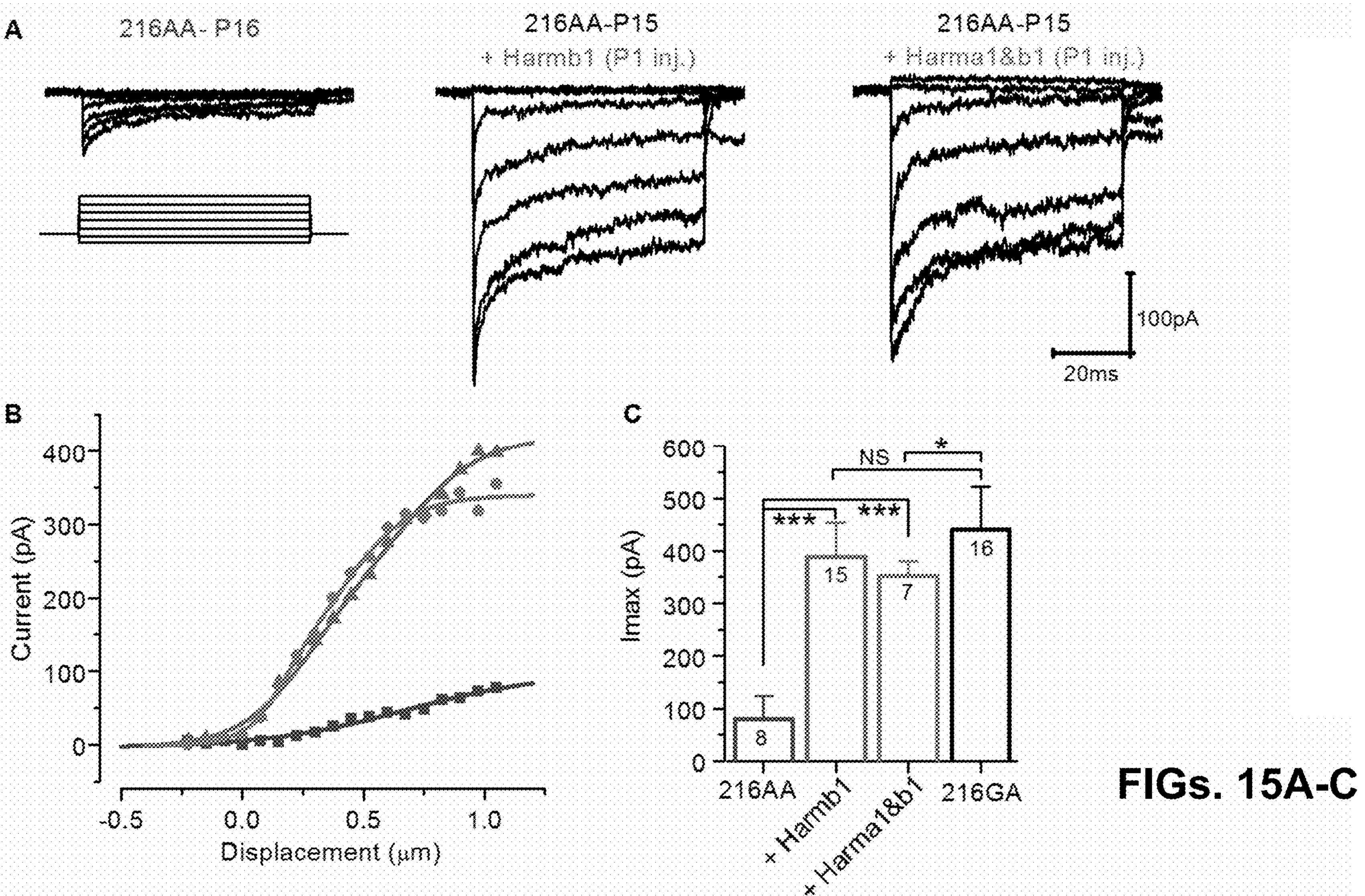
FIG. 15**C shows one-way ANOVA.

Tissue was extracted at P5-P6, before the cochlea became ossified and was maintained in culture for 10 days. Although mature OHCs (>P10) do not survive ex-vivo recording paradigms, robust electrophysiological recordings were obtained from IHCs at the equivalent of P14-P16. Results are presented in FIG. 15. While IHCs from uninjected mice displayed severely reduced transduction currents at P16 (79±43 pA, n=8), recovery of sensory transduction was evident in mice that received the AAV treatment. Significant recovery (*$P<0.001$) was observed in mice injected at P1 with harmonin-b1 or a combination of both b1 and a1 with respective average maximal transduction currents of 388±66 pA (n=15) and 352±28 pA (n=7; FIG. 15**C). Transduction current amplitudes in IHCs after treatment with harmonin-b1 were not significantly different from control c.216GA mice. The level of recovery was not significantly altered by co-injection of harmonin-b1 and harmonin-a1. These results suggest that delivery of exogenous harmonin-b1 via RWM injection at early stages can restore mechanotransduction in IHCs.

Example 2D—Confocal Imaging in the Usher Mouse Model

To prepare the tissue for confocal imaging from postnatal mice P0-P8, fixation was performed for 15 min with 4% Paraformaldehyde (PFA). Permeabilization with 0.010% triton and counterstaining with Alexa Fluor phalloidin (Invitrogen, 1/200) was used to labeled actin filaments. Images were obtained on a LSM700 Zeiss confocal microscope. In older mice (4 to 8 weeks), temporal bones were removed after euthanasia and placed in 4% PFA for 1 hour, followed by decalcification for 24 to 36 hours with 120 mM EDTA. The sensory epithelium was then dissected out and injected as above for immunostaining. Mouse anti-CTBP2 (BD bioscience #612044, 1/200) was applied for 48 hours and counterstained with Alexa Fluor goat anti-mouse (1/200) overnight at 4° C. to label ribbon synapses. Images were acquired on a Zeiss LSM 710 laser confocal microscope (IDDRC Imaging Core grant P30 HD18655) and processed with Zeiss LSM image viewer 4.2.

Figure 14:
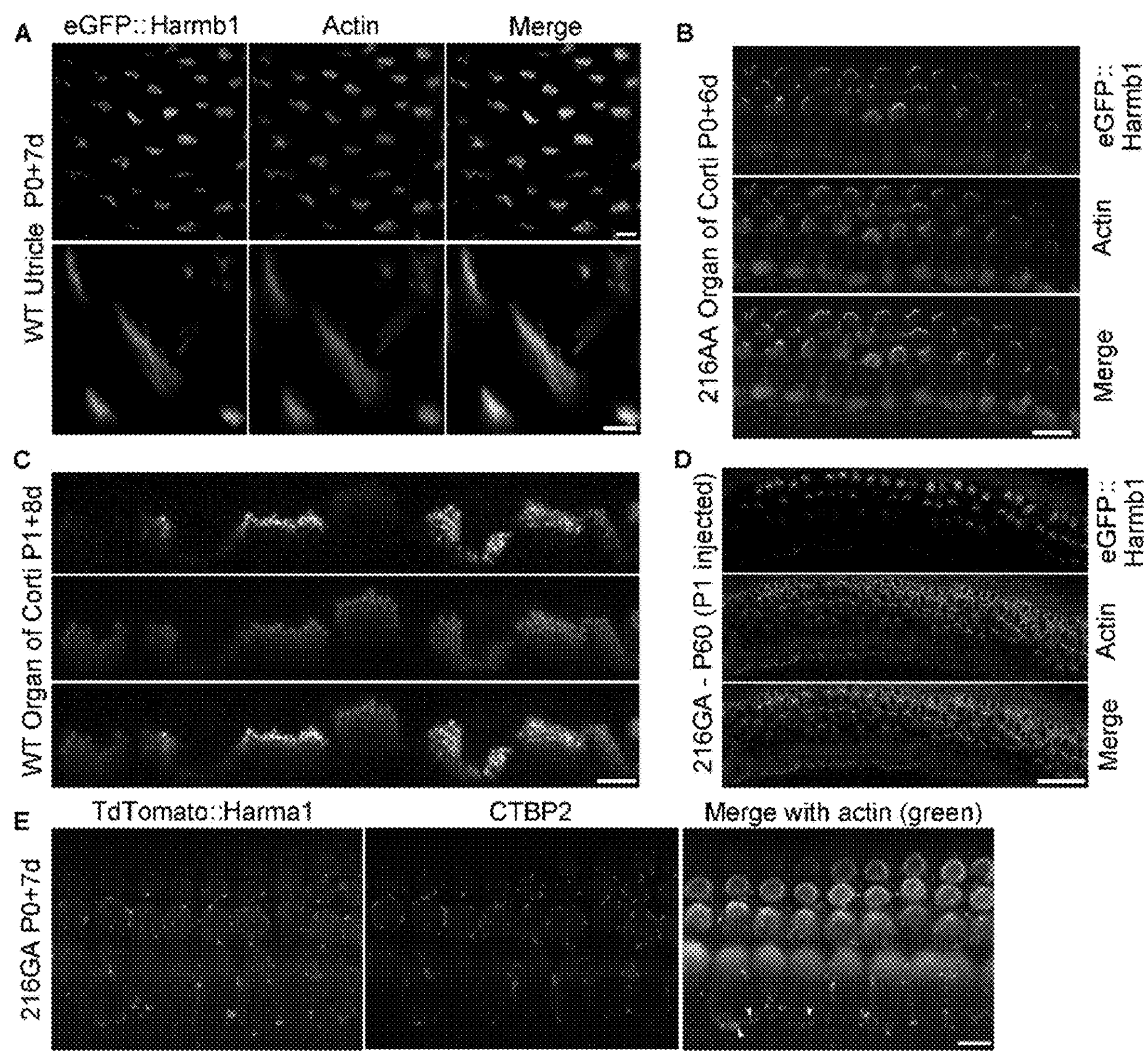
FIGS. 14A-14E are images showing expression and localization of fluorescently labeled harmonin in tissues exposed to adeno-associated viral vectors in vitro and in vivo.

Previous work revealed expression of two alternative splice forms of harmonin in sensory hair cells. To assess the ability of AAV vectors to drive expression of exogenous harmonin splice forms, utricles and organs of Corti from neonatal c.216AA and wild-type (C57BL/6J) mice were exposed to AAV2/1 vectors coding for eGFP fused to the N-terminus of harmonin-b1 (eGFP::harmonin-b1) or tdTomato fused to the 181 N-terminus of harmonin-a1 (tdTomato::harmonin-a1). The vectors were applied either in vitro or in vivo through RWM injection (1 μl) at P1. When applied in vitro, P0-P1 tissues were incubated in the presence of the vectors for 24 hours and maintained in culture for one week. Confocal images show that hair cells of wild-type, c.216GA and c.216AA mice were successfully transduced (FIG. 14A-14C, 14E). EGFP::harmonin-b1 signal was evident at the tips of the stereocilia in VHCs (FIG. 14A), IHCs and OHCs (FIG. 14B, 14C). EGFP signal was also detected at P60 in OHCs and IHCs in the basal portion of the cochlea of mice injected at P1 (FIG. 14D). TdTomato::harmonin-a1 was detected at the base of auditory hair cells (FIG. 14E). Co-staining with a ribbon synapse marker CTBP2 frequently revealed colocalization in P7 IHCs (FIG. 14E) but not in P7 utricles (data not shown).

Localization of exogenous fusion constructs was consistent with previous work that localized harmonin-b to the distal end of stereocilia, near the tip-link insertions and harmonin-a to the synapse.

Example 2E—Auditory Brainstem Responses (ABRs) and Distortion Products (DPOAEs)

ABRs and DPOAEs were recorded from mice anesthetized with xylazine (5-10 mg/kg i.p.) and ketamine (60-100 mg/kg i.p.). Subcutaneous needle electrodes were inserted into the skin a) dorsally between the two ears (reference electrode); b) behind the left pinna (recording electrode); and c) dorsally at the rump of the animal (ground electrode). The meatus at the base of the pinna was trimmed away to expose the ear canal. For ABR recordings the ear canal and hearing apparatus (EPL Acoustic system, MEEI, Boston) were presented with 5-millisec tone pips. The responses were amplified (10,000 times), filtered (0.1-3 kHz), and averaged with an analog-to-digital board in a PC based data-acquisition system (EPL, Cochlear function test suite, MEEI, Boston). Sound level was raised in 5 to 10 dB steps from 0 to 110 dB sound pressure level (decibels SPL). At each level, 512 to 1024 responses were averaged (with stimulus polarity alternated) after “artifact rejection”. Threshold was determined by visual inspection. Data were analyzed and plotted using Origin-2015 (OriginLab Corporation, MA). Thresholds averages±standard deviations are presented unless otherwise stated. For DPOAEs, f1 and f2 primary tones (f2/f1=1.2) were presented with f2 varied between 5.6 and 45.2 kHz in half-octave steps and L1-L2=10 dB SPL. At each f2, L2 was varied between 10 and 80 dB SPL in 10 dB SPL increments. DPOAE threshold was defined from the average spectra as the L2-level eliciting a DPOAE of magnitude 5 dB SPL above the noise floor. The mean noise floor level was under 0 dB SPL across all frequencies. Stimuli were generated with 24-bit digital I-O cards (National Instruments PXI-4461) in a PXI-1042Q chassis, amplified by an SA-1 speaker driver (Tucker-Davis Technologies, Inc.), and delivered from two electrostatic drivers (CUI CDMG15008-03A) in our custom acoustic system. An electret microphone (Knowles FG-23329-P07) at the end of a small probe tube was used to monitor ear-canal sound pressure. The majority of these experiments were not performed under blind conditions.

To determine if truncated harmonin interfered with normal auditory function, Anc80.CMV.trunc-harm vectors were generated to over-express the truncated protein. The vectors were injected via RWM into the inner ears of c.216GA mice. ABR and DPOAES were measured at 4, 6 and 12 weeks and found no difference in thresholds between injected and uninjected c.216GA mice (recordings from 6 weeks old mice shown in FIG. 23C-23D). The data serve as a control for the injection technique, the vector and importantly, argue that exogenous truncated harmonin does not compete with endogenous full-length harmonin, implying that the endogenous truncated form in c.216AA hair cells is unlikely to interfere with exogenous full-length harmonin expressed via gene therapy vectors.

To determine if harmonin gene augmentation can rescue auditory and balance function in Ush1c mice, P0-P1 RWM injections of AAV2/Anc80.CMV.harmonin-a1 (0.8 μl, 1.7×10^12 gc/ml) or AAV2/Anc80.CMV.harmonin-b1 (0.8 μl, 1.9×10^12 gc/ml) were performed and auditory brainstem responses (ABRs), distortion product otoacoustic emissions (DPOAEs), acoustic startle reflexes, open field and rotarod behavior assessed. Mice were assessed at six weeks, a stage at which c.216AA mice suffer from profound hearing loss and vestibular dysfunction. Some of the mice were further tested at 3 and 6 months.

None of the 12 mice injected with AAV2/Anc80.CMV.harmonin-a1 recovered auditory function at 6 weeks (FIG. 16A-16C), suggesting exogenous expression of harmonin-a1 was insufficient for auditory rescue. However, 19 of 25 mice injected with AAV2/Anc80.CMV.harmonin-b1 recovered significant auditory function at 6 weeks. At low frequencies (5.6 to 16 kHz), best ABR thresholds in AAV2/Anc80.CMV.harmonin-b1 injected ears were at 25-30 dB SPL, remarkably similar to thresholds of wild-type mice (FIG. 16A-16B). Partial rescue was observed at 22.6 kHz and little to none at 32 kHz. Rescue of DPOAE thresholds was also evident, consistent with rescue of function in OHCs (FIG. 16C). Eight of the mice that possessed auditory thresholds <45 dB SPL for stimuli 8-11.3 kHz were tested at later stages to assess the longevity of the rescue. From 6 weeks to 3 months, ~10 dB SPL ABR threshold shifts were observed in the low frequency range and ~30 dB SPL in the high frequency range (FIG. 16D). A similar shift was also observed in the DPOAEs thresholds (FIG. 16E). After this time point, ABR thresholds and DPOAEs remained stabled up to 6 months of age (FIG. 16D-16E), the latest time point tested.

Figure 16:
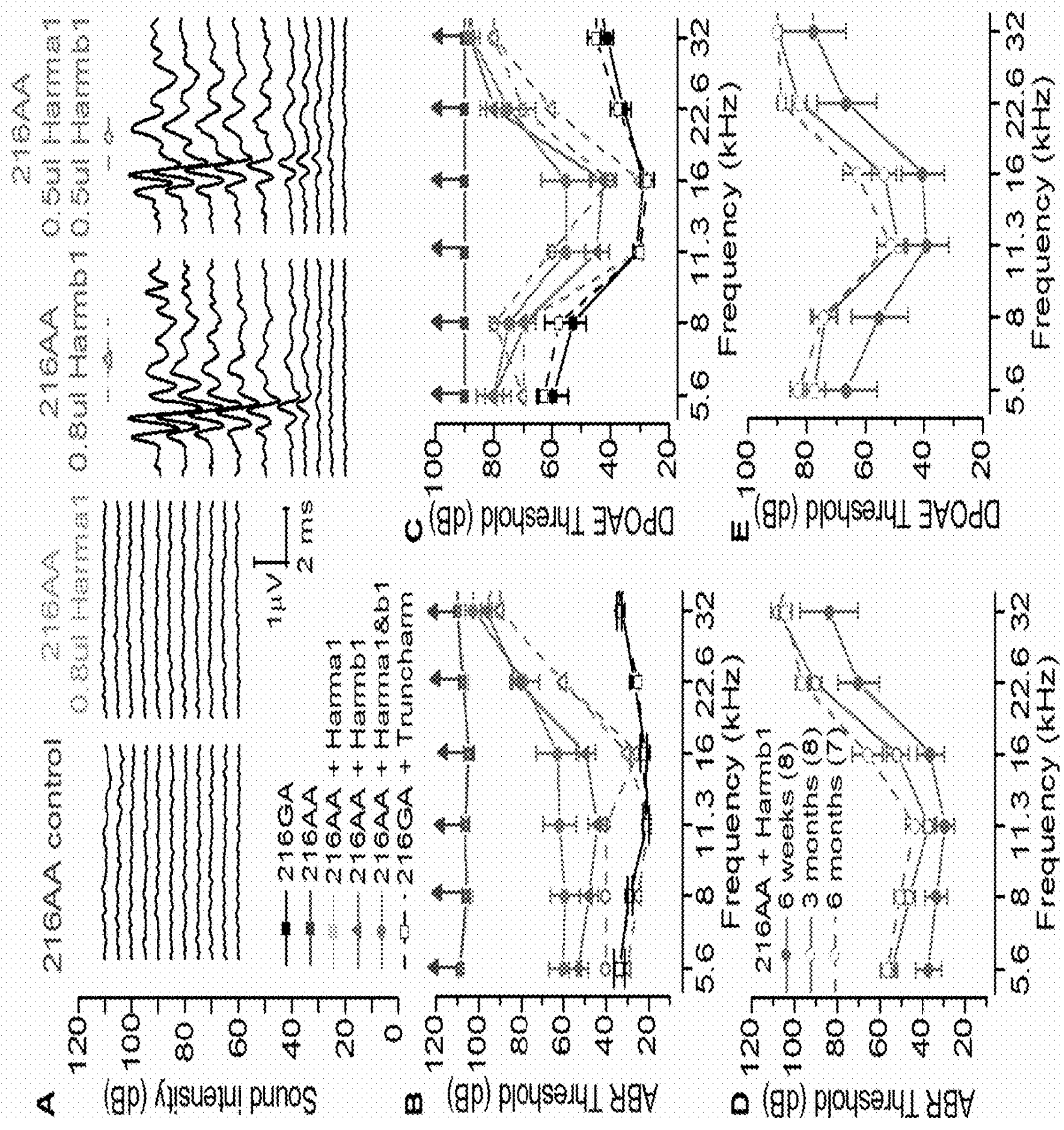
FIGS. 16A-16E are images showing ABR and DPOAE threshold recovery in mice injected with Anc80 harmonin-b1.

To assess whether both harmonin-a1 and harmonin-b1 are required for more complete auditory rescue, particularly at the high frequency end, AAV2/Anc80.CMV.tdTomato::harmonin-a1 (0.5 μl; 238 4.1E^12 gc/ml) and AAV2/Anc80.CMV.eGFP::harmonin-b1 (0.5 μl; 3.0E^12 gc/ml) were co-injected. 65% of the hair cells expressed both harmonin-a1 and harmonin-b1, as evident from cells positive for both fluorescent tags (FIG. 21). Fluorescently labeled harmonin-a1 was occasionally observed in the stereocilia of mice exposed to AAV2/Anc80.CMV.tdTomato::harmonin-a1, perhaps due to over expression. ABR and DPOAE thresholds in mice co-injected with unlabeled harmonin-a1 and harmonin-b1 vectors (FIG. 16) were similar to those injected with harmonin-b1 alone and did not provide further improvement, suggesting that harmonin-a1 may be dispensable for auditory function. Importantly, the data demonstrate that harmonin-b1 alone is sufficient for significant restoration of auditory thresholds at low frequencies (FIG. 16).

To further evaluate the extent of the rescue, ABR waveforms, from mice with thresholds ≤45 dB SPL, were analyzed and compared between eight control c.216GA mice and five c.216AA mice injected with AAV2/Anc80.CMV.harmonin-b1. The analysis for responses at 8-11.3 kHz and 16 kHz revealed normal wave 1 amplitudes (non-significant differences, P>0.2, Student t-test) and longer peak 1 latencies (P>0.001) (FIG. 22), suggesting a possible lag in neurotransmission at the synapse. In many animals, auditory rescue was also observed in the contralateral ear, with ABR thresholds as low as 20 dB SPL at 11.3 kHz (harmonin-b1: average 59.7±5.3 dB SPL, n=15/25; harmonin-a1+-b1: 255 average 76.2±10.3 dB SPL, n=4-6). Diffusion of AAV vectors to the contralateral ear has been previously observed and likely occurs via the perilymphatic duct that remains continuous with the subarachnoid space in newborn mice.

We also examined whether injections at later developmental stages might lead to partial auditory rescue. RWM injections of AAV2/Anc80.CMV.harmonin-b1 (0.8 μl) at P10-P12 were performed and auditory thresholds assessed at 6 weeks. None of the P10-P12 injected mice had detectable DPOAEs and their ABR thresholds did not differ from the uninjected c.216AA control mice (n=10; data not shown), suggesting the window of opportunity for intervention may be limited to early postnatal stages, possibly due to low viral transduction efficiency in older tissue or degeneration of the organ of Corti at later development stages.

Example 2F-RT-PCR in the Usher Mouse Model cDNA was prepared from 6 auditory organs of P2-P3 wild-type, heterozygous and homozygous Ush1c c.216G>A mice using QUANTITECT® Reverse Transcription Kit (Qiagen). cDNA encoding full length (450 bp) or truncated harmonin (−35 bp) was amplified using the following primers: Forward primer mUsh1c_Ex2F: 5' CTC ATT GAA AAT GAC GCA GAG AAG G 3' (SEQ ID NO:11), Reverse mUsh1c_Ex5R: 5' TCT CAC TTT GAT GGA CAC GGT CTT 3' (SEQ ID NO:12). These primers are specific for mouse Ush1c sequences and will amplify both endogenous and AAV2-derived Ush1c as the target sequence is outside the region of the human knocked in portion of the Ush1c c.216A allele. DNA and RNA levels were also assessed from mouse tissue collected at six weeks post-treatment. DNA and RNA were isolated from the cochlea using TRIzol reagent (Life Technologies, Carlsbad, CA) according to the manufacturer's protocol. RNA was reverse transcribed using GoScript reverse transcription system (Promega, Madison, WI). Radiolabeled PCR was carried out using GoTaq Green Master Mix (Promega, Madison, WI). For viral DNA amplification, primers specific for mouse Ush1c: mUsh1c_Ex3F (5'-GAA CCC AAC CGC CTG CCG (SEQ ID NO:13)) and mUsh1c_Ex4WTR (5'-TGC AGA CGG TCC AAG CGT-3' (SEQ ID NO:14)) were used.

These primers will only amplify the viral Ush1c DNA because the homozygous Ush1c.216AA mice have the human USH1C c.216A gene knocked in to exon 3 and 4, replacing the mouse sequence (Lentz et al., 2007, Mutat. Res., 616:139-44). For cDNA amplification of full-length (450 bp) and aberrantly spliced/truncated harmonin (415 bp), the same primers as above were used (mUsh1c_Ex2F and mUsh1c_Ex5R). Gapdh primers were: mGapdh_Ex3F (5'-611 GTG AGG CCG GTG CTG AGT ATG-3' (SEQ ID NO:15)) and mGapdh_Ex4R (5'-GCC AAA GTT GTC ATG GAT GAC-3' (SEQ ID NO:16)). Products were separated on a 6% nondenaturing polyacrylamide gel and quantified using a Typhoon 9400 phosphorimager (GE Healthcare).

Since previous studies raised the possibility that truncated harmonin may disrupt function by competing with full-length harmonin for endogenous binding partners, it was explored whether persistent expression of the truncated protein may limit recovery in c.216AA mice injected with vectors that express exogenous full-length harmonin (FIG. 23A). To address this concern, expression of Ush1c transcripts in c.216GA and c.216AA mice was examined using an RT-PCR assay. Consistent with previous reports, Ush1c transcripts that encoded full-length and truncated harmonin were detected in c.216GA cochleas and only transcripts that encoded truncated harmonin were detected in c.216AA cochleas (FIG. 23B).

To confirm expression of AAV2/Anc80.CMV.harmonin-b1 and explore the relationship between viral expression level and ABR thresholds, DNA and RNA were isolated from injected and contralateral cochleae and quantified by PCR and RT-PCR, respectively. Expression was assessed in six-week old c.216GA and AAV2/Anc80.CMV. harmonin-b1 (0.8 μl; 1.93 10^12 gc/ml)-injected and non-injected c.216AA mice. Samples included two injected mice with good ABR rescue (thresholds ≤35 dB SPL at 11.3 kHz) and two with poor ABR rescue (thresholds ≥90 dB SPL at 11.3 kHz). RNA encoding the correct splice form of harmonin (FIG. 24A) and AAV2/Anc80.CMV. harmonin-b1 DNA (FIG. 24B) were detected in all of the injected cochleae and, to a lesser extent, in the contralateral cochleae of all animals tested.

Figure 25:
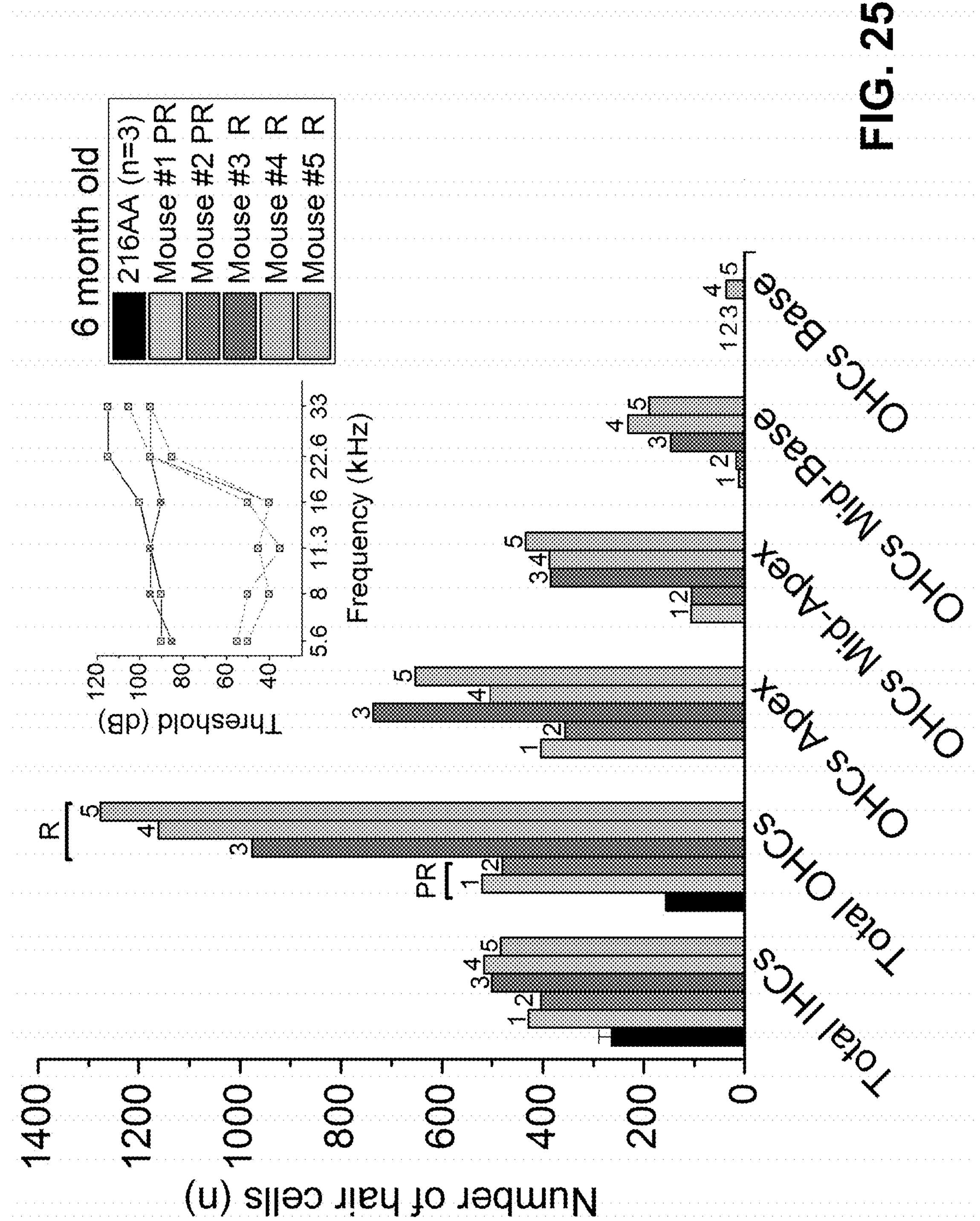
FIG. 25 is a graph showing long term ABR threshold recovery correlated with OHCs survival in the mid to apical region of the auditory organ. Hair cell count across the entire Organ of Corti was performed post-mortem in left ears of three uninjected c.216AA and five injected c.216AA. The total number of IHC and OHCs hair cells was increased in injected mice. Comparison of rescued injected mice with those injected that had poor rescue shows that the number of IHCs was not different but a significant number of OHCs were noted in the rescued mice. Analysis across the entire length of the organ showed the difference can be accounted for as an increase in hair cell survival from the mid to apical regions of the organ. Insert: while two of the mice (mice #1,2) showed poor ABR response thresholds across the entire range tested (>95 dB SPL), three (mice #3,4,5) responded with thresholds ranging 35 and 55 dB SPL for sound stimuli between 5.6 and 16 kHz.

There was variability between animals in ABR thresholds and amount of DNA and RNA expressed (FIG. 24C). However, a strong correlation was found between AAV2/Anc80.CMV.harmonin-b1 DNA levels, the amount of RNA encoding for the correct splice form of harmonin and ABR threshold levels, which suggests that the variability in ABR data may be a direct result of AAV expression. To assess long term hair cell survival in mice that had successful recovery of ABR thresholds, tissue was prepared and the number of IHCs and OHCs counted at 6 months of age from 5 mice (FIG. 25). While the number of IHCs did not vary in the two cohorts, 50% or more OHCs remained in the three mice that showed long term ABR rescue. OHC survival was observed along the entire organ with the exception of the basal turn (FIG. 25).

Example 2G-Acoustic Startle Responses in the Usher Mouse Model

The acoustic startle responses (ASR) were measured using the Startle Monitor (Kinder Scientific). Mice were placed in a small-sized, nonrestrictive, cubical Plexiglas recording chamber (27 cm×10 cm×12.5 cm) fixed on a piezo/plexiglass sensing assembly and allowed to acclimate for 5 min with a 60 dB SPL background white noise. Each session consisted of 35 trials, during which a single noise pulse ranging in 10 dB SPL intensities from 60-120 db SPL was delivered with an inter-trial interval averaging 30 s (25-35 s range). Pulses were arranged in a pseudorandom order, on a constant 60 dB SPL background noise to limit external noise interference. The Startle Monitor system reduced the response to each pulse into measurements of first N, max N, and max time of the response (ms), for calculations of peak startle response (ASR amplitude) and time from stimulus to peak startle response (ASR latency). ASR were all conducted blind.

To assess whether the ABR/DPOAE recovery yielded behaviorally relevant recovery of auditory function, acoustic startle responses was measured in mice injected with AAV2/Anc80.CMV.harmonin-a1, AAV2/Anc80.CMV.harmonin-b1 and those injected with both vectors. Analysis of the startle response to white noise showed partial rescue of the response in 6 weeks old mice injected with AAV2/Anc80.CMV.harmonin-b1 and in mice that were co-injected with both vectors (FIG. 17A). Mice that received harmonin-a1 alone were similar to uninjected c.216AA mice and did not recover startle responses.

Example 2H-Vestibular Assessment in the Usher Mouse Model

Vestibular function was assessed using open field and rotarod balance test. The open field test was conducted using a circular frame measuring 42 cm in diameter, placed inside a sound chamber with overhead LED lighting, set to 30 lux at the center, inside a dimmed room. Mice were placed one at a time inside the circular open field, and allowed to explore for 5 min. Behavior was recorded and tracked using Ethovision XT, enabling measures of distance traveled and velocity. Open field assessments were all conducted blind. The rotarod performance involved placement of mice on a rod in an enclosed housing that began rotating at 4 rpm and accelerated at a rate of 0.1 rpm $s^{-1}$. The mice were placed on the rods on day one for 5 min to get familiarized with the equipment. The next day, the animals were placed on the rods for a total of 5 trials. A 5 min resting period was imposed between trials. The length of time the animals were able to remain on the device before dropping onto the instrumented floor of the housing was displayed on a timer and recorded after each test run.

Since the perilymphatic space is continuous between the cochlea and vestibular labyrinth, AAV vectors injected via RWM may transduce vestibular sensory organs as well. To assess vestibular behavior, mice were tested for their performance on a rotarod. While poor rotarod performance was observed in c.216AA and c.216AA mice injected with AAV2/Anc80.CMV.harmonin-a1 mice (latency to fall <22 sec on average), c.216AA mice injected with AAV2/Anc80.CMV.harmonin-b1 and those co-injected with harmonin-a1 and -b1 vectors maintained balance function on the rotarod for 60-120 seconds, consistent with control c.216GA mice (FIG. 17B).

Recovery in open field behavior was also observed in harmonin-b1 and dual harmonina1 and b1 injected c.216AA mice. Representative open-field exploration traces are plotted in FIG. 17C. c.216GA mice explored the border of the field and displayed minimal full body rotations, whereas c.216AA mice displayed more activity throughout the entire chamber with increased full body rotations quantified as rotations/min (FIG. 17D-17E). Surprisingly, while no ABR rescue was observed in mice injected with AAV2/Anc80.CMV. harmonin-a1, open field data demonstrated recovery of vestibular function to the level of the control mice. Behavior of c.216GA mice injected with AAV2/Anc80.CMV.trunc-harmonin did not differ from the control c.216GA mice, again indicating a lack of interference between truncated and wild-type harmonin (FIG. 17C-17E).

Figure 13:
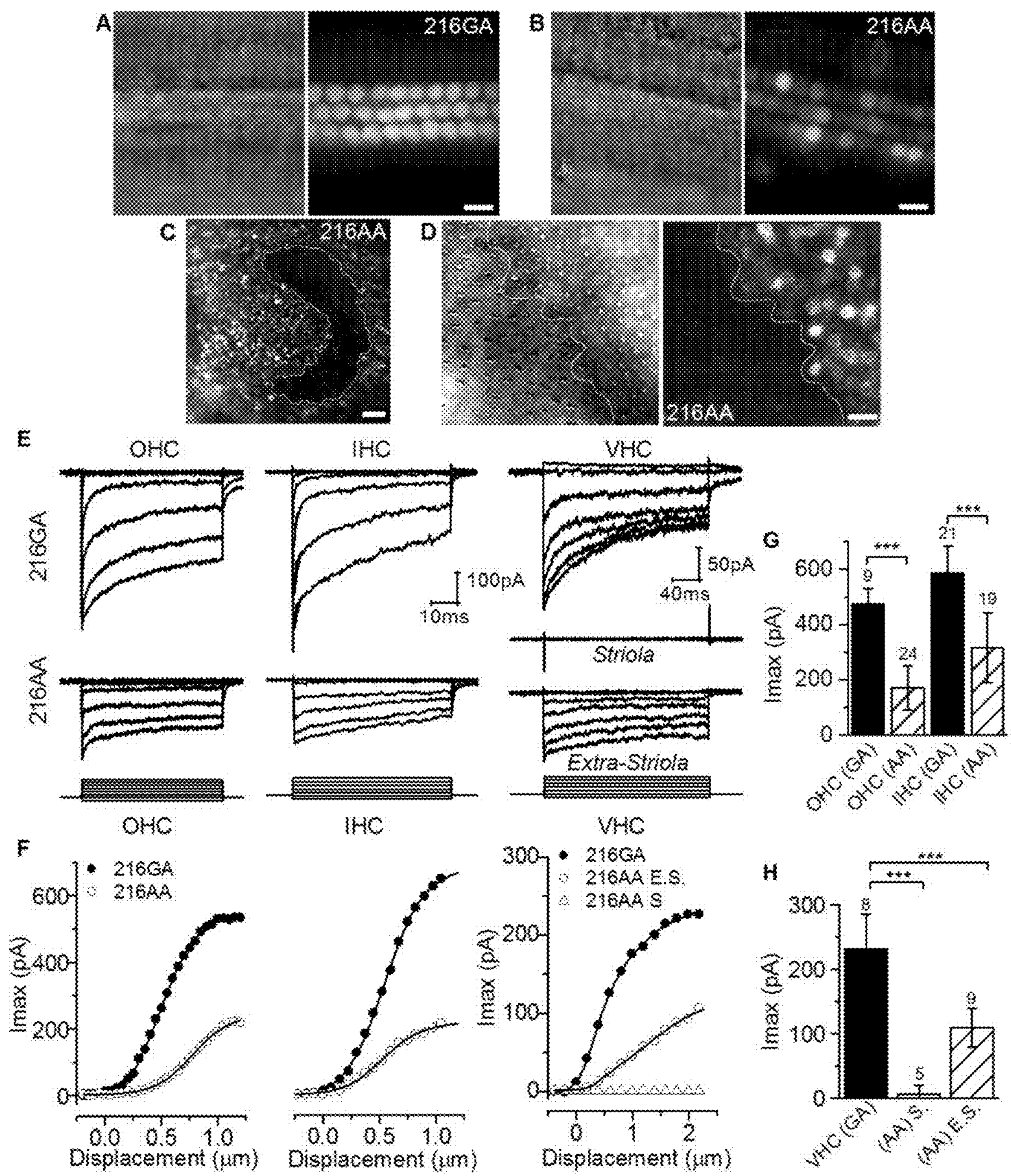
FIGS. 13A-13H are images showing mechanotransduction in hair cells of Ush1c c.216G>A neonatal mutant mice.
Figure 17:
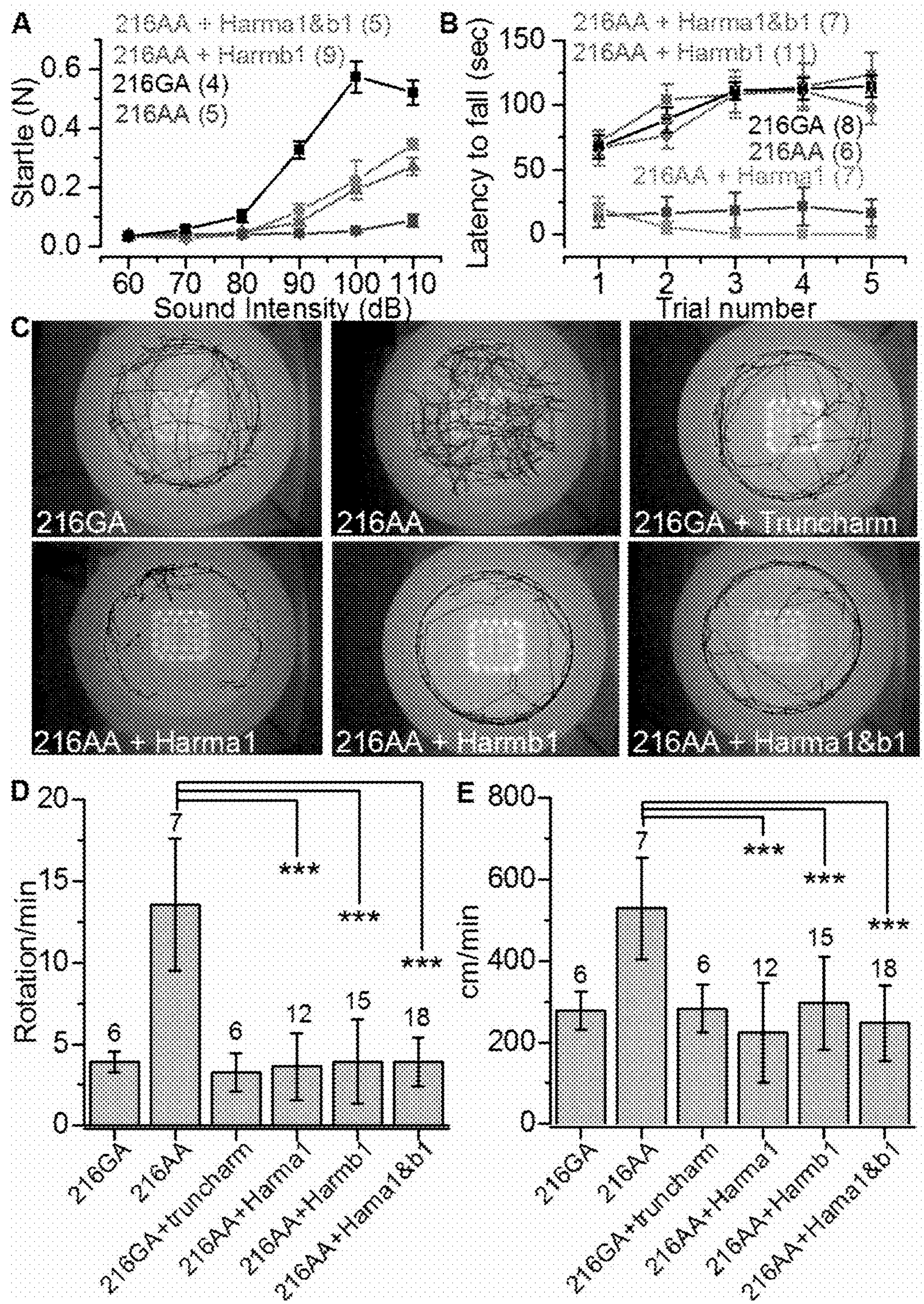
FIGS. 17A-17E are images showing startle response, rotarod performance and open field behavior recovery in mice injected with Anc80 harmonin-a1 and Anc80 harmonin-b1.

Behavioral assays demonstrated partial vestibular rescue with harmonin-a1, as circling behavior was abolished but harmonin-a1 injected mice failed the rotarod test. Mice injected with harmonin-b1, on the other hand, had functional recovery in both tests (FIG. 17). The absence of transduction and FM1-43 uptake in the striola regions indicates that hair cells of the striola region and perhaps type I cell function depends on proper harmonin expression (FIG. 13).

While auditory rescue was prominent at low but not high frequencies (FIG. 16), preservation of hair bundle morphology at 6 weeks was observed along the entire organ (FIG. 18). The absence of rescue at high frequencies is unlikely due to damage caused by the injection. High frequency hearing loss was not observed in any of the c.216GA injected with AAV vectors (FIG. 23C-23D). AAV targeting along the entire length of the cochlea argues against a lack of transduction efficiency at the base as an explanation. One possibility is that other harmonin isoforms, such as the short harmonin-c, may be necessary for rescue of function in the basal high frequency end of the cochlea. Alternatively, since cochlear development begins at the basal end, it is possible that by P0, hair cells from the basal high frequency end have matured beyond the point of repair. If this is the case embryonic intervention may allow better rescue in the high frequency region.

Part 3—Gene Therapy of Additional Mutations Involved in Hearing Loss

Example 3A—In Vivo Experiments

Anc80 vectors carrying the coding sequence for mouse TMC1 driven by a modified CMV promoter were generated using a helper virus free system and a double transfection method as described previously (Grimm et al., 2003, Mol. Ther., 7:839:50). A triple flag-tag (FLAG) sequence was fused to the C-terminal end of the TMC coding sequence to enable visualization of the expressed protein. Anc80-CMV-Tmc vector was purified using an iodixanol step gradient followed by ion exchange chromatography. Titers ranged from $1\times10^{12}$ to $1\times10^{13}$ gc/ml as measured by quantitative PCR using primer sets specific for the human beta-globin intronic element. Virus aliquots were stored at −80° C. and thawed just prior to use.

Mice, age P0-P2, were used for in vivo delivery of viral vectors as described below according to protocols approved by the Institutional Animal Care and Use Committee (protocols #2659, #2146) at Boston Children's Hospital. C57BL/6J (Jackson Laboratories) or Swiss Webster mouse lines (Taconic) were used for wild-type control mice, and mice that carried TMC1 mutant alleles (TMC1Δ/Δ or Tmc1−/−) were on a C57BL/6J background as described previously (Kawashima et al., 2011, J. Clin. Invest., 121: 4796-809).

To prepare tissue for evaluation, temporal bones were harvested from mouse pups at P0-P10. Pups were euthanized by rapid decapitation and temporal bones were dissected in MEM (Invitrogen) supplemented with 10 mM HEPES, 0.05 mg/ml ampicillin, and 0.01 mg/ml ciprofloxacin at pH 7.40. The membranous labyrinth was isolated under a dissection scope, Reissner's membrane was peeled back, and the tectorial membrane and stria vascularis were mechanically removed. Organ of Corti cultures were pinned flatly beneath a pair of thin glass fibers adhered at one end with Sylgard to an 18-mm round glass coverslip. The tissue was used acutely for electrophysiological studies. For mice older than P10, temporal bones were harvested after euthanizing the animal with inhaled $CO_2$, and cochlear whole mounts were generated.

All mean values and error bars presented in the figures represent mean±SD. Comparisons for statistical significance between injected ears and uninjected ears were performed using a two-tailed paired t test. $P<0.05$ was considered significant.

Example 3B—In Vivo Injection of Viral Vectors

Mouse pups (P0-P2) were injected via the round window membrane (RWM) using beveled glass microinjection pipettes. Pipettes were pulled from capillary glass on a P-2000 pipette puller (Sutter Instruments) and were beveled (~20 μm tip diameter at a 28° angle) using a micropipette beveler (Sutter Instruments). EMLA cream (lidocaine 2.5% and prilocaine 2.5%) was applied externally for analgesia using sterile swabs to cover the surgical site (left mastoid prominence). Body temperature was maintained on a 37° C. warming pad for 30-60 minutes prior to surgery.

Pups were anesthetized by rapid induction of hypothermia for 2-3 minutes until loss of consciousness, and this state was maintained on a cooling platform for 10-15 minutes during the surgery. The surgical site was disinfected by scrubbing with Betadine and wiping with 70% Ethanol in repetition three times. A post-auricular incision was made to expose the transparent otic bulla, a micropipette was advanced by micromanipulator (MP-30, Sutter Instrument Company) through the bulla and overlying fascia, and the RWM was penetrated by the tip of the micropipette.

Approximately 1 μl of virus at titers between $10^{12}$ and $10^{14}$ gc/mL ($10^9$ and $10^{11}$ total viral particles) was injected unilaterally at 0.1 μl/min into the left ear using a pneumatic microinjector (WPI Nanoliter 2010). The skin incision was closed using a 6-0 monofilament suture (Ethicon). Pups were then returned to the warming pad for recovery.

Example 3C—Immunofluorescence

Immunostaining was performed to determine the distribution of expression of a transgene delivered by a viral vector. To do so, immunostaining was performed on freshly dissected organs of Corti, immersion fixed for 1 h at room temperature with 4% paraformaldehyde diluted in PBS. The tissue was then rinsed in PBS, permeabilized in 0.01-0.1% Triton X-100 for 30 minutes, and counterstained for 1 h with AlexaFluor546-phalloidin (Molecular Probes, 1:200 dilution) to label filamentous actin.

For localization of exogenously expressed TMC::FLAG fusion proteins, the tissue was blocked for 1 hour using 2% BSA and 5% Normal Goat Serum, and was incubated overnight at 4° C. with an antibody to the FLAG motif (BD Biosciences, 1:200 dilution). For hair cell counts, tissue was blocked in Normal Goat Serum for 1 hour, stained with a rabbit anti-Myosin VIIa primary antibody (Proteus Biosciences, 1:1000 dilution) at 4° C. overnight, and labeled with goat anti-rabbit antibody conjugated to AlexaFluor488 (Life Technologies, 1:200 dilution) for 1 h. Samples were mounted on glass coverslips with Vectashield mounting medium (Vector Laboratories), and imaged at 10×-63× magnification using a Zeiss LSM700 confocal microscope.

Figure 26:
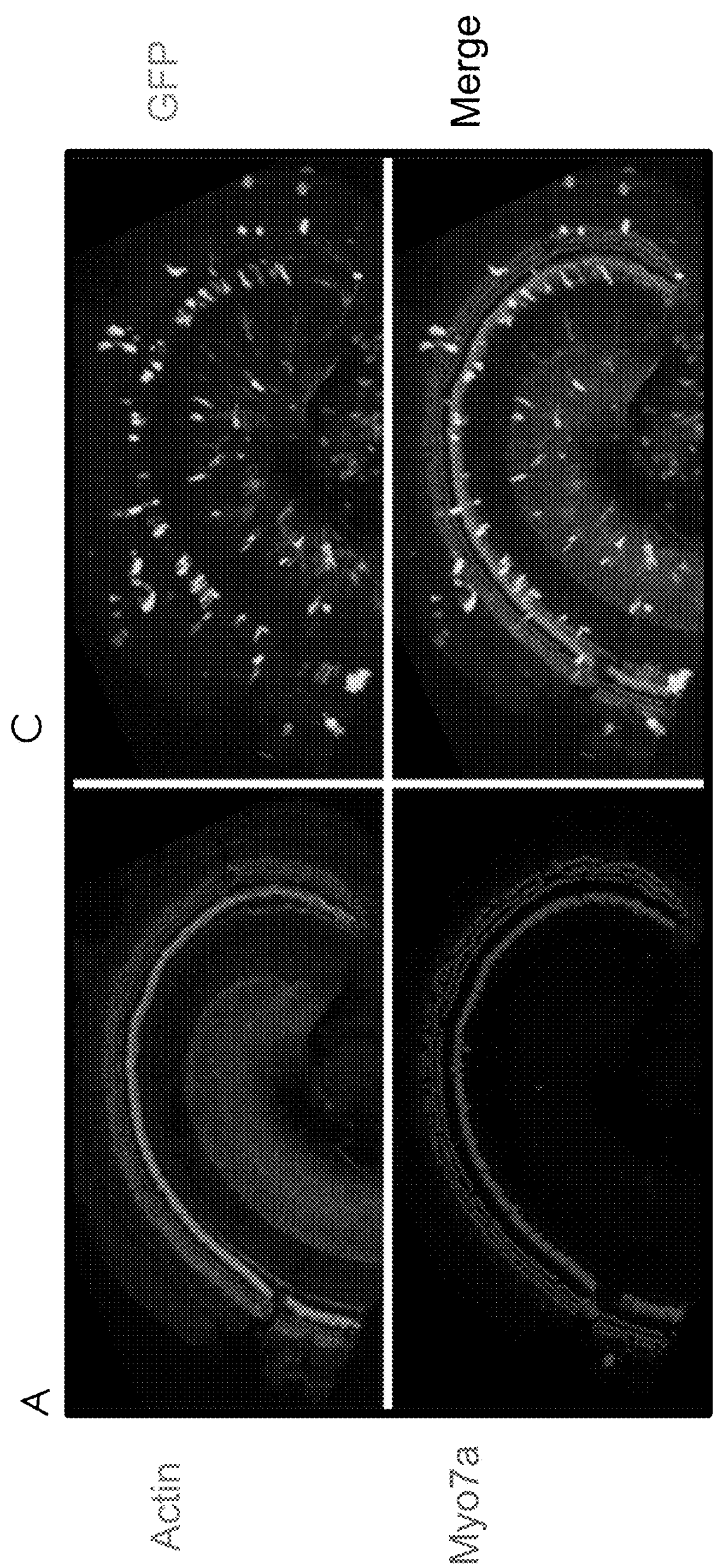

FIG. 26 shows immunofluorescence that demonstrates uniform Anc80 delivery of Harmonin to Ush1c mutant mice, and FIG. 28 shows immunofluorescence that demonstrates Anc80 delivery of KCNQ4 to cells in KCNQ4 mutant mice. Thus, Anc80 is an effective vector for treating a number of different genetic defects (at a number of different genetic loci) that result in hearing loss.

Example 3D—Hair Cell Electrophysiology

Organotypic cochlear cultures were bathed in standard artificial perilymph containing 137 mM NaCl, 0.7 mM $NaH_2PO_4$, 5.8 mM KCl, 1.3 mM $CaCl_2$), 0.9 mM $MgCl_2$, 10 mM Hepes, and 5.6 mM D-glucose. Vitamins (1:50) and amino acids (1:100) were added to the solution from concentrates (Invitrogen), and NaOH was used to adjust the final pH to 7.40 (310 mosmol/kg). Recording pipettes (3 to 5 megohms) were pulled from R6 capillary glass (King Precision Glass) and filled with intracellular solution containing 135 mM CsCl, 5 mM Hepes, 5 mM EGTA, 2.5 mM $MgCl_2$, 2.5 mM $Na_2$-adenosine triphosphate, and 0.1 mM $CaCl_2$), where CsOH was used to adjust the final pH to 7.40 (285 mosmol/kg). Whole-cell, tight-seal voltage-clamp recordings were done at −84 mV at room temperature (22° to 24° C.) using an Axopatch 200B amplifier (Molecular Devices). Sensory transduction currents were filtered at 10 kHz with a low-pass Bessel filter and digitized at ≥20 kHz with a 16-bit acquisition board (Digidata 1440A) and pCLAMP 10 software (Molecular Devices). Data were stored for offline analysis using OriginPro 8 (OriginLab).

FIG. 29 shows recovery of potassium currents to near wild type levels (FIG. 29A) in KCNQ4−/− cells transfected with Anc80-KCNQ4 (FIG. 10C) relative to the mutant mice (FIG. 29B), thereby demonstrating that gene therapy using Anc80 is capable of restoring function.

Example 3E—Auditory Brainstem Responses (ABR)

ABR recordings were conducted as described previously (Maison et al., 2010, J. Neurosci., 30:6751-62). Briefly, P25-P30 mice were anesthetized via IP injection (0.1 ml/10 g-body weight) with 50 mg of ketamine and 5 mg of xylazine diluted into 5 ml of 0.9% saline. ABR experiments were performed at 32° C. in a sound-proof chamber. To test hearing function, mice were presented pure tone stimuli of 5.6 kHz, 8 kHz, 11.3 k Hz, 16 kHz, 22.6 kHz, or 32 kHz at sound pressure levels between 10 and 115 dB in 5 dB steps until a threshold intensity that evoked a reproducible ABR waveform (peaks I-IV) was detected. Using an alternating polarity stimulus, 512 to 1024 responses were collected and averaged for each sound pressure level. Waveforms with amplitude larger than 15 pV (peak-to-trough) were discarded by an "artifact reject" function.

Prior to the onset of ABR testing, the flap of skin and cartilage that typically obscures the entrance of the external auditory meatus was trimmed away with dissecting scissors, and sound pressure at the entrance of the ear canal was calibrated for each individual test subject at all stimulus frequencies. Acoustic stimuli were delivered directly to the studied ear through a custom probe tube speaker/microphone assembly (EPL PXI Systems) consisting of two electrostatic earphones (CUI Miniature Dynamics) to generate primary tones and a Knowles miniature microphone (Electret Condenser) to record ear-canal sound pressure. Sound stimuli consisted of 5-ms tone bursts (0.5 ms rise-fall with a $\cos^2$ onset, delivered at 40/s).

ABR signals were collected using subcutaneous needle electrodes inserted at the pinna (active electrode), vertex (reference electrode), and rump (ground electrode). ABR potentials were amplified (10,000×), pass-filtered (0.3-10 kHz), and digitized using custom data acquisition software (LabVIEW). Sound stimuli and electrode voltage were sampled at 40-μs intervals using a digital I-O board (National Instruments) and stored for offline analysis. Threshold was defined visually as the lowest decibel level at which any wave (I-IV) could be detected and reproduced with increasing sound intensities. ABR thresholds were averaged within each experimental group and used for statistical analysis.

FIG. 27 graphically demonstrates that delivery of an Anc80 viral vector encoding and expressing Harmonin can provide nearly complete recovery of auditory function, particularly at lower frequencies (e.g., about 5 to about 22 kHz).

Example 3F—Quantitative RT-PCR Analysis

Experiments were performed to evaluate the amount of virus present in the cochlea following in vivo administration. Two TMC1−/− mice were injected in the left ear at P1. Cochlea were excised from left and right ears and maintained in culture for 3 days, the equivalent of P10. RNA was extracted and quality was confirmed using an Agilent Bioanalyzer (Agilent Technologies), and reverse transcribed into cDNA for quantitative RT-PCR analysis with efficient primer sets specific to TMC1 with SYBR GreenER qPCR reagent (Invitrogen) as previously described (Kawashima et al., 2011, J. Clin. Invest., 121:4796-809).

To amplify a fragment of TMC1, the following primers were used: 5'-CAT CTG CAG CCA ACT TTG GTG TGT-3' (SEQ ID NO:17) and 5'-AGA GGT AGC CGG AAA TTC AGC CAT-3' (SEQ ID NO:18). Expression levels were normalized to those of Actb (encoding β-actin) amplified with 5'-TGA GCG CAA GTA CTC TGT GTG GAT-3' (SEQ ID NO:19) and 5'-ACT CAT CGT ACT CCT GCT TGC TGA-3' (SEQ ID NO:20). All primers were designed to span introns, and validated using melt curve analysis and negative controls. Data were analyzed using the ΔΔCT method, relative to Actb and the difference between injected and uninjected ears.

These results demonstrate that, in injected ears, TMC1 mRNA expression was 12-fold higher than in uninjected ears.

Example 3G—FM1-43 Labeling

FM1-43 dye loading experiments were performed as described previously (Gale et al., 2001, J. Neurosci., 21:7013-25; Meyers et al., 2003, J. Neurosci., 23:4054-65; and Géléoc & Holt, 2003, Nat. Neurosci., 10:1019-20). Coverslips with adherent cochlear cultures were placed under an upright microscope (Zeiss Axioscope FS Plus) on a glass-bottomed chamber. Five-μM FM1-43FX (Invitrogen) diluted in artificial perilymph was applied for 10 sec and the tissue was washed three times in artificial perilymph to remove dye from the outer leaflet of the cell membrane. After 5 minutes, intracellular FM1-43 was imaged using an FM1-43 filter set and an epifluorescence light source with a 63× water immersion objective. The tissue was fixed and processed for immunofluorescence as described above.

FIG. 30 are the immunostaining images showing uptake of FM1-43 dye by cells exposed to an Anc80 viral vector as described herein, and FIG. 31 graphically demonstrates that TMC1 delivered by an Anc80 viral vector as described herein restores sensory transduction in Tmc1-deficient hair cells in vivo.

Example 3H—Distortion Product Otoacoustic Emissions (DPOAE)

DPOAE data were collected under the same conditions, and during the same recording sessions as ABR data. Primary tones were produced at a frequency ratio of 1.2 (f2/f1) for the generation of DPOAEs at 2f1-f2, where the f2 level was 10 dB sound pressure level below f1 level for each f2/f1 pair. The f2 levels were swept in 5-dB steps from 20 to 80 dB. Waveform and spectral averaging were used at each level to increase the signal-to-noise ratio of the recorded ear-canal sound pressure. The amplitude of the DPOAE at 2f1-f2 was extracted from the averaged spectra, along with the noise floor at nearby points in the spectrum. Iso-response curves were interpolated from plots of DPOAE amplitude versus sound level. Threshold was defined as the f2 level required to produce DPOAEs at 0 dB.

FIG. 32 graphically demonstrates that TMC1 delivered using an Anc80 viral vector as described herein rescues outer hair cell function in TMC1−/− mice, particularly at lower frequencies (e.g., about 5 to about 16 kHz).

OTHER EMBODIMENTS

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. An adeno-associated virus (AAV) vector comprising an Anc80 capsid protein and a transgene comprising ACTG1, ADCY1, ATOHI, ATP6V1B1, BDNF, BDP1, BSND, DATSPER2, CABP2, CD164, CDC14A, CEACAM16, CHD7, CCDC50, CLDN14, CLIC5, CLPP, COCH, COL2A1, COL4A3, COL4A4, COL4A5, COL9A1, COL9A2, COL11A1, COL11A2, CRYM, DCDC2, DFNA5, DFNB31, DFNB59, DIAPH1, EDN3, EDNRB, ELMOD3, EMOD3, EPS8, EPS8L2, ESPN, ESRRB, EYA1, EYA4, FAM65B, FOXII, GIPC3, GJB2, GJB3, GJB6, GPR98, GRHL2, GPSM2, GRXCR1, GRXCR2, HARS2, HGF, HOMER2, HSD17B4, ILDR1, KARS, KCNE1, KCNJ10, KCNQ1, KCNQ4, KITLG, LARS2, LHFPL5, LOXHD1, LRTOMT, MARVELD2, MCM2, MET, MIR183, MIRN96, MITF, MSRB3, MT-RNR1, MT-TS1, MYH14, MYH9, MYO15A, MYO1A, MY03A, MY06, NARS2, NDP,NF2, NT3, OSBPL2, OTOA, OTOF, OTOG, OTOGL, P2RX2, PAX3, PJVK, PNPT1, POLRID, POLRIC, POU3F4, POU4F3, PRPS1, PTPRQ, RDX, SIPR2, SEMA3E, SERPINB6, SLC17A8, SLC22A4, SLC26A4, SLC26A5, SIX1, SIX5, SMAC/DIABLO, SNAI2, SOX10, STRC, SYNE4, TBC1D24, TCOF1, TECTA, TIMM8A, TJP2, TNC, TMIE, TMEM132E, TMPRSS3, TRPN, TRIOBP, TSPEAR, USHIC, USHIG, USH2D, WFS1, or XIAP.

2. A method of delivering a transgene to at least 80% of inner hair cells (IHCs) and at least 80% of outer ear hair cells (OHCs) in a subject's inner ear to treat a hearing disorder, the method comprising:

administering the AAV vector of claim 1 to the inner ear in a subject.

3. The method of claim 2, wherein the transgene is further delivered to one or more spiral ganglion neurons, vestibular hair cells, vestibular ganglion neurons, supporting cells, and/or cells in the stria vascularis.

4. The method of claim 2, wherein the Anc80 capsid protein has the amino acid sequence shown in SEQ ID NO:1.

5. The method of claim 2, wherein the Anc80 capsid protein has the amino acid sequence shown in SEQ ID NO:2.

6. The method of claim 2, wherein the transgene is under control of a heterologous promoter sequence.

7. The method of claim 6, wherein the heterologous promoter sequence comprises a CMV promoter, a CBA promoter, a CASI promoter, a PGK promoter, a EF-1 promoter, an alpha9 nicotinic receptor promoter, a prestin promoter, a KCNQ4 promoter, a Myo7a promoter, a Myo6 promoter, a Gfil promoter, a Vglut3 promoter, or an Atoh1 promoter.

8. The method of claim 2, wherein the administering step comprises injecting the AAV vector through the round window.

9. The method of claim 2, wherein the AAV vector is administered during a cochleostomy or during a canalostomy.

10. The method of claim 2, wherein the AAV vector is administered to the middle ear and/or the round window via one or more drug delivery vehicles.

11. The method of claim 2, wherein expression of the transgene results in regeneration of inner hair cells (IHCs), or outer hair cells (OHCs), and one or more of spiral ganglion neurons, stria vascularis, vestibular hair cells, and/or vestibular ganglion neurons, thereby restoring hearing or vestibular function.

12. The AAV vector of claim 1, wherein the Anc80 capsid protein comprises the amino acid sequence of SEQ ID NO:1.

13. The AAV vector of claim 1, wherein the Anc80 capsid protein comprises the amino acid sequence of SEQ ID NO:2.

14. The AAV vector of claim 1, wherein the transgene is under control of a heterologous promoter sequence.

15. The AAV vector of claim 14, wherein the heterologous promoter sequence comprises a CMV promoter, a CBA promoter, a CASI promoter, a PGK promoter, a EF-1 promoter, an alpha9 nicotinic receptor promoter, a prestin promoter, a KCNQ4 promoter, a Myo7a promoter, a Myo6 promoter, a Gfil promoter, a Vglut3 promoter, or an Atoh1 promoter.

16. An adeno-associated virus (AAV) vector comprising an Anc80 capsid protein, and a transgene chosen from KCNQ4, USHIC, GJB2, SLC26A4, STRC, or OTOF.

17. The AAV vector of claim 16, wherein the Anc80 capsid protein comprises the amino acid sequence of SEQ ID NO: 1.

18. The AAV vector of claim 16, wherein the Anc80 capsid protein comprises the amino acid sequence of SEQ ID NO:2.

19. The AAV vector of claim 16, wherein the transgene is under control of a heterologous promoter sequence.

20. The AAV vector of claim 19, wherein the heterologous promoter sequence comprises a CMV promoter, a CBA promoter, a CASI promoter, a PGK promoter, a EF-1 promoter, an alpha9 nicotinic receptor promoter, a prestin promoter, a KCNQ4 promoter, a Myo7a promoter, a Myo6 promoter, a Gfil promoter, a Vglut3 promoter, or an Atoh1 promoter.

21. The AAV vector of claim 16, wherein the transgene comprises KCNQ4.

22. The AAV vector of claim 16, wherein the transgene comprises USHIC.

23. The AAV vector of claim 16, wherein the transgene comprises GJB2.

24. The AAV vector of claim 16, wherein the transgene comprises SLC26A4.

25. A method of delivering a transgene to at least 80% of inner hair cells (IHCs) and at least 80% of outer ear hair cells (OHCs) in a subject's inner ear to treat a hearing disorder, the method comprising administering the AAV vector of claim 16 to the inner ear in a subject.

26. The method of claim 25, wherein the transgene is further delivered to one or more of spiral ganglion neurons, vestibular hair cells, vestibular ganglion neurons, supporting cells, or cells in the stria vascularis.

27. The method of claim 25, wherein the Anc80 capsid protein has the amino acid sequence shown in SEQ ID NO:1.

28. The method of claim 25, wherein the Anc80 capsid protein has the amino acid sequence shown in SEQ ID NO:2.

* * * * *

UNITED STATES PATENT AND TRADEMARK OFFICE
CERTIFICATE OF CORRECTION

Page 1 of 2

PATENT NO. : 12,102,692 B2
APPLICATION NO. : 17/450008
DATED : October 1, 2024
INVENTOR(S) : Konstantina Stankovic et al.

It is certified that error appears in the above-identified patent and that said Letters Patent is hereby corrected as shown below:

On the Title Page

Item (72), (Inventors), Line 4, delete "Newtonr" and insert -- Newton --

In the Claims

In Column 89, Line 65, Claim 1, delete "ATOHI" and insert -- ATOH1 --

In Column 90, Line 66, Claim 1, delete "FOXII," and insert -- FOXI1, --

In Column 91, Line 5, Claim 1, delete "MY03A, MY06," and insert -- MYO3A, MYO6, --

In Column 91, Line 5, Claim 1, delete "NDP,NF2," and insert -- NDP, NF2, --

In Column 91, Line 7, Claim 1, delete "POLRID," and insert -- POLR1D, --

In Column 91, Line 7, Claim 1, delete "POLRIC," and insert -- POLR1C, --

In Column 91, Line 8, Claim 1, delete "SIPR2," and insert -- S1PR2, --

In Column 91, Line 13, Claim 1, delete "USHIC, USHIG," and insert -- USH1C, USH1G, --

In Column 91, Line 37, Claim 7, delete "Gfil" and insert -- Gfi1 --

In Column 92, Line 10, Claim 15, delete "Gfil" and insert -- Gfi1 --

In Column 92, Line 14 (approx.), Claim 16, delete "USHIC," and insert -- USH1C, --

In Column 92, Line 17 (approx.), Claim 17, delete "NO: 1." and insert -- NO:1. --

Signed and Sealed this
Third Day of December, 2024

Katherine Kelly Vidal
*Director of the United States Patent and Trademark Office*

CERTIFICATE OF CORRECTION (continued)
U.S. Pat. No. 12,102,692 B2

In Column 92, Line 29 (approx.), Claim 20, delete "Gfil" and insert -- Gfi1 --

In Column 92, Line 34 (approx.), Claim 22, delete "USHIC." and insert -- USH1C. --